US012599716B2

(12) United States Patent (10) Patent No.: US 12,599,716 B2

Cousineau et al. (45) Date of Patent: Apr. 14, 2026

(54) INTRAVENOUS INFUSION PUMP WITH CASSETTE INSERTION AND PUMP CONTROL USER INTERFACE

(71) Applicant: ICU Medical, Inc., San Clemente, CA (US)

(72) Inventors: Robert P. Cousineau, Boston, MA (US); Kerin L. Klagges-Kingsbury, Boxford, MA (US); James L. Cudney, Santee, CA (US); Roger P. Soucy, III, Kingston, NH (US)

(73) Assignee: ICU Medical, Inc., San Clemente, CA (US)

( * ) Notice: Subject to any disclaimer, the term of this patent is extended or adjusted under 35 U.S.C. 154(b) by 678 days.

(21) Appl. No.: 17/932,241

(22) Filed: Sep. 14, 2022

(65) Prior Publication Data

US 2023/0115595 A1 Apr. 13, 2023

Related U.S. Application Data

(60) Provisional application No. 63/254,922, filed on Oct. 12, 2021.

(51) Int. Cl.
A61M 5/14 (2006.01)
A61M 5/142 (2006.01)
A61M 5/172 (2006.01)

(52) U.S. Cl.
CPC ........ A61M 5/1413 (2013.01); A61M 5/1422 (2013.01); A61M 5/172 (2013.01);
(Continued)

(58) Field of Classification Search
None
See application file for complete search history.

(56) References Cited

U.S. PATENT DOCUMENTS

| | | |
|---|---|---|
| 3,401,337 A | 9/1968 | Beusman et al. |
| 3,484,681 A | 12/1969 | Grady, Jr. et al. |

(Continued)

FOREIGN PATENT DOCUMENTS

| | | |
|---|---|---|
| AU | 2013216679 | 9/2013 |
| BR | PI0704229-9 | 11/2009 |

(Continued)

OTHER PUBLICATIONS

Abbott Laboratories, "LifeCare® 5000, Plum®: Concurrent Flow Infusion System with DataPort™", System Operating Manual, Version 1.6, Jul. 1998, pp. 76.

(Continued)

*Primary Examiner* — Manuel A Mendez

(74) *Attorney, Agent, or Firm* — Knobbe Martens Olson & Bear LLP

(57) ABSTRACT

Disclosed in some embodiments is an electronic intravenous infusion pump provided with a disposable, insertable pump cartridge that is connectable to one or more intravenous fluid infusion sources, wherein a user interface on a touch display screen interacts with and responds to the user's insertion of the cassette, and/or wherein the pump is enabled to program a course of infusion for a patient based upon information obtained from the inserted cassette and/or the one or more fluid infusion sources connected to the cassette.

20 Claims, 19 Drawing Sheets

(52) U.S. Cl.
 CPC ... *A61M 2205/12* (2013.01); *A61M 2205/502*
  (2013.01); *A61M 2205/8206* (2013.01)

(56)                References Cited

U.S. PATENT DOCUMENTS

| | | | |
|---|---|---|---|
| 3,699,320 A | 10/1972 | Zimmerman et al. |
| 3,727,074 A | 4/1973 | Keller et al. |
| 3,731,679 A | 5/1973 | Wilhelmson et al. |
| 3,768,084 A | 10/1973 | Haynes |
| 3,770,354 A | 11/1973 | Tsuruta et al. |
| 3,778,702 A | 12/1973 | Finger |
| 3,806,821 A | 4/1974 | Niemeyer et al. |
| 3,838,565 A | 10/1974 | Carlyle |
| 3,847,138 A | 11/1974 | Gollub |
| 3,854,038 A | 12/1974 | McKinley |
| 3,886,459 A | 5/1975 | Hufford et al. |
| 3,890,554 A | 6/1975 | Yoshitake et al. |
| 3,894,431 A | 7/1975 | Muston et al. |
| 3,898,637 A | 8/1975 | Wolstenholme |
| 3,901,231 A | 8/1975 | Olson |
| 3,909,693 A | 9/1975 | Yoshitake et al. |
| 3,910,701 A | 10/1975 | Henderson |
| 3,911,343 A | 10/1975 | Oster |
| 3,919,608 A | 11/1975 | Usami et al. |
| 3,921,622 A | 11/1975 | Cole |
| 3,930,404 A | 1/1976 | Ryden, Jr. |
| 3,933,431 A | 1/1976 | Trujillo et al. |
| 3,935,876 A | 2/1976 | Massie et al. |
| 3,944,963 A | 3/1976 | Hively |
| 3,966,358 A | 6/1976 | Heimes et al. |
| 3,971,980 A | 7/1976 | Jungfer et al. |
| 3,974,681 A | 8/1976 | Namery |
| 3,974,683 A | 8/1976 | Martin |
| 3,985,467 A | 10/1976 | Lefferson |
| 3,990,444 A | 11/1976 | Vial |
| 3,997,888 A | 12/1976 | Kremer |
| 4,005,724 A | 2/1977 | Courtot |
| 4,014,206 A | 3/1977 | Taylor |
| 4,038,982 A | 8/1977 | Burke |
| 4,039,269 A | 8/1977 | Pickering |
| 4,048,474 A | 9/1977 | Olesen |
| 4,049,954 A | 9/1977 | Da Costa Vieira et al. |
| 4,055,175 A | 10/1977 | Clemens et al. |
| 4,057,228 A | 11/1977 | Völker et al. |
| 4,068,521 A | 1/1978 | Cosentino et al. |
| 4,078,562 A | 3/1978 | Friedman |
| 4,089,227 A | 5/1978 | Falgari et al. |
| 4,094,318 A | 6/1978 | Burke |
| 4,105,028 A | 8/1978 | Sadlier et al. |
| 4,114,144 A | 9/1978 | Hyman |
| 4,151,845 A | 5/1979 | Clemens |
| 4,155,362 A | 5/1979 | Jess |
| 4,164,986 A | 8/1979 | Eloy |
| 4,173,224 A | 11/1979 | Marx |
| 4,181,610 A | 1/1980 | Shintani et al. |
| 4,183,244 A | 1/1980 | Kohno et al. |
| 4,195,515 A | 4/1980 | Smoll |
| 4,210,138 A | 7/1980 | Jess et al. |
| 4,213,454 A | 7/1980 | Shim |
| 4,217,993 A | 8/1980 | Jess et al. |
| 4,240,294 A | 12/1980 | Grande |
| 4,240,438 A | 12/1980 | Updike et al. |
| 4,244,365 A | 1/1981 | McGill |
| 4,256,437 A | 3/1981 | Brown |
| 4,261,356 A | 4/1981 | Turner et al. |
| 4,264,861 A | 4/1981 | Radu et al. |
| 4,265,240 A | 5/1981 | Jenkins |
| 4,270,532 A | 6/1981 | Franetzki et al. |
| 4,277,226 A | 7/1981 | Archibald et al. |
| 4,278,085 A | 7/1981 | Shim |
| 4,280,495 A | 7/1981 | Lampert |
| 4,282,872 A | 8/1981 | Franetzki et al. |
| 4,286,202 A | 8/1981 | Clancy et al. |
| 4,290,346 A | 9/1981 | Bujan |
| 4,291,692 A | 9/1981 | Bowman et al. |
| 4,292,405 A | 9/1981 | Mascoli |
| 4,298,357 A | 11/1981 | Permic |
| 4,308,866 A | 1/1982 | Jeliffe |
| 4,312,341 A | 1/1982 | Zissimopoulos |
| 4,319,568 A | 3/1982 | Tregoning |
| 4,322,201 A | 3/1982 | Archibald |
| 4,323,849 A | 4/1982 | Smith |
| 4,324,662 A | 4/1982 | Schnell |
| 4,328,800 A | 5/1982 | Marx |
| 4,328,801 A | 5/1982 | Marx |
| 4,333,045 A | 6/1982 | Oltendorf |
| 4,343,316 A | 8/1982 | Jespersen |
| 4,344,429 A | 8/1982 | Gupton et al. |
| 4,346,707 A | 8/1982 | Whitney et al. |
| 4,360,019 A | 11/1982 | Portner et al. |
| 4,366,384 A | 12/1982 | Jensen |
| 4,367,736 A | 1/1983 | Gupton |
| 4,370,983 A | 2/1983 | Lichtenstein et al. |
| 4,373,527 A | 2/1983 | Fischell |
| 4,379,452 A | 4/1983 | DeVries |
| 4,381,005 A | 4/1983 | Bujan |
| 4,384,578 A | 5/1983 | Winkler |
| 4,385,247 A | 5/1983 | Satomi |
| 4,391,598 A | 7/1983 | Thompson |
| 4,392,849 A | 7/1983 | Petre et al. |
| 4,394,862 A | 7/1983 | Shim |
| 4,395,259 A | 7/1983 | Prestele et al. |
| 4,397,194 A | 8/1983 | Soltz |
| 4,399,362 A | 8/1983 | Cormier et al. |
| 4,407,659 A | 10/1983 | Adam |
| 4,411,651 A | 10/1983 | Schulman |
| 4,418,565 A | 12/1983 | St. John |
| 4,432,699 A | 2/1984 | Beckman et al. |
| 4,432,761 A | 2/1984 | Dawe |
| 4,432,762 A | 2/1984 | Dawe |
| 4,443,218 A | 4/1984 | Decant, Jr. et al. |
| 4,444,546 A | 4/1984 | Pazemenas |
| 4,447,191 A | 5/1984 | Bilstad et al. |
| 4,447,224 A | 5/1984 | Decant, Jr. et al. |
| 4,453,931 A | 6/1984 | Pastrone |
| 4,457,751 A | 7/1984 | Rodler |
| 4,463,301 A | 7/1984 | Moriguchi et al. |
| 4,464,170 A | 8/1984 | Clemens |
| 4,467,654 A | 8/1984 | Murakami et al. |
| 4,468,222 A | 8/1984 | Lundquist |
| 4,468,601 A | 8/1984 | Chamran et al. |
| 4,469,481 A | 9/1984 | Kobayashi |
| 4,475,666 A | 10/1984 | Bilbrey et al. |
| 4,475,901 A | 10/1984 | Kraegen et al. |
| 4,477,756 A | 10/1984 | Moriguchi |
| 4,479,760 A | 10/1984 | Bilstad et al. |
| 4,480,218 A | 10/1984 | Hair |
| 4,480,483 A | 11/1984 | McShane |
| 4,483,202 A | 11/1984 | Ogua et al. |
| 4,487,601 A | 12/1984 | Lindemann |
| 4,492,909 A | 1/1985 | Hartwig |
| 4,496,346 A | 1/1985 | Mosteller |
| 4,498,843 A | 2/1985 | Schneider et al. |
| 4,501,531 A | 2/1985 | Bilstad et al. |
| 4,504,263 A | 3/1985 | Steuer |
| 4,507,112 A | 3/1985 | Hillel |
| 4,510,266 A | 4/1985 | Eertink |
| 4,513,796 A | 4/1985 | Miller et al. |
| 4,515,584 A | 5/1985 | Abe et al. |
| 4,519,792 A | 5/1985 | Dawe |
| 4,521,212 A | 6/1985 | Ruschke |
| 4,525,163 A | 6/1985 | Slavik et al. |
| 4,526,568 A | 7/1985 | Clemens et al. |
| 4,526,574 A | 7/1985 | Pekkarinen |
| 4,529,401 A | 7/1985 | Leslie et al. |
| 4,533,350 A | 8/1985 | Danby et al. |
| 4,543,955 A | 10/1985 | Schroeppel |
| 4,551,134 A | 11/1985 | Slavik et al. |
| 4,553,958 A | 11/1985 | LeCocq |
| 4,559,036 A | 12/1985 | Wunsch |
| 4,559,037 A | 12/1985 | Franetzki et al. |
| 4,559,044 A | 12/1985 | Robinson |
| 4,559,454 A | 12/1985 | Kramer |
| 4,565,500 A | 1/1986 | Jeensalute et al. |

(56)  References Cited

U.S. PATENT DOCUMENTS

| | | | |
|---|---|---|---|
| 4,583,981 A | 4/1986 | Urquhart et al. |
| 4,587,473 A | 5/1986 | Turvey |
| 4,607,520 A | 8/1986 | Dam |
| 4,617,014 A | 10/1986 | Cannon et al. |
| 4,624,661 A | 11/1986 | Arimond |
| 4,627,835 A | 12/1986 | Fenton, Jr. |
| 4,633,878 A | 1/1987 | Bombardieri |
| 4,634,426 A | 1/1987 | Kamen |
| 4,634,427 A | 1/1987 | Hannula et al. |
| 4,636,144 A | 1/1987 | Abe et al. |
| 4,637,813 A | 1/1987 | DeVries |
| 4,645,489 A | 2/1987 | Krumme |
| 4,648,869 A | 3/1987 | Bobo, Jr. |
| 4,652,260 A | 3/1987 | Fenton, Jr. et al. |
| 4,658,244 A | 4/1987 | Meijer |
| 4,668,216 A | 5/1987 | Martin |
| 4,668,945 A | 5/1987 | Aldrovandi et al. |
| 4,673,334 A | 6/1987 | Allington et al. |
| 4,673,389 A | 6/1987 | Archibald et al. |
| 4,676,776 A | 6/1987 | Howson et al. |
| 4,677,359 A | 6/1987 | Enami et al. |
| 4,678,979 A | 7/1987 | Hori |
| 4,678,998 A | 7/1987 | Muramatsu |
| 4,679,562 A | 7/1987 | Luksha |
| 4,683,428 A | 7/1987 | Gete |
| 4,685,903 A | 8/1987 | Cable et al. |
| 4,690,673 A | 9/1987 | Blomquist |
| 4,691,153 A | 9/1987 | Nishimura |
| 4,692,145 A | 9/1987 | Weyant |
| 4,696,671 A | 9/1987 | Epstein et al. |
| 4,697,129 A | 9/1987 | Enami et al. |
| 4,702,675 A | 10/1987 | Aldrovandi et al. |
| 4,705,506 A | 11/1987 | Archibald et al. |
| 4,710,106 A | 12/1987 | Iwata et al. |
| 4,714,462 A | 12/1987 | DiDomenico |
| 4,714,463 A | 12/1987 | Archibald et al. |
| 4,718,576 A | 1/1988 | Tamura et al. |
| 4,720,636 A | 1/1988 | Benner |
| 4,722,224 A | 2/1988 | Scheller et al. |
| 4,722,734 A | 2/1988 | Kolin |
| 4,731,051 A | 3/1988 | Fischell |
| 4,731,057 A | 3/1988 | Tanaka et al. |
| 4,737,711 A | 4/1988 | O'Hare |
| 4,739,346 A | 4/1988 | Buckley |
| 4,741,732 A | 5/1988 | Crankshaw et al. |
| 4,741,736 A | 5/1988 | Brown |
| 4,748,857 A | 6/1988 | Nakagawa |
| 4,751,445 A | 6/1988 | Sakai |
| 4,756,706 A | 7/1988 | Kerns et al. |
| 4,758,228 A | 7/1988 | Williams |
| 4,763,525 A | 8/1988 | Cobb |
| 4,764,166 A | 8/1988 | Spani et al. |
| 4,764,697 A | 8/1988 | Christiaens |
| 4,769,001 A | 9/1988 | Prince |
| 4,776,842 A | 10/1988 | Franetzki et al. |
| 4,781,687 A | 11/1988 | Wall |
| 4,784,576 A | 11/1988 | Bloom et al. |
| 4,785,184 A | 11/1988 | Bien et al. |
| 4,785,799 A | 11/1988 | Schoon et al. |
| 4,785,969 A | 11/1988 | McLaughlin |
| 4,786,800 A | 11/1988 | Kamen |
| 4,789,014 A | 12/1988 | DiGianfilippo |
| 4,797,655 A | 1/1989 | Orndal et al. |
| 4,803,389 A | 2/1989 | Ogawa et al. |
| 4,803,625 A | 2/1989 | Fu et al. |
| 4,818,186 A | 4/1989 | Pastrone et al. |
| 4,820,281 A | 4/1989 | Lawler |
| 4,821,558 A | 4/1989 | Pastrone et al. |
| 4,828,545 A | 5/1989 | Epstein et al. |
| 4,828,693 A | 5/1989 | Lindsay |
| 4,829,448 A | 5/1989 | Balding et al. |
| 4,838,856 A | 6/1989 | Mulreany et al. |
| 4,838,857 A | 6/1989 | Strowe et al. |
| 4,840,542 A | 6/1989 | Abbott |
| 4,842,584 A | 6/1989 | Pastrone et al. |
| 4,845,487 A | 7/1989 | Frantz et al. |
| 4,846,792 A | 7/1989 | Bobo et al. |
| 4,850,805 A | 7/1989 | Madsen et al. |
| 4,851,755 A | 7/1989 | Fincher |
| 4,854,324 A | 8/1989 | Hirschman et al. |
| 4,856,339 A | 8/1989 | Williams |
| 4,857,048 A | 8/1989 | Simons et al. |
| 4,857,050 A | 8/1989 | Lentz et al. |
| 4,858,154 A | 8/1989 | Anderson et al. |
| 4,863,425 A | 9/1989 | Slate et al. |
| 4,865,584 A | 9/1989 | Epstein et al. |
| 4,869,722 A | 9/1989 | Heyman |
| 4,874,359 A | 10/1989 | White et al. |
| 4,878,175 A | 10/1989 | Norden-Paul et al. |
| 4,881,413 A | 11/1989 | Georgi et al. |
| 4,882,575 A | 11/1989 | Kawahara |
| 4,884,013 A | 11/1989 | Jackson et al. |
| 4,884,065 A | 11/1989 | Crouse et al. |
| 4,886,422 A | 12/1989 | Takeuchi et al. |
| 4,898,576 A | 2/1990 | Philip |
| 4,898,578 A | 2/1990 | Rubalcaba, Jr. |
| 4,906,103 A | 3/1990 | Kao |
| 4,908,017 A | 3/1990 | Howson et al. |
| 4,908,019 A | 3/1990 | Urquhart et al. |
| 4,910,475 A | 3/1990 | Lin |
| 4,919,595 A | 4/1990 | Likuski et al. |
| 4,919,596 A | 4/1990 | Slate et al. |
| 4,925,444 A | 5/1990 | Orkin et al. |
| 4,927,411 A | 5/1990 | Pastrone et al. |
| 4,930,358 A | 6/1990 | Motegi et al. |
| 4,936,820 A | 6/1990 | Dennehey |
| 4,936,828 A | 6/1990 | Chiang |
| 4,938,079 A | 7/1990 | Goldberg |
| 4,943,279 A | 7/1990 | Samiotes et al. |
| 4,946,439 A | 8/1990 | Eggers |
| 4,947,856 A | 8/1990 | Beard |
| 4,950,235 A | 8/1990 | Slate et al. |
| 4,950,244 A | 8/1990 | Fellingham |
| 4,959,050 A | 9/1990 | Bobo, Jr. |
| 4,966,579 A | 10/1990 | Polaschegg |
| 4,968,941 A | 11/1990 | Rogers |
| 4,972,842 A | 11/1990 | Korten et al. |
| 4,976,687 A | 12/1990 | Martin |
| 4,978,335 A | 12/1990 | Arthur, III |
| 4,979,940 A | 12/1990 | Lapp et al. |
| 4,981,467 A | 1/1991 | Bobo et al. |
| 5,000,663 A | 3/1991 | Gorton |
| 5,000,739 A | 3/1991 | Kulisz et al. |
| 5,006,050 A | 4/1991 | Cooke et al. |
| 5,010,473 A | 4/1991 | Jacobs |
| 5,014,714 A | 5/1991 | Millay et al. |
| 5,014,798 A | 5/1991 | Glynn |
| 5,018,945 A | 5/1991 | D'Silva |
| 5,026,348 A | 6/1991 | Venegas |
| 5,028,857 A | 7/1991 | Taghezout |
| 5,032,112 A | 7/1991 | Fairchild et al. |
| 5,034,004 A | 7/1991 | Crankshaw |
| 5,035,143 A | 7/1991 | Latimer et al. |
| 5,040,699 A | 8/1991 | Gangemi |
| 5,041,086 A | 8/1991 | Koenig et al. |
| 5,043,706 A | 8/1991 | Oliver |
| 5,045,069 A | 9/1991 | Imparato |
| 5,049,047 A | 9/1991 | Polaschegg et al. |
| 5,052,230 A | 10/1991 | Lang |
| 5,053,747 A | 10/1991 | Slate et al. |
| 5,055,761 A | 10/1991 | Mills |
| 5,056,992 A | 10/1991 | Simons |
| 5,058,161 A | 10/1991 | Weiss |
| 5,059,171 A | 10/1991 | Bridge |
| 5,063,603 A | 11/1991 | Burt |
| 5,064,412 A | 11/1991 | Henke et al. |
| 5,078,683 A | 1/1992 | Sancoff et al. |
| 5,084,663 A | 1/1992 | Olsson |
| 5,084,828 A | 1/1992 | Kaufman et al. |
| 5,088,981 A | 2/1992 | Howson et al. |
| 5,096,385 A | 3/1992 | Georgi et al. |
| 5,097,505 A | 3/1992 | Weiss |
| 5,100,380 A | 3/1992 | Epstein et al. |
| 5,102,392 A | 4/1992 | Sakai et al. |

(56) References Cited

U.S. PATENT DOCUMENTS

| | | | |
|---|---|---|---|
| 5,103,211 A | 4/1992 | Daoud et al. |
| 5,104,374 A | 4/1992 | Bishko et al. |
| 5,108,367 A | 4/1992 | Epstein et al. |
| 5,109,850 A | 5/1992 | Blanco et al. |
| 5,116,203 A | 5/1992 | Nartwick et al. |
| 5,116,312 A | 5/1992 | Blakenship et al. |
| 5,116,316 A | 5/1992 | Sertic |
| 5,123,275 A | 6/1992 | Daoud et al. |
| 5,124,627 A | 6/1992 | Okada |
| 5,125,499 A | 6/1992 | Saathoff et al. |
| 5,131,816 A | 7/1992 | Brown |
| 5,132,603 A | 7/1992 | Yoshimoto |
| 5,153,827 A | 10/1992 | Coutre et al. |
| 5,158,441 A | 10/1992 | Aid |
| 5,161,222 A | 11/1992 | Montejo et al. |
| 5,174,472 A | 12/1992 | Raque et al. |
| 5,176,631 A | 1/1993 | Koenig |
| 5,176,646 A | 1/1993 | Kuroda |
| 5,179,340 A | 1/1993 | Rogers |
| 5,180,287 A | 1/1993 | Natwick et al. |
| 5,181,910 A | 1/1993 | Scanlon |
| 5,186,057 A | 2/1993 | Everhart |
| 5,188,603 A | 2/1993 | Vaillancourt |
| 5,190,522 A | 3/1993 | Wocicki et al. |
| 5,191,795 A | 3/1993 | Fellingham et al. |
| 5,192,340 A | 3/1993 | Grant et al. |
| 5,194,796 A | 3/1993 | Domeki et al. |
| 5,198,776 A | 3/1993 | Carr |
| 5,200,090 A | 4/1993 | Ford |
| 5,205,819 A | 4/1993 | Ross et al. |
| 5,206,522 A | 4/1993 | Danby et al. |
| 5,207,642 A | 5/1993 | Orkin et al. |
| 5,211,626 A | 5/1993 | Frank et al. |
| 5,213,573 A | 5/1993 | Sorich et al. |
| 5,215,450 A | 6/1993 | Tamari |
| 5,216,597 A | 6/1993 | Beckers |
| 5,219,099 A | 6/1993 | Spence et al. |
| 5,219,327 A | 6/1993 | Okada |
| 5,221,268 A | 6/1993 | Barton et al. |
| 5,229,713 A | 7/1993 | Bullock et al. |
| 5,232,476 A | 8/1993 | Grant |
| 5,233,571 A | 8/1993 | Wirtschafter |
| 5,237,309 A | 8/1993 | Frantz et al. |
| 5,242,406 A | 9/1993 | Gross et al. |
| 5,242,408 A | 9/1993 | Jhuboo et al. |
| 5,243,982 A | 9/1993 | Möstl et al. |
| 5,244,463 A | 9/1993 | Cordner, Jr. et al. |
| 5,244,568 A | 9/1993 | Lindsay et al. |
| 5,254,096 A | 10/1993 | Rondelet et al. |
| 5,256,155 A | 10/1993 | Yerlikaya et al. |
| 5,256,156 A | 10/1993 | Kern et al. |
| 5,256,157 A | 10/1993 | Samiotes et al. |
| 5,257,206 A | 10/1993 | Hanson |
| 5,260,665 A | 11/1993 | Goldberg |
| 5,262,944 A | 11/1993 | Weisner et al. |
| 5,267,980 A | 12/1993 | Dirr et al. |
| 5,274,316 A | 12/1993 | Evans et al. |
| 5,276,610 A | 1/1994 | Maeda et al. |
| 5,280,728 A | 1/1994 | Sato et al. |
| 5,283,510 A | 2/1994 | Tamaki et al. |
| 5,287,851 A | 2/1994 | Beran et al. |
| 5,292,306 A | 3/1994 | Wynkoop et al. |
| 5,295,967 A | 3/1994 | Rondelet et al. |
| 5,298,021 A | 3/1994 | Sherer |
| 5,303,585 A | 4/1994 | Lichte |
| 5,304,126 A | 4/1994 | Epstein et al. |
| 5,304,216 A | 4/1994 | Wallace |
| 5,308,333 A | 5/1994 | Skakoon |
| 5,317,506 A | 5/1994 | Coutre et al. |
| 5,319,363 A | 6/1994 | Welch et al. |
| 5,319,979 A | 6/1994 | Abrahamson |
| 5,321,392 A | 6/1994 | Skakoon et al. |
| 5,325,170 A | 6/1994 | Bornhop |
| 5,325,728 A | 7/1994 | Zimmerman et al. |
| 5,328,460 A | 7/1994 | Lord et al. |
| 5,330,634 A | 7/1994 | Wong et al. |
| 5,333,497 A | 8/1994 | Braend et al. |
| 5,336,051 A | 8/1994 | Tamari |
| 5,338,157 A | 8/1994 | Blomquist |
| 5,342,298 A | 8/1994 | Michaels |
| 5,343,734 A | 9/1994 | Maeda et al. |
| 5,343,885 A | 9/1994 | Grant |
| 5,346,466 A | 9/1994 | Yerlikaya et al. |
| 5,356,378 A | 10/1994 | Doan et al. |
| 5,359,271 A | 10/1994 | Husher |
| D352,778 S | 11/1994 | Irvin et al. |
| 5,364,346 A | 11/1994 | Schrezenmeir |
| 5,366,346 A | 11/1994 | Danby |
| 5,368,562 A | 11/1994 | Blomquist et al. |
| 5,374,865 A | 12/1994 | Yoshimura et al. |
| 5,376,070 A | 12/1994 | Purvis et al. |
| 5,378,231 A | 1/1995 | Johnson et al. |
| 5,382,232 A | 1/1995 | Hague et al. |
| 5,383,369 A | 1/1995 | Khuri-Yakub et al. |
| 5,389,071 A | 2/1995 | Kawahara et al. |
| 5,389,078 A | 2/1995 | Zalesky et al. |
| 5,392,638 A | 2/1995 | Kawahara |
| 5,394,732 A | 3/1995 | Johnson et al. |
| 5,395,320 A | 3/1995 | Padda et al. |
| 5,399,171 A | 3/1995 | Bowman et al. |
| 5,406,954 A | 4/1995 | Tomita |
| 5,408,326 A | 4/1995 | Priestley |
| 5,415,528 A | 5/1995 | Ogden et al. |
| 5,417,119 A | 5/1995 | Smoll |
| 5,417,222 A | 5/1995 | Dempsey et al. |
| 5,417,395 A | 5/1995 | Fowler et al. |
| 5,418,443 A | 5/1995 | Kikuchi |
| 5,421,208 A | 6/1995 | Packard et al. |
| 5,423,748 A | 6/1995 | Uhala |
| 5,423,749 A | 6/1995 | Merte et al. |
| 5,423,759 A | 6/1995 | Campbell |
| 5,428,284 A | 6/1995 | Kaneda et al. |
| 5,429,485 A | 7/1995 | Dodge |
| 5,429,601 A | 7/1995 | Conley |
| 5,429,602 A | 7/1995 | Hauser |
| 5,431,627 A | 7/1995 | Pastrone et al. |
| 5,434,508 A | 7/1995 | Ishida |
| 5,437,624 A | 8/1995 | Langley et al. |
| 5,444,316 A | 8/1995 | Ohya et al. |
| 5,444,378 A | 8/1995 | Rogers |
| 5,445,621 A | 8/1995 | Poli et al. |
| 5,450,758 A | 9/1995 | Smoll |
| 5,451,881 A | 9/1995 | Finger |
| 5,455,423 A | 10/1995 | Mount et al. |
| 5,455,851 A | 10/1995 | Chaco et al. |
| 5,463,906 A | 11/1995 | Spani et al. |
| 5,464,392 A | 11/1995 | Epstein et al. |
| 5,465,082 A | 11/1995 | Chaco |
| 5,469,851 A | 11/1995 | Lipschutz |
| 5,473,948 A | 12/1995 | Moss et al. |
| 5,480,294 A | 1/1996 | Di Perna et al. |
| 5,482,438 A | 1/1996 | Anderson et al. |
| 5,485,408 A | 1/1996 | Blomquist |
| 5,486,286 A | 1/1996 | Peterson et al. |
| D367,528 S | 2/1996 | Martson et al. |
| 5,489,265 A | 2/1996 | Montalvo et al. |
| 5,495,566 A | 2/1996 | Kwatinetz |
| 5,496,273 A | 3/1996 | Pastrone et al. |
| 5,505,696 A | 4/1996 | Miki |
| 5,505,828 A | 4/1996 | Wong et al. |
| 5,507,288 A | 4/1996 | Bocker et al. |
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,344 A | 6/1996 | Arzbaecher et al. |
| 5,527,630 A | 6/1996 | Nagata |
| 5,533,389 A | 7/1996 | Kamen et al. |
| 5,537,853 A | 7/1996 | Finburgh et al. |
| 5,542,040 A | 7/1996 | Chang et al. |
| 5,545,140 A | 8/1996 | Conero et al. |
| 5,547,470 A | 8/1996 | Johnson et al. |
| 5,551,850 A | 9/1996 | Williamson et al. |
| 5,554,013 A | 9/1996 | Owens et al. |

(56) References Cited

U.S. PATENT DOCUMENTS

| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |
| 5,620,608 A | 4/1997 | Rosa et al. |
| 5,626,140 A | 5/1997 | Feldman et al. |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| D384,052 S | 9/1997 | Kodosky |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillén et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,685,866 A | 11/1997 | Lopez |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Stemby |
| 5,733,259 A | 3/1998 | Valcke et al. |
| 5,734,464 A | 3/1998 | Gibbs |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A | 7/1998 | Engleson et al. |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A | 9/1998 | Duffy et al. |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| D400,195 S | 10/1998 | Utesch |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,875,195 A | 2/1999 | Dixon |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |
| 5,894,209 A | 4/1999 | Takagi et al. |
| 5,897,493 A | 4/1999 | Brown |
| 5,897,498 A | 4/1999 | Canfield, II et al. |
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesier |
| 5,910,252 A | 6/1999 | Truitt et al. |
| 5,915,240 A | 6/1999 | Karpf |
| 5,920,263 A | 7/1999 | Huttenhoff et al. |
| 5,923,159 A | 7/1999 | Ezell |
| 5,924,074 A | 7/1999 | Evans |
| 5,927,349 A | 7/1999 | Martucci |
| 5,932,119 A | 8/1999 | Kaplan et al. |
| 5,932,987 A | 8/1999 | McLoughlin |
| 5,935,066 A | 8/1999 | Harris |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |
| 5,954,696 A | 9/1999 | Ryan et al. |

(56)                  References Cited

U.S. PATENT DOCUMENTS

| | | | |
|---|---|---|---|
| 5,956,023 | A | 9/1999 | Lyle et al. |
| 5,956,501 | A | 9/1999 | Brown |
| 5,957,885 | A | 9/1999 | Bollish et al. |
| 5,957,890 | A | 9/1999 | Mann et al. |
| 5,971,594 | A | 10/1999 | Sahai et al. |
| 5,973,497 | A | 10/1999 | Bergk et al. |
| 5,975,081 | A | 11/1999 | Hood et al. |
| 5,989,222 | A | 11/1999 | Cole et al. |
| 5,990,838 | A | 11/1999 | Burns et al. |
| 5,991,525 | A | 11/1999 | Shah et al. |
| 5,993,393 | A | 11/1999 | Ryan et al. |
| 5,994,876 | A | 11/1999 | Canny et al. |
| 5,997,476 | A | 12/1999 | Brown |
| 6,000,828 | A | 12/1999 | Leet |
| 6,003,006 | A | 12/1999 | Colella et al. |
| 6,003,388 | A | 12/1999 | Oeftering |
| D418,497 | S | 1/2000 | Howard et al. |
| 6,012,034 | A | 1/2000 | Hamparian et al. |
| 6,017,318 | A | 1/2000 | Gauthier et al. |
| 6,017,493 | A | 1/2000 | Cambron |
| 6,021,392 | A | 2/2000 | Lester et al. |
| 6,023,977 | A | 2/2000 | Langdon et al. |
| 6,024,539 | A | 2/2000 | Blomquist |
| 6,027,441 | A | 2/2000 | Cantu |
| 6,028,412 | A | 2/2000 | Shine et al. |
| 6,032,676 | A | 3/2000 | Moore |
| 6,033,561 | A | 3/2000 | Schoendorfer |
| 6,036,017 | A | 3/2000 | Bayliss, IV |
| 6,068,612 | A | 5/2000 | Bowman |
| 6,068,615 | A | 5/2000 | Brown et al. |
| 6,073,106 | A | 6/2000 | Rozen et al. |
| 6,077,246 | A | 6/2000 | Kullas et al. |
| 6,083,206 | A | 7/2000 | Molko |
| 6,089,104 | A | 7/2000 | Chang |
| 6,104,295 | A | 8/2000 | Gaisser et al. |
| 6,110,152 | A | 8/2000 | Kovelman |
| 6,110,153 | A | 8/2000 | Davis |
| RE36,871 | E | 9/2000 | Epstein et al. |
| 6,120,459 | A | 9/2000 | Nitzan et al. |
| 6,122,536 | A | 9/2000 | Sun et al. |
| 6,142,008 | A | 11/2000 | Cole et al. |
| 6,150,942 | A | 11/2000 | O'Brien |
| 6,157,914 | A | 12/2000 | Seto et al. |
| 6,158,288 | A | 12/2000 | Smith |
| 6,158,965 | A | 12/2000 | Butterfield et al. |
| 6,159,147 | A | 12/2000 | Lichter et al. |
| 6,159,186 | A | 12/2000 | Wickham et al. |
| 6,164,921 | A | 12/2000 | Moubayed et al. |
| 6,168,561 | B1 | 1/2001 | Cantu |
| 6,178,827 | B1 | 1/2001 | Feller |
| 6,182,667 | B1 | 2/2001 | Hanks et al. |
| 6,186,141 | B1 | 2/2001 | Pike et al. |
| 6,189,105 | B1 | 2/2001 | Lopes |
| 6,192,752 | B1 | 2/2001 | Blaine |
| 6,195,589 | B1 | 2/2001 | Ketcham |
| 6,202,711 | B1 | 3/2001 | Martucci |
| 6,203,528 | B1 | 3/2001 | Deckert |
| 6,208,107 | B1 | 3/2001 | Maske et al. |
| 6,212,936 | B1 | 4/2001 | Meisberger |
| 6,213,972 | B1 | 4/2001 | Butterfield |
| 6,231,320 | B1 | 5/2001 | Lawless et al. |
| 6,234,176 | B1 | 5/2001 | Domae et al. |
| 6,236,326 | B1 | 5/2001 | Murphy et al. |
| 6,237,398 | B1 | 5/2001 | Porat et al. |
| 6,241,704 | B1 | 6/2001 | Peterson et al. |
| 6,248,067 | B1 | 6/2001 | Causey, III et al. |
| 6,250,132 | B1 | 6/2001 | Drzewiecki |
| 6,259,355 | B1 | 7/2001 | Chaco et al. |
| 6,259,587 | B1 | 7/2001 | Sheldon et al. |
| 6,261,065 | B1 | 7/2001 | Nayak |
| 6,262,946 | B1 | 7/2001 | Khuri-Yakub et al. |
| 6,267,559 | B1 | 7/2001 | Mossman et al. |
| 6,267,725 | B1 | 7/2001 | Dubberstein et al. |
| 6,269,340 | B1 | 7/2001 | Ford et al. |
| 6,270,455 | B1 | 8/2001 | Brown |
| 6,271,813 | B1 | 8/2001 | Palalau |
| 6,277,072 | B1 | 8/2001 | Bardy |
| 6,277,099 | B1 | 8/2001 | Strowe et al. |
| 6,280,380 | B1 | 8/2001 | Bardy |
| 6,280,391 | B1 | 8/2001 | Olson et al. |
| 6,280,408 | B1 | 8/2001 | Sipin |
| 6,283,761 | B1 | 9/2001 | Joao |
| 6,285,155 | B1 | 9/2001 | Maske et al. |
| 6,312,378 | B1 | 11/2001 | Bardy |
| 6,322,516 | B1 | 11/2001 | Masuda et al. |
| 6,330,351 | B1 | 12/2001 | Yasunaga |
| 6,336,053 | B1 | 1/2002 | Beatty |
| 6,337,675 | B1 | 1/2002 | Toffolo et al. |
| 6,345,539 | B1 | 2/2002 | Rawes et al. |
| 6,347,553 | B1 | 2/2002 | Morris et al. |
| 6,349,740 | B1 | 2/2002 | Cho et al. |
| 6,358,225 | B1 | 3/2002 | Butterfield |
| 6,358,387 | B1 | 3/2002 | Kopf-Sill et al. |
| 6,362,591 | B1 | 3/2002 | Moberg |
| 6,385,505 | B1 | 5/2002 | Lipps |
| 6,386,050 | B1 | 5/2002 | Yin et al. |
| 6,394,958 | B1 | 5/2002 | Bratteli et al. |
| 6,396,583 | B1 | 5/2002 | Clare |
| D459,362 | S | 6/2002 | Platz |
| 6,398,760 | B1 | 6/2002 | Danby |
| 6,405,076 | B1 | 6/2002 | Taylor et al. |
| 6,408,679 | B1 | 6/2002 | Kline-Schoder et al. |
| 6,409,699 | B1 | 6/2002 | Ash |
| 6,413,238 | B1 | 7/2002 | Maget |
| 6,416,291 | B1 | 7/2002 | Butterfield et al. |
| 6,418,334 | B1 | 7/2002 | Unger et al. |
| 6,418,535 | B1 | 7/2002 | Kulakowski et al. |
| 6,445,053 | B1 | 9/2002 | Cho |
| 6,456,245 | B1 | 9/2002 | Crawford |
| 6,457,346 | B1 | 10/2002 | Kline-Schoder et al. |
| 6,463,785 | B1 | 10/2002 | Kline-Schoder et al. |
| 6,467,331 | B1 | 10/2002 | Kline-Schoder et al. |
| 6,468,242 | B1 | 10/2002 | Wilson et al. |
| 6,475,178 | B1 | 11/2002 | Krajewski |
| 6,481,980 | B1 | 11/2002 | Vandlik |
| 6,482,158 | B2 | 11/2002 | Mault |
| 6,482,185 | B1 | 11/2002 | Hartmann |
| 6,485,263 | B1 | 11/2002 | Bryant et al. |
| 6,485,418 | B2 | 11/2002 | Yasushi et al. |
| 6,485,465 | B2 | 11/2002 | Moberg et al. |
| 6,487,916 | B1 | 12/2002 | Gomm et al. |
| 6,489,896 | B1 | 12/2002 | Platt |
| 6,494,694 | B2 | 12/2002 | Lawless et al. |
| 6,494,831 | B1 | 12/2002 | Koritzinsky |
| 6,497,680 | B1 | 12/2002 | Holst et al. |
| 6,503,221 | B1 | 1/2003 | Briggs |
| 6,512,944 | B1 | 1/2003 | Kovtun et al. |
| 6,516,667 | B1 | 2/2003 | Broad et al. |
| 6,517,482 | B1 | 2/2003 | Eiden et al. |
| 6,519,569 | B1 | 2/2003 | White et al. |
| 6,529,751 | B1 | 3/2003 | Van Driel et al. |
| 6,531,708 | B1 | 3/2003 | Malmstrom |
| 6,539,315 | B1 | 3/2003 | Adams et al. |
| D473,238 | S | 4/2003 | Cockerill |
| 6,540,672 | B1 | 4/2003 | Simonsen et al. |
| 6,544,212 | B2 | 4/2003 | Galley et al. |
| 6,544,228 | B1 | 4/2003 | Heitmeier |
| 6,558,125 | B1 | 5/2003 | Futterknecht |
| 6,558,351 | B1 | 5/2003 | Steil et al. |
| 6,562,012 | B1 | 5/2003 | Brown et al. |
| 6,564,825 | B2 | 5/2003 | Lowery et al. |
| 6,565,509 | B1 | 5/2003 | Say et al. |
| 6,568,416 | B2 | 5/2003 | Tucker et al. |
| 6,572,542 | B1 | 6/2003 | Houben et al. |
| 6,572,545 | B2 | 6/2003 | Knobbe et al. |
| 6,572,576 | B2 | 6/2003 | Brugger et al. |
| 6,578,422 | B2 | 6/2003 | Lam et al. |
| 6,578,435 | B2 | 6/2003 | Gould et al. |
| 6,581,117 | B1 | 6/2003 | Klein et al. |
| RE38,189 | E | 7/2003 | Walker et al. |
| 6,585,675 | B1 | 7/2003 | O'Mahony et al. |
| 6,589,229 | B1 | 7/2003 | Connelly et al. |
| 6,589,792 | B1 | 7/2003 | Malachowski |
| 6,599,281 | B1 | 7/2003 | Struys et al. |

(56)         References Cited

U.S. PATENT DOCUMENTS

| | | |
|---|---|---|
| 6,599,282 B2 | 7/2003 | Burko |
| 6,602,191 B2 | 8/2003 | Quy |
| 6,605,072 B2 | 8/2003 | Struys et al. |
| 6,606,047 B1 | 8/2003 | Börjesson et al. |
| 6,609,047 B1 | 8/2003 | Lipps |
| 6,615,674 B2 | 9/2003 | Ohnishi |
| 6,616,633 B1 | 9/2003 | Butterfield et al. |
| 6,617,564 B2 | 9/2003 | Ockerse et al. |
| 6,618,916 B1 | 9/2003 | Eberle et al. |
| 6,622,542 B2 | 9/2003 | Derek |
| 6,622,561 B2 | 9/2003 | Lam et al. |
| D481,121 S | 10/2003 | Evans |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| D487,574 S | 3/2004 | Glaser |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,031,857 B2 | 4/2006 | Tarassenko et al. |
| 7,059,184 B2 | 6/2006 | Kanouda et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,171,992 B2 | 2/2007 | DiGianfilippo et al. |
| 7,174,789 B2 | 2/2007 | Orr et al. |
| 7,185,288 B2 | 2/2007 | McKeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |
| 7,253,779 B2 | 8/2007 | Greer et al. |
| 7,254,425 B2 | 8/2007 | Lowery et al. |

(56) References Cited

U.S. PATENT DOCUMENTS

| | | | |
|---|---|---|---|
| 7,258,534 | B2 | 8/2007 | Fathallah et al. |
| 7,267,664 | B2 | 9/2007 | Rizzo |
| 7,267,665 | B2 | 9/2007 | Steil et al. |
| 7,272,529 | B2 | 9/2007 | Hogan et al. |
| 7,278,983 | B2 | 10/2007 | Ireland et al. |
| 7,291,123 | B2 | 11/2007 | Baraldi et al. |
| 7,293,461 | B1 | 11/2007 | Gimdt |
| 7,294,109 | B2 | 11/2007 | Lovett et al. |
| 7,296,482 | B2 | 11/2007 | Schaffer et al. |
| 7,300,418 | B2 | 11/2007 | Zaleski |
| 7,305,883 | B2 | 12/2007 | Khuri-Yakub et al. |
| 7,327,273 | B2 | 2/2008 | Hung et al. |
| D563,986 | S | 3/2008 | Lettau |
| 7,338,470 | B2 | 3/2008 | Katz |
| 7,343,224 | B2 | 3/2008 | DiGianfilippo et al. |
| 7,347,836 | B2 | 3/2008 | Peterson et al. |
| 7,347,854 | B2 | 3/2008 | Shelton et al. |
| 7,354,420 | B2 | 4/2008 | Steil et al. |
| 7,356,382 | B2 | 4/2008 | Vanderveen |
| 7,360,999 | B2 | 4/2008 | Nelson et al. |
| 7,364,562 | B2 | 4/2008 | Braig et al. |
| 7,367,942 | B2 | 5/2008 | Grage et al. |
| 7,369,948 | B1 | 5/2008 | Ferenczi et al. |
| 7,384,410 | B2 | 6/2008 | Eggers et al. |
| 7,397,166 | B1 | 7/2008 | Morgan et al. |
| 7,398,183 | B2 | 7/2008 | Holland et al. |
| 7,399,277 | B2 | 7/2008 | Saidara et al. |
| 7,402,153 | B2 | 7/2008 | Steil et al. |
| 7,402,154 | B2 | 7/2008 | Mendez |
| 7,407,489 | B2 | 8/2008 | Mendez |
| 7,414,534 | B1 | 8/2008 | Kroll et al. |
| 7,415,895 | B2 | 8/2008 | Kurisaki et al. |
| 7,426,443 | B2 | 9/2008 | Simon |
| 7,430,675 | B2 | 9/2008 | Lee et al. |
| D581,426 | S | 11/2008 | Jasinski |
| 7,447,566 | B2 | 11/2008 | Knauper et al. |
| 7,447,643 | B1 | 11/2008 | Olson |
| 7,452,190 | B2 | 11/2008 | Bouton et al. |
| 7,454,314 | B2 | 11/2008 | Holland et al. |
| 7,471,994 | B2 | 12/2008 | Ford et al. |
| 7,477,997 | B2 | 1/2009 | Kaplit |
| 7,482,818 | B2 | 1/2009 | Greenwald et al. |
| 7,483,756 | B2 | 1/2009 | Engleson et al. |
| 7,490,021 | B2 | 2/2009 | Holland et al. |
| 7,491,187 | B2 | 2/2009 | Van Den Berghe et al. |
| 7,503,903 | B2 | 3/2009 | Carlisle et al. |
| 7,517,332 | B2 | 4/2009 | Tonelli et al. |
| 7,523,401 | B1 | 4/2009 | Aldridge |
| D593,125 | S | 5/2009 | Danton |
| 7,545,075 | B2 | 6/2009 | Huang et al. |
| D596,195 | S | 7/2009 | Wall |
| 7,556,616 | B2 | 7/2009 | Fathallah et al. |
| 7,561,986 | B2 | 7/2009 | Vanderveen et al. |
| 7,571,024 | B2 | 8/2009 | Duncan et al. |
| 7,605,730 | B2 | 10/2009 | Tomioka et al. |
| D604,306 | S | 11/2009 | Chow |
| 7,614,310 | B2 | 11/2009 | Konzelmann |
| 7,645,258 | B2 | 1/2010 | White et al. |
| 7,654,127 | B2 | 2/2010 | Krulevitch et al. |
| 7,657,443 | B2 | 2/2010 | Crass |
| 7,668,731 | B2 | 2/2010 | Martucci et al. |
| 7,678,048 | B1 | 3/2010 | Urbano et al. |
| 7,693,697 | B2 | 4/2010 | Westenskow et al. |
| 7,699,806 | B2 | 4/2010 | Ware et al. |
| 7,705,727 | B2 | 4/2010 | Pestotnik |
| D617,807 | S | 6/2010 | Christie |
| 7,726,179 | B2 | 6/2010 | Muller |
| D621,845 | S | 8/2010 | Anzures |
| 7,766,873 | B2 | 8/2010 | Moberg et al. |
| 7,775,126 | B2 | 8/2010 | Eckhardt |
| 7,775,127 | B2 | 8/2010 | Wade |
| 7,785,284 | B2 | 8/2010 | Baralsi et al. |
| 7,785,313 | B2 | 8/2010 | Mastrototaro |
| 7,786,909 | B2 | 8/2010 | Udupa et al. |
| 7,806,886 | B2 | 10/2010 | Kanderian, Jr. et al. |
| 7,826,981 | B2 | 11/2010 | Goode, Jr. et al. |
| 7,847,276 | B2 | 12/2010 | Carlisle |
| 7,860,583 | B2 | 12/2010 | Condurso et al. |
| 7,871,394 | B2 | 1/2011 | Halbert et al. |
| 7,876,443 | B2 | 1/2011 | Bernacki |
| 7,895,053 | B2 | 2/2011 | Holland et al. |
| 7,895,882 | B2 | 3/2011 | Carlisle |
| 7,896,834 | B2 | 3/2011 | Smisson, III |
| 7,896,842 | B2 | 3/2011 | Palmroos et al. |
| 7,905,710 | B2 | 3/2011 | Wang et al. |
| 7,933,780 | B2 | 4/2011 | de la Huerga |
| 7,938,817 | B2 | 5/2011 | Gelfand et al. |
| 7,945,452 | B2 | 5/2011 | Fathallah et al. |
| D642,195 | S | 7/2011 | Marks |
| 7,976,508 | B2 | 7/2011 | Hoag |
| 7,981,073 | B2 | 7/2011 | Mollstam |
| 7,981,082 | B2 | 7/2011 | Wang et al. |
| 7,998,134 | B2 | 8/2011 | Fangrow |
| 8,002,736 | B2 | 8/2011 | Patrick et al. |
| 8,034,020 | B2 | 10/2011 | Dewey |
| 8,038,593 | B2 | 10/2011 | Friedman et al. |
| 8,062,249 | B2 | 11/2011 | Willinska |
| 8,065,161 | B2 | 11/2011 | Howard et al. |
| 8,067,760 | B2 | 11/2011 | Carlisle |
| 8,075,514 | B2 | 12/2011 | Butterfield et al. |
| 8,075,546 | B2 | 12/2011 | Carlisle et al. |
| 8,078,983 | B2 | 12/2011 | Davis et al. |
| 8,121,857 | B2 | 2/2012 | Galasso et al. |
| 8,149,131 | B2 | 4/2012 | Blomquist |
| D659,709 | S | 5/2012 | Eby |
| 8,175,668 | B1 | 5/2012 | Nabutovsky et al. |
| 8,177,739 | B2 | 5/2012 | Cartledge et al. |
| 8,180,440 | B2 | 5/2012 | McCombie et al. |
| 8,185,322 | B2 | 5/2012 | Schroeder et al. |
| 8,197,444 | B1 | 6/2012 | Bazargan et al. |
| 8,219,413 | B2 | 7/2012 | Martinez et al. |
| 8,221,395 | B2 | 7/2012 | Shelton et al. |
| 8,226,597 | B2 | 7/2012 | Jacobson et al. |
| 8,231,578 | B2 | 7/2012 | Fathallah et al. |
| 8,234,128 | B2 | 7/2012 | Martucci et al. |
| D667,452 | S | 9/2012 | Wujcik |
| D667,840 | S | 9/2012 | Anzures |
| 8,271,106 | B2 | 9/2012 | Wehba et al. |
| 8,287,514 | B2 | 10/2012 | Miller et al. |
| 8,291,337 | B2 | 10/2012 | Gannin et al. |
| 8,313,308 | B2 | 11/2012 | Lawless et al. |
| 8,317,698 | B2 | 11/2012 | Lowery |
| 8,317,750 | B2 | 11/2012 | Ware et al. |
| 8,317,752 | B2 | 11/2012 | Cozmi et al. |
| 8,318,094 | B1 | 11/2012 | Bayandorian et al. |
| 8,340,792 | B2 | 12/2012 | Condurso et al. |
| 8,347,731 | B2 | 1/2013 | Genosar |
| 8,359,338 | B2 | 1/2013 | Butterfield et al. |
| 8,361,021 | B2 | 1/2013 | Wang et al. |
| 8,378,837 | B2 | 2/2013 | Wang et al. |
| 8,388,598 | B2 | 3/2013 | Steinkogler |
| 8,398,616 | B2 | 3/2013 | Budiman |
| 8,403,908 | B2 | 3/2013 | Jacobson et al. |
| D679,727 | S | 4/2013 | Abratowski |
| 8,409,164 | B2 | 4/2013 | Fangrow |
| 8,449,524 | B2 | 5/2013 | Braig et al. |
| 8,469,942 | B2 | 6/2013 | Kow et al. |
| 8,477,307 | B1 | 7/2013 | Yufa et al. |
| 8,494,879 | B2 | 7/2013 | Davis et al. |
| 8,504,179 | B2 | 8/2013 | Blomquist |
| 8,506,552 | B2 | 8/2013 | Rebours |
| 8,517,990 | B2 | 8/2013 | Teel et al. |
| 8,518,021 | B2 | 8/2013 | Stewart et al. |
| 8,522,832 | B2 | 9/2013 | Lopez et al. |
| 8,523,797 | B2 | 9/2013 | Lowery et al. |
| 8,539,812 | B2 | 9/2013 | Stringham et al. |
| 8,543,416 | B2 | 9/2013 | Palmroos et al. |
| 8,577,692 | B2 | 11/2013 | Silkaitis et al. |
| D696,270 | S | 12/2013 | Hyunjung et al. |
| D696,275 | S | 12/2013 | Tagliabue et al. |
| 8,606,596 | B1 | 12/2013 | Bochenko et al. |
| 8,622,990 | B2 | 1/2014 | Estes et al. |
| 8,630,722 | B2 | 1/2014 | Condurso et al. |

(56) References Cited

U.S. PATENT DOCUMENTS

| | | | |
|---|---|---|---|
| 8,641,670 B2* | 2/2014 | Yodfat | A61M 5/14248 604/67 |
| D701,517 S | 3/2014 | Thornton et al. | |
| 8,665,214 B2 | 3/2014 | Forutanpour et al. | |
| 8,666,769 B2 | 3/2014 | Butler et al. | |
| 8,700,421 B2 | 4/2014 | Feng et al. | |
| 8,706,233 B2 | 4/2014 | Su et al. | |
| D705,260 S | 5/2014 | Gerssen | |
| 8,719,045 B2 | 5/2014 | Yoon | |
| 8,721,584 B2 | 5/2014 | Braithwaite et al. | |
| 8,728,020 B2 | 5/2014 | Caleffi et al. | |
| D706,294 S | 6/2014 | Jewitt | |
| 8,758,306 B2 | 6/2014 | Lopez et al. | |
| 8,761,906 B2 | 6/2014 | Condurso et al. | |
| D709,091 S | 7/2014 | Kwon | |
| 8,768,719 B2 | 7/2014 | Wehba et al. | |
| 8,771,251 B2 | 7/2014 | Ruchti et al. | |
| 8,792,981 B2 | 7/2014 | Yudovsky et al. | |
| D710,370 S | 8/2014 | Inose et al. | |
| D711,916 S | 8/2014 | Matas | |
| D712,926 S | 9/2014 | Meegan | |
| D713,417 S | 9/2014 | Daniel | |
| D713,418 S | 9/2014 | Yang | |
| D713,420 S | 9/2014 | Dallmeyer | |
| 8,821,432 B2 | 9/2014 | Unverdorben | |
| 8,823,382 B2 | 9/2014 | Rondoni et al. | |
| 8,823,528 B2 | 9/2014 | Blomquist | |
| 8,857,269 B2 | 10/2014 | Johnson et al. | |
| 8,858,185 B2 | 10/2014 | Johnson et al. | |
| 8,905,965 B2 | 12/2014 | Mandro et al. | |
| D721,385 S | 1/2015 | Barling | |
| 8,948,734 B2 | 2/2015 | Vaglio | |
| 8,964,185 B1 | 2/2015 | Luo et al. | |
| 9,005,150 B2 | 4/2015 | Ware et al. | |
| 9,026,370 B2* | 5/2015 | Rubalcaba, Jr. | A61M 5/14212 702/19 |
| D731,535 S | 6/2015 | Seo et al. | |
| 9,084,855 B2 | 7/2015 | Ware et al. | |
| 9,114,217 B2 | 8/2015 | Sur et al. | |
| 9,134,735 B2 | 9/2015 | Lowery et al. | |
| 9,134,736 B2 | 9/2015 | Lowery et al. | |
| 9,138,526 B2 | 9/2015 | Ware et al. | |
| D742,413 S | 11/2015 | Torres | |
| D742,414 S | 11/2015 | Brunner | |
| D742,415 S | 11/2015 | Cahill | |
| D743,414 S | 11/2015 | Uno | |
| D744,001 S | 11/2015 | Orr | |
| 9,190,010 B2 | 11/2015 | Vik et al. | |
| D747,339 S | 1/2016 | Cohen | |
| 9,240,002 B2 | 1/2016 | Hume et al. | |
| D750,099 S | 2/2016 | Kadosh | |
| 9,272,089 B2 | 3/2016 | Jacobson et al. | |
| D754,740 S | 4/2016 | Cho et al. | |
| 9,316,216 B1 | 4/2016 | Cook et al. | |
| D757,099 S | 5/2016 | Seo | |
| 9,333,291 B2 | 5/2016 | Jacobson et al. | |
| D758,379 S | 6/2016 | Kadosh | |
| D759,036 S | 6/2016 | Evanes | |
| D760,238 S | 6/2016 | Suarez | |
| D760,248 S | 6/2016 | Smith | |
| D760,295 S | 6/2016 | Smith | |
| D760,788 S | 7/2016 | Cho | |
| D761,820 S | 7/2016 | Lee | |
| D762,238 S | 7/2016 | Day | |
| 9,381,296 B2 | 7/2016 | Arrizza et al. | |
| 9,393,362 B2 | 7/2016 | Cozmi et al. | |
| D764,538 S | 8/2016 | Lee | |
| 9,468,718 B2 | 10/2016 | Hung et al. | |
| 9,498,583 B2 | 11/2016 | Sur et al. | |
| D773,519 S | 12/2016 | Hurley | |
| D777,205 S | 1/2017 | Orr | |
| 9,545,475 B2 | 1/2017 | Borges et al. | |
| 9,545,476 B2 | 1/2017 | Qi et al. | |
| D779,537 S | 2/2017 | Wingate-Whyte | |
| D779,546 S | 2/2017 | Chetzroni | |
| D781,874 S | 3/2017 | Dunn | |
| D782,535 S | 3/2017 | Menz | |
| D785,018 S | 4/2017 | Lee et al. | |
| D785,040 S | 4/2017 | Day et al. | |
| 9,662,436 B2 | 5/2017 | Belkin et al. | |
| 9,707,341 B2 | 7/2017 | Dumas, III et al. | |
| 9,764,087 B2 | 9/2017 | Peterfreund et al. | |
| 9,773,330 B1 | 9/2017 | Douglas | |
| D803,872 S | 11/2017 | Cole | |
| D803,881 S | 11/2017 | Hurley | |
| D806,109 S | 12/2017 | Day | |
| 9,852,265 B1 | 12/2017 | Treacy et al. | |
| D809,006 S | 1/2018 | Mehta | |
| 9,883,987 B2 | 2/2018 | Lopez et al. | |
| 9,943,269 B2 | 4/2018 | Muhsin et al. | |
| D819,051 S | 5/2018 | Norris et al. | |
| D819,052 S | 5/2018 | Norris et al. | |
| D819,058 S | 5/2018 | Clediere | |
| 9,995,611 B2 | 6/2018 | Ruchti et al. | |
| 10,002,496 B2 | 6/2018 | Humphrey | |
| 10,022,498 B2 | 7/2018 | Ruchti et al. | |
| 10,046,112 B2 | 8/2018 | Oruklu et al. | |
| D827,665 S | 9/2018 | Segars | |
| D829,736 S | 10/2018 | Jochetz et al. | |
| 10,089,055 B1 | 10/2018 | Fryman | |
| 10,099,009 B1 | 10/2018 | Anderson et al. | |
| D835,145 S | 12/2018 | Cashner et al. | |
| 10,166,328 B2 | 1/2019 | Oruklu et al. | |
| 10,241,626 B2 | 3/2019 | Miyazawa | |
| 10,297,350 B2 | 5/2019 | Duke et al. | |
| 10,342,917 B2 | 7/2019 | Shubinsky et al. | |
| D862,495 S | 10/2019 | Vierra | |
| 10,430,761 B2 | 10/2019 | Hume et al. | |
| D865,777 S | 11/2019 | Kovács | |
| 10,463,788 B2 | 11/2019 | Day | |
| 10,549,248 B2 | 2/2020 | Brown et al. | |
| 10,578,474 B2 | 3/2020 | Ruchti et al. | |
| 10,596,316 B2 | 3/2020 | Dumas, III et al. | |
| 10,635,784 B2 | 4/2020 | Rubalcaba, Jr. et al. | |
| 10,656,894 B2 | 5/2020 | Fryman | |
| 10,682,102 B2 | 6/2020 | Declerck | |
| 10,709,885 B2 | 7/2020 | Janders et al. | |
| D898,055 S | 10/2020 | Connolly | |
| 10,850,024 B2 | 12/2020 | Day et al. | |
| 10,874,793 B2 | 12/2020 | Oruklu et al. | |
| D907,647 S | 1/2021 | Siebel et al. | |
| 10,994,077 B2* | 5/2021 | Rosinko | A61M 5/142 |
| 11,004,035 B2 | 5/2021 | Hume et al. | |
| 11,007,119 B2 | 5/2021 | Lopez et al. | |
| D922,430 S | 6/2021 | Kataoka et al. | |
| D922,432 S | 6/2021 | Kataoka et al. | |
| D923,050 S | 6/2021 | Kataoka et al. | |
| 11,029,911 B2 | 6/2021 | Fryman | |
| D926,201 S | 7/2021 | Bryant et al. | |
| D926,224 S | 7/2021 | Hummel | |
| D928,813 S | 8/2021 | Nurutdinov et al. | |
| D928,840 S | 8/2021 | Amit et al. | |
| 11,090,431 B2 | 8/2021 | Dumas et al. | |
| D931,884 S | 9/2021 | Bryant et al. | |
| D931,892 S | 9/2021 | Nurutdinov | |
| D934,282 S | 10/2021 | Clymer | |
| 11,135,360 B1 | 10/2021 | Jacobson et al. | |
| 11,219,715 B2 | 1/2022 | Gray et al. | |
| D943,613 S | 2/2022 | Bryant et al. | |
| 11,246,985 B2 | 2/2022 | Gylland et al. | |
| D944,839 S | 3/2022 | Harvey | |
| D946,608 S | 3/2022 | Higuchi | |
| 11,278,671 B2 | 3/2022 | Cavendish, Jr. et al. | |
| 11,298,456 B2 | 4/2022 | Shubinsky et al. | |
| 11,324,888 B2 | 5/2022 | Shubinsky et al. | |
| 11,344,668 B2 | 5/2022 | Sileika et al. | |
| 11,344,673 B2 | 5/2022 | Lindo et al. | |
| 11,376,361 B2 | 7/2022 | Ruchti et al. | |
| 11,378,430 B2 | 7/2022 | Ruchti et al. | |
| 11,395,875 B2 | 7/2022 | Rubalcaba, Jr. et al. | |
| D962,984 S | 9/2022 | Kuo et al. | |
| 11,433,177 B2 | 9/2022 | Oruklu et al. | |
| 11,439,570 B2 | 9/2022 | Lopez et al. | |
| D980,273 S | 3/2023 | Sigmon et al. | |

(56)　　　References Cited

U.S. PATENT DOCUMENTS

| | | | |
|---|---|---|---|
| 11,596,737 | B2 | 3/2023 | Dumas, III et al. |
| 11,599,854 | B2 | 3/2023 | Hume et al. |
| 11,623,042 | B2 | 4/2023 | Day |
| D986,271 | S | 5/2023 | Shor |
| D998,633 | S | 9/2023 | PJ |
| 11,868,161 | B2 | 1/2024 | Fryman |
| 11,883,361 | B2 | 1/2024 | Janssen |
| D1,017,633 | S | 3/2024 | Chung |
| D1,018,593 | S | 3/2024 | Chiah |
| 11,933,650 | B2 | 3/2024 | Ruchti et al. |
| D1,021,917 | S | 4/2024 | Ceniceroz |
| D1,023,027 | S | 4/2024 | Slettnes |
| D1,024,096 | S | 4/2024 | Zhong |
| 11,972,395 | B2 | 4/2024 | Hume et al. |
| D1,027,974 | S | 5/2024 | Correy |
| D1,032,623 | S | 6/2024 | Lim et al. |
| D1,033,461 | S | 7/2024 | Kasha |
| D1,035,698 | S | 7/2024 | Brown et al. |
| 12,048,831 | B2 | 7/2024 | Oruklu et al. |
| D1,039,563 | S | 8/2024 | Daley |
| D1,039,564 | S | 8/2024 | Leetz et al. |
| 12,059,551 | B2 | 8/2024 | Dumas, III et al. |
| 12,064,217 | B2 | 8/2024 | Ahmed et al. |
| 12,073,928 | B2 | 8/2024 | Freeman et al. |
| D1,042,473 | S | 9/2024 | Siebel et al. |
| 12,076,531 | B2 | 9/2024 | Shubinsky et al. |
| 12,083,310 | B2 | 9/2024 | Shubinsky et al. |
| 12,115,337 | B2 | 10/2024 | Day et al. |
| D1,054,430 | S | 12/2024 | Ellison et al. |
| D1,055,954 | S | 12/2024 | Fujisawa |
| 12,156,967 | B2 | 12/2024 | King et al. |
| D1,056,922 | S | 1/2025 | Pryor |
| D1,058,585 | S | 1/2025 | Chae |
| D1,059,400 | S | 1/2025 | Chai et al. |
| 12,201,811 | B2 | 1/2025 | Gylland et al. |
| D1,060,377 | S | 2/2025 | Lemay et al. |
| 12,239,818 | B2 | 3/2025 | Morton |
| D1,068,786 | S | 4/2025 | Holaman et al. |
| 12,268,843 | B2 | 4/2025 | Cavendish, Jr. et al. |
| 12,310,921 | B2 | 5/2025 | Janssen |
| 12,333,201 | B2 | 6/2025 | Fryman |
| 12,346,879 | B2 | 7/2025 | Hume et al. |
| D1,091,564 | S | 9/2025 | Cousineau et al. |
| 12,485,221 | B2 | 12/2025 | Lindo et al. |
| 2001/0007636 | A1 | 7/2001 | Butterfield |
| 2001/0014769 | A1 | 8/2001 | Bufe et al. |
| 2001/0015099 | A1 | 8/2001 | Blaine |
| 2001/0016056 | A1 | 8/2001 | Westphal et al. |
| 2001/0032099 | A1 | 10/2001 | Joao |
| 2001/0037060 | A1 | 11/2001 | Thompson et al. |
| 2001/0041869 | A1 | 11/2001 | Causey et al. |
| 2001/0044731 | A1 | 11/2001 | Coffman et al. |
| 2002/0003892 | A1 | 1/2002 | Iwanaga |
| 2002/0007116 | A1 | 1/2002 | Zatezalo et al. |
| 2002/0013545 | A1 | 1/2002 | Soltanpour et al. |
| 2002/0013551 | A1 | 1/2002 | Zaitsu et al. |
| 2002/0015018 | A1 | 2/2002 | Shimazu et al. |
| 2002/0018720 | A1 | 2/2002 | Carlisle et al. |
| 2002/0029776 | A1 | 3/2002 | Blomquist |
| 2002/0031838 | A1 | 3/2002 | Meinhart et al. |
| 2002/0032583 | A1 | 3/2002 | Joao |
| 2002/0040208 | A1 | 4/2002 | Flaherty et al. |
| 2002/0044059 | A1 | 4/2002 | Reeder et al. |
| 2002/0045806 | A1 | 4/2002 | Baker, Jr. et al. |
| 2002/0082728 | A1 | 6/2002 | Mueller et al. |
| 2002/0083771 | A1 | 7/2002 | Khuri-Yakub et al. |
| 2002/0085952 | A1 | 7/2002 | Ellingboe et al. |
| 2002/0087115 | A1 | 7/2002 | Hartlaub |
| 2002/0093641 | A1 | 7/2002 | Ortyn et al. |
| 2002/0095486 | A1 | 7/2002 | Bahl |
| 2002/0099282 | A1 | 7/2002 | Knobbe et al. |
| 2002/0099334 | A1 | 7/2002 | Hanson et al. |
| 2002/0143580 | A1 | 10/2002 | Bristol et al. |
| 2002/0147389 | A1 | 10/2002 | Cavallaro et al. |
| 2002/0152239 | A1 | 10/2002 | Bautista-Lloyd et al. |
| 2002/0158919 | A1 | 10/2002 | Nacey |
| 2002/0168278 | A1 | 11/2002 | Jeon et al. |
| 2002/0173703 | A1 | 11/2002 | Lebel et al. |
| 2002/0183693 | A1 | 12/2002 | Peterson et al. |
| 2003/0009244 | A1 | 1/2003 | Engleson |
| 2003/0013959 | A1 | 1/2003 | Grunwald et al. |
| 2003/0018289 | A1 | 1/2003 | Ng et al. |
| 2003/0018308 | A1 | 1/2003 | Tsai |
| 2003/0025602 | A1 | 2/2003 | Medema et al. |
| 2003/0028082 | A1 | 2/2003 | Thompson |
| 2003/0030001 | A1 | 2/2003 | Cooper et al. |
| 2003/0045840 | A1 | 3/2003 | Burko |
| 2003/0050621 | A1 | 3/2003 | Lebel et al. |
| 2003/0060688 | A1 | 3/2003 | Ciarniello et al. |
| 2003/0060765 | A1 | 3/2003 | Campbell et al. |
| 2003/0065537 | A1 | 4/2003 | Evans |
| 2003/0065589 | A1 | 4/2003 | Giacchetti |
| 2003/0073954 | A1 | 4/2003 | Moberg et al. |
| 2003/0079746 | A1 | 5/2003 | Hickle |
| 2003/0083583 | A1 | 5/2003 | Kovtun et al. |
| 2003/0091442 | A1 | 5/2003 | Bush et al. |
| 2003/0104982 | A1 | 6/2003 | Wittmann et al. |
| 2003/0106553 | A1 | 6/2003 | Vanderveen |
| 2003/0117296 | A1 | 6/2003 | Seely |
| 2003/0125662 | A1 | 7/2003 | Bui |
| 2003/0130616 | A1 | 7/2003 | Steil |
| 2003/0135087 | A1 | 7/2003 | Hickle et al. |
| 2003/0136193 | A1 | 7/2003 | Fujimoto |
| 2003/0139701 | A1 | 7/2003 | White et al. |
| 2003/0140928 | A1 | 7/2003 | Bui et al. |
| 2003/0140929 | A1 | 7/2003 | Wilkes et al. |
| 2003/0141981 | A1 | 7/2003 | Bui et al. |
| 2003/0143746 | A1 | 7/2003 | Sage, Jr. |
| 2003/0144878 | A1 | 7/2003 | Wilkes et al. |
| 2003/0158508 | A1 | 8/2003 | DiGianfilippo |
| 2003/0159741 | A1 | 8/2003 | Sparks |
| 2003/0160683 | A1 | 8/2003 | Blomquist |
| 2003/0163789 | A1 | 8/2003 | Blomquist |
| 2003/0167185 | A1 | 9/2003 | Gordon et al. |
| 2003/0173408 | A1 | 9/2003 | Mosher, Jr. et al. |
| 2003/0186833 | A1 | 10/2003 | Huff et al. |
| 2003/0187338 | A1 | 10/2003 | Say et al. |
| 2003/0200116 | A1 | 10/2003 | Forrester |
| 2003/0204274 | A1 | 10/2003 | Ullestad et al. |
| 2003/0204416 | A1 | 10/2003 | Acharya |
| 2003/0212364 | A1 | 11/2003 | Mann et al. |
| 2003/0212379 | A1 | 11/2003 | Bylund et al. |
| 2003/0216682 | A1 | 11/2003 | Junker |
| 2003/0217962 | A1 | 11/2003 | Childers et al. |
| 2003/0233071 | A1 | 12/2003 | Gillespie, Jr. et al. |
| 2004/0030277 | A1 | 2/2004 | O'Mahony et al. |
| 2004/0047736 | A1 | 3/2004 | Nose et al. |
| 2004/0057226 | A1 | 3/2004 | Berthou et al. |
| 2004/0064342 | A1 | 4/2004 | Browne et al. |
| 2004/0073125 | A1 | 4/2004 | Lovett et al. |
| 2004/0073161 | A1 | 4/2004 | Tachibana |
| 2004/0077996 | A1 | 4/2004 | Jasperson et al. |
| 2004/0082908 | A1 | 4/2004 | Whitehurst |
| 2004/0082918 | A1 | 4/2004 | Evans et al. |
| 2004/0104271 | A1 | 6/2004 | Martucci et al. |
| 2004/0119753 | A1 | 6/2004 | Zencke |
| 2004/0120825 | A1 | 6/2004 | Bouton et al. |
| 2004/0128162 | A1 | 7/2004 | Schlotterbeck et al. |
| 2004/0128163 | A1 | 7/2004 | Goodman et al. |
| 2004/0130573 | A1 | 7/2004 | Konuma |
| 2004/0133166 | A1 | 7/2004 | Moberg et al. |
| 2004/0145114 | A1 | 7/2004 | Ippolito et al. |
| 2004/0147034 | A1 | 7/2004 | Gore et al. |
| 2004/0149823 | A1 | 8/2004 | Aptekar |
| 2004/0152970 | A1 | 8/2004 | Hunter et al. |
| 2004/0158193 | A1 | 8/2004 | Bui et al. |
| 2004/0167464 | A1 | 8/2004 | Ireland et al. |
| 2004/0167465 | A1 | 8/2004 | Kohler |
| 2004/0167804 | A1 | 8/2004 | Simpson |
| 2004/0172222 | A1 | 9/2004 | Simpson et al. |
| 2004/0172283 | A1 | 9/2004 | Vanderveen |
| 2004/0172289 | A1 | 9/2004 | Kozic et al. |
| 2004/0172301 | A1 | 9/2004 | Mihai et al. |
| 2004/0172302 | A1 | 9/2004 | Martucci et al. |

(56) References Cited

U.S. PATENT DOCUMENTS

| | | |
|---|---|---|
| 2004/0176984 A1 | 9/2004 | White et al. |
| 2004/0181314 A1 | 9/2004 | Zaleski |
| 2004/0193025 A1 | 9/2004 | Steil et al. |
| 2004/0193325 A1 | 9/2004 | Bonderud |
| 2004/0193328 A1 | 9/2004 | Butterfield et al. |
| 2004/0204638 A1 | 10/2004 | Diab et al. |
| 2004/0204673 A1 | 10/2004 | Flaherty et al. |
| 2004/0220517 A1 | 11/2004 | Starkweather et al. |
| 2004/0225252 A1 | 11/2004 | Gillespie et al. |
| 2004/0225409 A1 | 11/2004 | Duncan et al. |
| 2004/0232219 A1 | 11/2004 | Fowler |
| 2004/0253123 A1 | 12/2004 | Xie et al. |
| 2004/0254434 A1 | 12/2004 | Goodnow et al. |
| 2004/0254513 A1 | 12/2004 | Shang et al. |
| 2005/0021006 A1 | 1/2005 | Tonnies |
| 2005/0021297 A1 | 1/2005 | Hartlaub |
| 2005/0022274 A1 | 1/2005 | Campbell et al. |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0075544 A1 | 4/2005 | Shapiro et al. |
| 2005/0096593 A1 | 5/2005 | Pope et al. |
| 2005/0099624 A1 | 5/2005 | Staehr |
| 2005/0107923 A1 | 5/2005 | Vanderveen |
| 2005/0108057 A1 | 5/2005 | Cohen et al. |
| 2005/0119597 A1 | 6/2005 | O'Mahony et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0143864 A1 | 6/2005 | Blomquist |
| 2005/0145010 A1 | 7/2005 | Vanderveen et al. |
| 2005/0171503 A1 | 8/2005 | Van Den Berghe et al. |
| 2005/0171815 A1 | 8/2005 | Vanderveen |
| 2005/0177045 A1 | 8/2005 | Degertekin et al. |
| 2005/0177096 A1 | 8/2005 | Bollish et al. |
| 2005/0182306 A1 | 8/2005 | Sloan |
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |
| 2005/0277890 A1 | 12/2005 | Stewart et al. |
| 2005/0279419 A1 | 12/2005 | Tribble et al. |
| 2006/0002799 A1 | 1/2006 | Schann et al. |
| 2006/0009727 A1 | 1/2006 | O'Mahony et al. |
| 2006/0009734 A1 | 1/2006 | Martin |
| 2006/0042633 A1 | 3/2006 | Bishop et al. |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0064053 A1 | 3/2006 | Bollish et al. |
| 2006/0079768 A1 | 4/2006 | Small et al. |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1 | 6/2006 | Eggers et al. |
| 2006/0135939 A1 | 6/2006 | Brown |
| 2006/0135940 A1 | 6/2006 | Joshi |
| 2006/0136095 A1 | 6/2006 | Rob et al. |
| 2006/0136271 A1 | 6/2006 | Eggers et al. |
| 2006/0140798 A1 | 6/2006 | Kutsuzawa |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0181695 A1 | 8/2006 | Sage, Jr. |
| 2006/0187069 A1 | 8/2006 | Duan |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224140 A1 | 10/2006 | Junker |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229918 A1 | 10/2006 | Fotsch et al. |
| 2006/0235353 A1 | 10/2006 | Gelfand et al. |
| 2006/0255149 A1 | 11/2006 | Retter et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2006/0276771 A1 | 12/2006 | Galley |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060869 A1 | 3/2007 | Tolle et al. |
| 2007/0060871 A1 | 3/2007 | Istoc |
| 2007/0060872 A1 | 3/2007 | Hall et al. |
| 2007/0060874 A1 | 3/2007 | Nesbitt et al. |
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1 | 4/2007 | Williams, Jr. et al. |
| 2007/0084286 A1 | 4/2007 | Ajay et al. |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0093753 A1 | 4/2007 | Krulevitcvh et al. |
| 2007/0094045 A1 | 4/2007 | Cobbs et al. |
| 2007/0094046 A1 | 4/2007 | Cobbs et al. |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0156456 A1 | 7/2007 | McGillin et al. |
| 2007/0179436 A1 | 8/2007 | Braig et al. |
| 2007/0180916 A1 | 8/2007 | Tian et al. |
| 2007/0191770 A1 | 8/2007 | Moberg et al. |
| 2007/0191817 A1 | 8/2007 | Martin |
| 2007/0197963 A1 | 8/2007 | Griffiths et al. |
| 2007/0214003 A1 | 9/2007 | Holland et al. |
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0250339 A1 | 10/2007 | Mallett et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |

(56)    References Cited

U.S. PATENT DOCUMENTS

| | | |
|---|---|---|
| 2008/0071210 A1 | 3/2008 | Moubayed et al. |
| 2008/0071496 A1 | 3/2008 | Glascock |
| 2008/0071580 A1 | 3/2008 | Marcus et al. |
| 2008/0077116 A1 | 3/2008 | Dailey et al. |
| 2008/0086087 A1 | 4/2008 | Spohn et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0169044 A1 | 7/2008 | Osborne et al. |
| 2008/0172030 A1 | 7/2008 | Blomquist et al. |
| 2008/0177126 A1 | 7/2008 | Tate et al. |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0208484 A1 | 8/2008 | Butterfield et al. |
| 2008/0214919 A1 | 9/2008 | Harmon et al. |
| 2008/0219405 A1 | 9/2008 | Falco et al. |
| 2008/0221521 A1 | 9/2008 | Getz et al. |
| 2008/0221522 A1 | 9/2008 | Moberg et al. |
| 2008/0243055 A1* | 10/2008 | Fathallah ............. A61M 5/172 |
| | | 604/65 |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0054743 A1 | 2/2009 | Stewart |
| 2009/0054754 A1 | 2/2009 | McMahon et al. |
| 2009/0062727 A1 | 3/2009 | Woo |
| 2009/0069743 A1 | 3/2009 | Krishnamoorthy et al. |
| 2009/0077248 A1 | 3/2009 | Castellucci et al. |
| 2009/0082676 A1 | 3/2009 | Bennison |
| 2009/0088731 A1 | 4/2009 | Campbell et al. |
| 2009/0097029 A1 | 4/2009 | Tokhtuev et al. |
| 2009/0099866 A1 | 4/2009 | Newman |
| 2009/0105636 A1 | 4/2009 | Hayter et al. |
| 2009/0112155 A1 | 4/2009 | Zhao |
| 2009/0114037 A1 | 5/2009 | Smith |
| 2009/0119330 A1 | 5/2009 | Sampath et al. |
| 2009/0124963 A1 | 5/2009 | Hogard et al. |
| 2009/0124964 A1 | 5/2009 | Leach et al. |
| 2009/0126825 A1 | 5/2009 | Eliuk et al. |
| 2009/0131861 A1 | 5/2009 | Braig et al. |
| 2009/0135196 A1 | 5/2009 | Holland et al. |
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0156922 A1 | 6/2009 | Goldberger et al. |
| 2009/0156975 A1 | 6/2009 | Robinson et al. |
| 2009/0177146 A1 | 7/2009 | Nesbitt et al. |
| 2009/0177188 A1 | 7/2009 | Steinkogler |
| 2009/0177248 A1 | 7/2009 | Roberts |
| 2009/0177769 A1 | 7/2009 | Roberts |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0198347 A1 | 8/2009 | Kirzinger |
| 2009/0199113 A1 | 8/2009 | McWhinnie et al. |
| 2009/0205426 A1 | 8/2009 | Balschat et al. |
| 2009/0209938 A1 | 8/2009 | Aalto-Setala |
| 2009/0209945 A1 | 8/2009 | Lobl et al. |
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Memoe et al. |
| 2009/0264720 A1 | 10/2009 | Torjman et al. |
| 2009/0270810 A1 | 10/2009 | DeBelser |
| 2009/0270833 A1 | 10/2009 | DeBelser |
| 2009/0281497 A1 | 11/2009 | Kamen et al. |
| 2009/0299156 A1 | 12/2009 | Simpson et al. |
| 2009/0315485 A1 | 12/2009 | Verfuerth et al. |
| 2010/0022988 A1 | 1/2010 | Wochner |
| 2010/0036310 A1 | 2/2010 | Hillman |
| 2010/0056992 A1 | 3/2010 | Hayter |
| 2010/0057042 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0114027 A1 | 5/2010 | Jacobson et al. |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1 | 7/2010 | Robinson et al. |
| 2010/0177375 A1 | 7/2010 | Seyfried |
| 2010/0185142 A1 | 7/2010 | Kamen et al. |
| 2010/0185182 A1 | 7/2010 | Alme et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |
| 2010/0212675 A1 | 8/2010 | Walling et al. |
| 2010/0217154 A1 | 8/2010 | Deshmukh et al. |
| 2010/0217621 A1 | 8/2010 | Schoenberg |
| 2010/0271218 A1 | 10/2010 | Hoag et al. |
| 2010/0271479 A1 | 10/2010 | Heydlauf |
| 2010/0273738 A1 | 10/2010 | Valcke et al. |
| 2010/0280430 A1 | 11/2010 | Caleffi et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0312039 A1 | 12/2010 | Quirico et al. |
| 2010/0317093 A1 | 12/2010 | Turewicz et al. |
| 2010/0317952 A1 | 12/2010 | Budiman et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0009797 A1 | 1/2011 | Kelly et al. |
| 2011/0028885 A1 | 2/2011 | Eggers et al. |
| 2011/0046558 A1 | 2/2011 | Gravesen et al. |
| 2011/0054311 A1 | 3/2011 | Williams et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0071844 A1 | 3/2011 | Cannon et al. |
| 2011/0072379 A1 | 3/2011 | Gannon |
| 2011/0077480 A1 | 3/2011 | Bloom et al. |
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0106561 A1 | 5/2011 | Eaton, Jr. et al. |
| 2011/0107251 A1 | 5/2011 | Guaitoli et al. |
| 2011/0119612 A1 | 5/2011 | Gannon et al. |
| 2011/0137241 A1 | 6/2011 | DelCastillo et al. |
| 2011/0144595 A1 | 6/2011 | Cheng |
| 2011/0152770 A1 | 6/2011 | Diperna et al. |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0184379 A1 | 7/2011 | Van Antwerp et al. |

(56)                    References Cited

U.S. PATENT DOCUMENTS

| | | |
|---|---|---|
| 2011/0190598 A1 | 8/2011 | Shusterman |
| 2011/0190694 A1 | 8/2011 | Lanier et al. |
| 2011/0218514 A1 | 9/2011 | Rebours |
| 2011/0238032 A1 | 9/2011 | McTaggart et al. |
| 2011/0241878 A1 | 10/2011 | Hoag |
| 2011/0264006 A1 | 10/2011 | Ali et al. |
| 2011/0264043 A1 | 10/2011 | Kotnick et al. |
| 2011/0282321 A1 | 11/2011 | Steil et al. |
| 2011/0313390 A1 | 12/2011 | Roy et al. |
| 2011/0319728 A1 | 12/2011 | Petisce et al. |
| 2011/0320049 A1 | 12/2011 | Chossat et al. |
| 2012/0016215 A1 | 1/2012 | Condurso et al. |
| 2012/0023431 A1 | 1/2012 | Roth |
| 2012/0025995 A1 | 2/2012 | Moberg et al. |
| 2012/0059234 A1 | 3/2012 | Barrett et al. |
| 2012/0068001 A1 | 3/2012 | Pushkarsky et al. |
| 2012/0083760 A1 | 4/2012 | Ledford et al. |
| 2012/0085277 A1 | 4/2012 | Abdel-Rahman |
| 2012/0089411 A1 | 4/2012 | Srnka et al. |
| 2012/0095433 A1 | 4/2012 | Hungerford et al. |
| 2012/0116195 A1 | 5/2012 | Chaum et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0222774 A1 | 9/2012 | Husnu et al. |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2012/0310204 A1 | 12/2012 | Krogh et al. |
| 2012/0323212 A1 | 12/2012 | Murphy |
| 2013/0006666 A1 | 1/2013 | Schneider |
| 2013/0009551 A1 | 1/2013 | Knapp |
| 2013/0012880 A1 | 1/2013 | Blomquist |
| 2013/0012917 A1 | 1/2013 | Miller et al. |
| 2013/0032634 A1 | 2/2013 | McKirdy |
| 2013/0041342 A1 | 2/2013 | Bernini et al. |
| 2013/0044111 A1 | 2/2013 | VanGilder et al. |
| 2013/0085778 A1 | 4/2013 | Guertin et al. |
| 2013/0110538 A1 | 5/2013 | Butterfield et al. |
| 2013/0116649 A1 | 5/2013 | Breton et al. |
| 2013/0150766 A1 | 6/2013 | Olde et al. |
| 2013/0150821 A1 | 6/2013 | Bollish et al. |
| 2013/0173291 A1 | 7/2013 | Kelly |
| 2013/0177455 A1 | 7/2013 | Kamen et al. |
| 2013/0184676 A1 | 7/2013 | Kamen et al. |
| 2013/0197930 A1 | 8/2013 | Garibaldi et al. |
| 2013/0201482 A1 | 8/2013 | Munro |
| 2013/0214040 A1 | 8/2013 | Beerling et al. |
| 2013/0218080 A1 | 8/2013 | Peterfreund et al. |
| 2013/0253430 A1 | 9/2013 | Kouyoumjian et al. |
| 2013/0253946 A1 | 9/2013 | Broselow |
| 2013/0274576 A1 | 10/2013 | Amirouche et al. |
| 2013/0281965 A1 | 10/2013 | Kamen et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1 | 11/2013 | Teng et al. |
| 2013/0322201 A1 | 12/2013 | Hitchcock et al. |
| 2013/0345658 A1 | 12/2013 | Browne et al. |
| 2013/0345666 A1 | 12/2013 | Panduro et al. |
| 2014/0067425 A1 | 3/2014 | Dudar et al. |
| 2014/0132524 A1 | 5/2014 | Lee |
| 2014/0145915 A1 | 5/2014 | Ribble et al. |
| 2014/0180711 A1 | 6/2014 | Kamen et al. |
| 2014/0224829 A1 | 8/2014 | Capone et al. |
| 2014/0249500 A1 | 9/2014 | Estes et al. |
| 2014/0267563 A1 | 9/2014 | Baca et al. |
| 2014/0303754 A1 | 10/2014 | Nixon et al. |
| 2015/0025453 A1 | 1/2015 | Ledford et al. |
| 2015/0033073 A1 | 1/2015 | Yang et al. |
| 2015/0051458 A1 | 2/2015 | Chen |
| 2015/0057108 A1 | 2/2015 | Regimbal |
| 2015/0065988 A1 | 3/2015 | Holderle et al. |
| 2015/0089439 A1 | 3/2015 | Wada |
| 2015/0114515 A1 | 4/2015 | Phallen |
| 2015/0141921 A1 | 5/2015 | Stewart et al. |
| 2015/0168958 A1 | 6/2015 | Downie et al. |
| 2015/0265765 A1 | 9/2015 | Yavorsky et al. |
| 2015/0278474 A1 | 10/2015 | Stueckemann |
| 2015/0289823 A1 | 10/2015 | Rack-Gomer et al. |
| 2015/0324544 A1 | 11/2015 | Maslowski et al. |
| 2015/0338340 A1 | 11/2015 | Jiang et al. |
| 2015/0363086 A1 | 12/2015 | Lim |
| 2015/0371004 A1 | 12/2015 | Jones |
| 2016/0000998 A1 | 1/2016 | Estes |
| 2016/0019352 A1 | 1/2016 | Seo |
| 2016/0042264 A1 | 2/2016 | Borges et al. |
| 2016/0051750 A1 | 2/2016 | Tsoukalis |
| 2016/0110088 A1 | 4/2016 | Vik et al. |
| 2016/0144101 A1 | 5/2016 | Pananen |
| 2016/0151560 A1 | 6/2016 | Toro et al. |
| 2016/0151562 A1 | 6/2016 | Magers et al. |
| 2016/0151601 A1 | 6/2016 | Cardelius et al. |
| 2016/0158437 A1 | 6/2016 | Biasi et al. |
| 2016/0193604 A1 | 7/2016 | McFarland et al. |
| 2016/0253460 A1 | 9/2016 | Kanada |
| 2016/0300425 A1 | 10/2016 | Devaraj et al. |
| 2016/0339167 A1 | 11/2016 | Ledford et al. |
| 2017/0010677 A1 | 1/2017 | Roh |
| 2017/0043089 A1 | 2/2017 | Handler |
| 2017/0056604 A1 | 3/2017 | Cowan |
| 2017/0068498 A1 | 3/2017 | Hashem |
| 2017/0132867 A1 | 5/2017 | Berg et al. |
| 2017/0354941 A1 | 12/2017 | Brown et al. |
| 2018/0008787 A1 | 1/2018 | Schriver et al. |
| 2018/0018440 A1 | 1/2018 | Sugawara |
| 2018/0021514 A1 | 1/2018 | Rosinko et al. |
| 2018/0206798 A1 | 7/2018 | Murai |
| 2018/0214636 A1 | 8/2018 | Amirouche |
| 2018/0296751 A1 | 10/2018 | Lefort et al. |
| 2018/0300994 A1 | 10/2018 | Nelson et al. |
| 2018/0326146 A1 | 11/2018 | Gupta et al. |
| 2019/0072405 A1 | 3/2019 | Luchner |
| 2019/0111209 A1 | 4/2019 | Murphy et al. |
| 2019/0160254 A1 | 5/2019 | Anand |
| 2019/0201607 A1 | 7/2019 | Öberg |
| 2019/0282757 A1 | 9/2019 | Gylland et al. |
| 2019/0351131 A1 | 11/2019 | Butterfield et al. |
| 2020/0054825 A1 | 2/2020 | Kamen et al. |
| 2020/0113784 A1 | 4/2020 | Lopez et al. |
| 2020/0147303 A1 | 5/2020 | Lee |
| 2020/0238007 A1 | 7/2020 | Day |
| 2020/0273013 A1 | 8/2020 | Garner |
| 2020/0330689 A1 | 10/2020 | Nemoto et al. |
| 2020/0353163 A1 | 11/2020 | Hand |
| 2020/0384191 A1 | 12/2020 | Rosinko et al. |
| 2021/0041994 A1 | 2/2021 | Yamamoto |
| 2021/0049555 A1 | 2/2021 | Shor |
| 2021/0146035 A1 | 5/2021 | Tsoukalis |
| 2021/0158481 A1 | 5/2021 | Wang |
| 2021/0158946 A1 | 5/2021 | Starobinets et al. |
| 2021/0162115 A1 | 6/2021 | Surine |
| 2021/0170101 A1 | 6/2021 | Cavendish, Jr. et al. |
| 2021/0260283 A1 | 8/2021 | Oruklu et al. |
| 2021/0295263 A1 | 9/2021 | Hume et al. |
| 2021/0304864 A1 | 9/2021 | Kamen et al. |
| 2021/0397396 A1 | 12/2021 | Fryman |
| 2022/0031943 A1 | 2/2022 | Dumas, III |
| 2022/0088305 A1 | 3/2022 | Cavendish, Jr. |
| 2022/0176037 A1 | 6/2022 | Jacobson et al. |
| 2022/0184302 A1 | 6/2022 | Cavendish, Jr. et al. |
| 2022/0184304 A1 | 6/2022 | Rinehart |
| 2022/0296806 A1 | 9/2022 | Shubinsky et al. |
| 2022/0305200 A1 | 9/2022 | Gylland et al. |
| 2022/0331518 A1 | 10/2022 | Shubinsky et al. |
| 2022/0362463 A1 | 11/2022 | Lindo et al. |
| 2022/0391940 A1 | 12/2022 | Tietzen et al. |
| 2022/0401640 A1 | 12/2022 | Jacobson |
| 2023/0010290 A1 | 1/2023 | Oruklu et al. |
| 2023/0010638 A1 | 1/2023 | Rubalcaba, Jr. et al. |

(56)                References Cited

U.S. PATENT DOCUMENTS

2023/0017117 A1     1/2023   Sileika et al.
2023/0058662 A1     2/2023   Ruchti et al.
2023/0112979 A1     4/2023   Xavier
2023/0181419 A1     6/2023   Fister
2023/0245741 A1     8/2023   Shigyo
2023/0285669 A1     9/2023   Day
2023/0310735 A1     10/2023  Cousineau
2024/0201922 A1     6/2024   Fryman
2024/0263981 A1     8/2024   Ruchti et al.
2024/0325246 A1     10/2024  Janssen
2024/0366858 A1     11/2024  Cousineau et al.
2024/0386433 A1     11/2024  Shah et al.
2025/0285747 A1     9/2025   Burgess

FOREIGN PATENT DOCUMENTS

CA   2 113 473            3/1993
CA   2 551 817            7/2005
CA   2 554 407            8/2005
CN   201061636           5/2008
CN   105682703           6/2016
CN   107106042           8/2017
CN   110573195           12/2019
CN   105848694           1/2020
CN   111954966           11/2020
CN   306893275           10/2021
CN   307412164           6/2022
CN   307979072           4/2023
CN   112105405           8/2023
CN   308499458           3/2024
CO   0020220004676-0001  11/2022
CO   0020220008155-0001  11/2022
DE   31 12 762           1/1983
DE   34 35 647           7/1985
DE   35 30 747           3/1987
DE   37 20 664           1/1989
DE   38 27 444           2/1990
DE   197 34 002          9/1998
DE   199 01 078          2/2000
DE   198 40 965          3/2000
DE   198 44 252          3/2000
DE   199 32 147          1/2001
DE   102 49 238          5/2004
DE   103 52 456          7/2005
EP   0 282 323           9/1988
EP   0 291 727           11/1988
EP   0 319 272           6/1989
EP   0 319 275           6/1989
EP   0 335 385           10/1989
EP   0 337 092           10/1989
EP   0 341 582           11/1989
EP   0 370 162           5/1990
EP   0 387 724           9/1990
EP   0 429 866           6/1991
EP   0 441 323           8/1991
EP   0 453 211           10/1991
EP   0 462 405           12/1991
EP   0 501 234           9/1992
EP   0 516 130           12/1992
EP   0 519 765           12/1992
EP   0 643 301           3/1995
EP   0 683 465           11/1995
EP   0 431 310           1/1996
EP   0 589 439           8/1998
EP   0 880 936           12/1998
EP   0 954 090           11/1999
EP   0 960 627           12/1999
EP   1 174 817           1/2002
EP   1 177 802           2/2002
EP   1 197 178           4/2002
EP   1 500 025           4/2003
EP   1 813 188           8/2007
EP   1 490 131           12/2007
EP   2 062 527           5/2009
EP   2 228 004           9/2010
EP   2 243 506           10/2010
EP   2 381 260           10/2011
EP   3 171 287           5/2017
EP   008932172-0003      4/2022
EP   008932172-0004      4/2022
ES   254513              10/1981
FR   2 717 919           9/1995
GB   2 121 971           1/1984
GB   2 303 706           2/1997
GB   2 312 022           10/1997
GB   2 312 046           10/1997
GB   6 201 192           4/2022
GB   6 201 193           4/2022
JP   01-301118           12/1989
JP   01-308568           12/1989
JP   04-231966           8/1992
JP   07-502678           3/1995
JP   07-289638           11/1995
JP   11-128344           5/1999
JP   2000-111374         4/2000
JP   2000-510575         8/2000
JP   2000-515716         11/2000
JP   2001-356034         12/2001
JP   2002-506514         2/2002
JP   2002-131105         5/2002
JP   2003-038642         2/2003
JP   2003-050144         2/2003
JP   2005-021463         1/2005
JP   2005-524081         3/2005
JP   2006-517423         7/2006
JP   2007-071695         3/2007
JP   2007-518471         7/2007
JP   2007-520270         7/2007
JP   2007-275106         10/2007
JP   2008-249400         10/2008
JP   4322661             6/2009
JP   2009-148592         7/2009
JP   2010-063767         3/2010
JP   5716879             3/2015
JP   6446030             12/2018
JP   2020-533111         11/2020
TW   201841165           11/2018
WO   WO 84/000690        3/1984
WO   WO 84/000894        3/1984
WO   WO 90/007942        7/1990
WO   WO 91/000113        1/1991
WO   WO 91/016087        10/1991
WO   WO 91/016416        10/1991
WO   WO 93/004284        3/1993
WO   WO 95/016200        6/1995
WO   WO 95/031233        11/1995
WO   WO 96/008755        3/1996
WO   WO 96/025186        8/1996
WO   WO 96/028209        9/1996
WO   WO 96/041156        12/1996
WO   WO 97/010013        3/1997
WO   WO 97/030333        8/1997
WO   WO 98/004304        2/1998
WO   WO 98/012670        3/1998
WO   WO 98/014234        4/1998
WO   WO 98/019263        5/1998
WO   WO 98/044320        10/1998
WO   WO 98/056441        12/1998
WO   WO 99/010029        3/1999
WO   WO 99/015216        4/1999
WO   WO 99/051003        10/1999
WO   WO 99/052575        10/1999
WO   WO 00/013580        3/2000
WO   WO 00/013726        3/2000
WO   WO 00/041621        7/2000
WO   WO 01/014974        3/2001
WO   WO 01/033484        5/2001
WO   WO 02/005702        1/2002
WO   WO 02/009795        2/2002
WO   WO 02/027276        4/2002
WO   WO 02/066101        8/2002
WO   WO 02/087664        11/2002
WO   WO 03/006091        1/2003
WO   WO 03/053498        7/2003

(56) References Cited

FOREIGN PATENT DOCUMENTS

| | | |
|---|---|---|
| WO | WO 03/093780 | 11/2003 |
| WO | WO 2004/035115 | 4/2004 |
| WO | WO 2004/060455 | 7/2004 |
| WO | WO 2004/061745 | 7/2004 |
| WO | WO 2004/070556 | 8/2004 |
| WO | WO 2004/070994 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2006/026270 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2009/141504 | 11/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2012/082599 | 6/2012 |
| WO | WO 2012/108910 | 8/2012 |
| WO | WO 2012/167090 | 12/2012 |
| WO | WO 2013/036854 | 3/2013 |
| WO | WO 2013/096769 | 6/2013 |
| WO | WO 2015/134478 | 9/2015 |
| WO | WO 2016/160321 | 10/2016 |
| WO | WO 2017/051271 | 3/2017 |
| WO | WO 2017/087157 | 5/2017 |
| WO | WO 2017/144366 | 8/2017 |
| WO | WO 2019/055516 | 3/2019 |
| WO | WO 2019/063462 | 4/2019 |
| WO | WO 2019/092680 | 5/2019 |
| WO | WO 2020/214717 | 10/2020 |
| WO | WO 2022/020184 | 1/2022 |
| WO | WO 2022/072159 | 4/2022 |
| WO | WO 2022/125471 | 6/2022 |
| WO | WO 2022/140204 | 6/2022 |
| WO | WO 2023/064662 | 4/2023 |
| WO | WO 2023/108030 | 6/2023 |
| WO | WO 2023/192791 | 10/2023 |
| WO | WO 2023/244922 | 12/2023 |

OTHER PUBLICATIONS

Alaedeen et al., "Total Parenteral Nutrition-Associated Hypergly-cemia Correlates with Prolonged Mechanical Ventilation and Hospital Stay in Septic Infants", Journal of Pediatric Surgery, Jan. 2006, vol. 41, No. 1, pp. 239-244.

ALARIS® Medical Systems, "Signature Edition® GOLD—Single & Dual Channel Infusion System", San Diego, CA, USA, date unknown, but believed to be at least as early as Nov. 29, 2008, pp. 2-88 & 2-91.

Allegro, "3955—Full-Bridge PWM Microstepping Motor Drive", Datasheet, 1997, pp. 16.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

Baxter, "Baxter Receives 510(k) Clearance for Next-Generation SIGMA Spectrum Infusion Pump with Master Drug Library" Press Release, May 8, 2014, pp. 2. <http://web.archive.org/web/20160403140025/http://www.baxter.com/news-media/newsroom/press-releases/2014/05_08_14_sigma.page>.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.

Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.

Buhrdorf et al., "Capacitive Micromachined Ultrasonic Transducers and their Application", Proceedings of the IEEE Ultrasonics Symposium, Feb. 2001, vol. 2, pp. 933-940.

Cannon, MD et al., "Automated Heparin-Delivery System to Control Activated Partial Thromboplastin Time", Circulation, Feb. 16, 1999, vol. 99, pp. 751-756.

"CareAware® Infusion Management", Cerner Store, as printed May 12, 2011, pp. 3, <https://store.cerner.com/items/7>.

Chen et al., "Enabling Location-Based Services on Wireless LANs", The 11th IEEE International Conference on Networks, ICON 2003, Sep. 28-Oct. 1, 2003, pp. 567-572.

Cheung et al., "Hyperglycemia is Associated with Adverse Outcomes in Patients Receiving Total Parenteral Nutrition", Diabetes Care, Oct. 2005, vol. 28, No. 10, pp. 2367-2371.

Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.

"Continually vs Continuously", <https://web.archive.org/web/20090813092423/http://www.diffen.com/difference/Continually_vs_Continuously>, as accessed Aug. 13, 2009 in 4 pages.

"CritiCore® Monitor: Critical Fluid Output and Core Bladder Temperature Monitor", BARD Urological Catheter Systems, Advertisement, 2005, pp. 2.

Daimiwal et al., "Wireless Transfusion Supervision and Analysis Using Embedded System", IEEE, 2010 International Conference ICBBT, China, Apr. 2010, pp. 56-60.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.

"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. <http://archive.epo.org/epo/pubs/oj013/11_13/11_5033.pdf>.

(56)                 References Cited

OTHER PUBLICATIONS

"Decision of the Administrative Council of Oct. 27, 2009 Amending the Implementing Regulations to the European Patent Convention (CA/D 20/09)", Official Journal EPO Dec. 2009, Dec. 2009, pp. 582-584. <http://archive.epo.org/epo/pubs/oj009/12_09/12_5829.pdf>.

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

"Differential Pressure Transmitter, Series PD-39 X", SensorsOne Ltd., Advertisement, Dec. 2005, pp. 2.

Dunster et al., "Flow Continuity of Infusion Systems at Low Flow Rates", Anaesthesia and Intensive Care, Oct. 1995, vol. 23, No. 5, pp. 5.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.

"Froth", <http://www.merriam-webster.com/dictionary/froth>, as accessed May 13, 2015 in 1 page.

Goldberg et al., "Clinical Results of an Updated Insulin Infusion Protocol in Critically Ill Patients", Diabetes Spectrum, 2005, vol. 18, No. 3, pp. 188-191.

Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.

Hospira, "Plum A+™ Infusion System" as archived Dec. 1, 2012, pp. 2. <www.hospira.com/products_and_services/infusion_pumps/plum/index>.

Hospira, "Plum XL™ Series Infusion System" Technical Service Manual, Feb. 2005, Lake Forest, Illinois, USA, pp. i-vii, 5-14, 8-3.

Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.

Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.

JMS Co., Ltd., "Infusion Pump: OT-701", Tokyo, Japan, 2002, pp. 4.

Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.

Kutcher et al., "The Effect of Lighting Conditions on Caries Interpretation with a Laptop Computer in a Clinical Setting", Elsevier, Oct. 2006, vol. 102, No. 4, pp. 537-543.

Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.

Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.

Magaji et al., "Inpatient Management of Hyperglycemia and Diabetes", Clinical Diabetes, 2011, vol. 29, No. 1, pp. 3-9.

Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.

Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.

Merry et al., "A New, Safety-Oriented, Integrated Drug Administration and Automated Anesthesia Record System", Anesthesia & Analgesia, Aug. 2001, vol. 93, No. 2 pp. 385-390.

Microchip Technology Inc., "MTA11200B; TrueGauge™ Intelligent Battery Management I.C.", <https://www.elektronik.ropla.eu/pdf/stock/mcp/mta11200b.pdf>, 1995, pp. 44.

Moghissi, Etie, MD, FACP, FACE, "Hyperglycemia in Hospitalized Patients", A Supplement to ACP Hospitalist, Jun. 15, 2008, pp. 32.

Nuckols et al., "Programmable Infusion Pumps in ICUs: An Analysis of Corresponding Adverse Drug Events", Journal of General Internal Medicine, 2007, vol. 23, Supp. 1, pp. 41-45.

Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.

Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.

Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.

SGS-Thomson Microelectronics, "L6219—Stepper Motor Drive", Datasheet, Dec. 1996, pp. 10.

SGS-Thomson Microelectronics, "PBL3717A—Stepper Motor Drive", Datasheet, Apr. 1993, pp. 11.

Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.

Smith, Joe, "Infusion Pump Informatics", CatalyzeCare: Transforming Healthcare, as printed May 12, 2011, pp. 2.

Tang et al., "Linear Dimensionality Reduction Using Relevance Weighted LDA", Pattern Recognition, 2005, vol. 38, pp. 485-493, <http://staff.ustc.edu.cn/~ketang/papers/TangSuganYaoQin_PR04.pdf>.

Thomas et al., "Implementation of a Tight Glycaemic Control Protocol Using a Web-Based Insulin Dose Calculator", Anaesthesia, 2005, vol. 60, pp. 1093-1100.

Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.

Van Den Berghe, M.D., Ph.D., et al., "Intensive Insulin Therapy in the Medical ICU", The New England Journal of Medicine, Feb. 2, 2006, vol. 354, No. 5, pp. 449-461.

Westbrook et al., "Errors in the Administration of Intravenous Medications in Hospital and the Role of Correct Procedures and Nurse Experience", BMJ Quality & Safety, 2011, vol. 20, pp. 1027-1034.

Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

Amazon, Post-it Message "Sign Here" Flags, 30/Dispenser, 4 Dispensers/Pack, Published Sep. 29, 2016, https://www.amazon.com/Assorted-Color-Colors-Dispenser-MMM684SH/dp/B00006JNMN/?th=1, * pages.

File:Soldado, Raso Fuerza Aerea Boliviana.jpg, Feb. 9, 2021, https://commons.m.wikimedia.org/wiki/File:Soldado_Raso_Fuerza_A%C3%A9rea_Boliviana.jpg, 1 page.

Fresenius, "Infusion Workstation: Orchestra® Base Intensive", Operator's Guide, Jun. 20, 2006, pp. 24. <https://manualmachine.com/fresenius/orchestrabaseunit/7455278-user-manual/>.

"ICU Medical Receives FDA Clearance for New Infusion Pump", Medical Design & Development Staff, Aug. 29, 2023, https://www.medicaldesigndevelopment.com/topics/devices/news/22871498/icu-medical-receives-fda-clearance-for-new-infusion-pump. 2 pages.

Junda, Lin, "Global development trends of green bonds", Jul. 10, 2018, pp. 9.

Notice of Opposition in European Patent Application No. 16759381.3 (Patent No. EP3285827), dated May 31, 2023 in 48 pages.

Response to Notice of Opposition in European Patent Application No. 16759381.3 (Patent No. EP3285827), dated Oct. 23, 2023 in 63 pages.

(56)                  References Cited

OTHER PUBLICATIONS

Response from the Opposer to patentee's submission in European Patent Application No. 16759381.3 (Patent No. EP3285827), dated Apr. 25, 2024 in 56 pages.

Summons to attend oral proceedings and preliminary opinion of Opposition Division submission in European Patent Application No. 16759381.3 (Patent No. EP3285827), dated May 23, 2024 in 18 pages.

International Search Report and Written Opinion received in PCT Application No. PCT/US2022/076539, dated Jan. 4, 2023 in 20 pages.

International Preliminary Report on Patentability and Written Opinion received in PCT/US2022/076539, dated Apr. 25, 2024 in 10 pages.

U.S. Appl. No. 18/776,838, filed Jul. 18, 2024, Intravenous Infusion Puivip With Display Screen Having Multiple Machine-Readable Codes for Multiple Pump Drivers.

Jusko: Moving from Basic Toward Systems Pharmacodynamic Models; Department of Pharmaceutical Sciences, School of Pharmacy and Pharmaceutical Sciences, State University of New York at Buffalo, Buffalo, New York 14214; Journal of Pharmaceutical Sciences, vol. 102, No. 9, Sep. 2013; DOI 10.1002/jps; in 11 pages.

Lesson 1: Introduction to Pharmacokinetics and Pharmacodynamics; Concepts in Clinical Pharmacokinetics; in 18 pages.

Meibohm, et al; Basic Concepts of Pharmacokinetic/pharmacodynamic (PK/PD) modelling; Department of Pharmaceutics, College of Pharmacy, University of Florida, Gainesville, FL, USA, International Journal of Clinical Pharmacology and Therapeutics, vol. 35, No. Oct. 1997 (401-413); 13 pages.

Safer Care Victoria: Dobutamine | Safer Care Victoria; https://www.safercare.vic.gov.au/clinical-guidance/critical/dobutamine; in 9 pages.

Safer Care Victoria: Dopamine | Safer Care Victoria; https://www.safercare.vic.gov.au/clinical-guidance/critical/dopamine; in 9 pages.

Safer Care Victoria: Adrenaline (epinephrine) | Safer Care Victoria; https://www.safercare.vic.gov.au/clinical-guidance/critical/adrenaline-epinephrine; in 9 pages.

Safer Care Victoria: Isoprenaline | Safer Care Victoria; https://www.safercare.vic.gov.au/clinical-guidance/critical/isoprenaline; in 8 pages.

Safer Care Victoria: Noradrenaline (norepinephrine) | Safer Care Victoria; https://www.safercare.vic.gov.au/clinical-guidance/critical/noradrenaline-norepinephrine; in 8 pages.

The heart.org Medscape: nitroglycerin IV (Rx); glyceryl trinitrate IV, IV Nitroglycerin (nitroglycerin IV) dosing, indication, interaction, adverse effects, and more; https://reference.medscape.com/drug/glyceryl-trinitrate-iv-iv-nitroglycerin-nitroglycerin-iv-342278#10; 1 page.

Me.math, Tikz: Arrow tip overlaps with node, Publication Date May 13, 2022, Retrieved Date Jul. 8, 2025, Retrieved from Internet, https://tex.stackexchange.com/questions/644097/tikz-arrow-tip-overlaps-with-node, pp. 2.

Panasonic, Reference Manual Personal Computer Model No. CF-31 Series, 2010, Panasonic Corporation, PCE0301A_XP/7, pp. 129.

Sony, Bloggie Handbook Mobile HD Snap Camera M HS-FS 1/FS 1 k/FS2/FS2k, 2011, Sony Corporation 4-275-040-12(1), pp. 80.

Sony, Sony Camera and Camcorder Battery Information, 2010, sony.com via Wayback Machine, Article ID: S1Q0399, https://web.archive.org/web/20210126195509/https://www.sony.com/electronics/support/dvd-camcorders-dcr-dvd-series/dcr-dvd101/articles/S1Q0399, pp. 3.

* cited by examiner

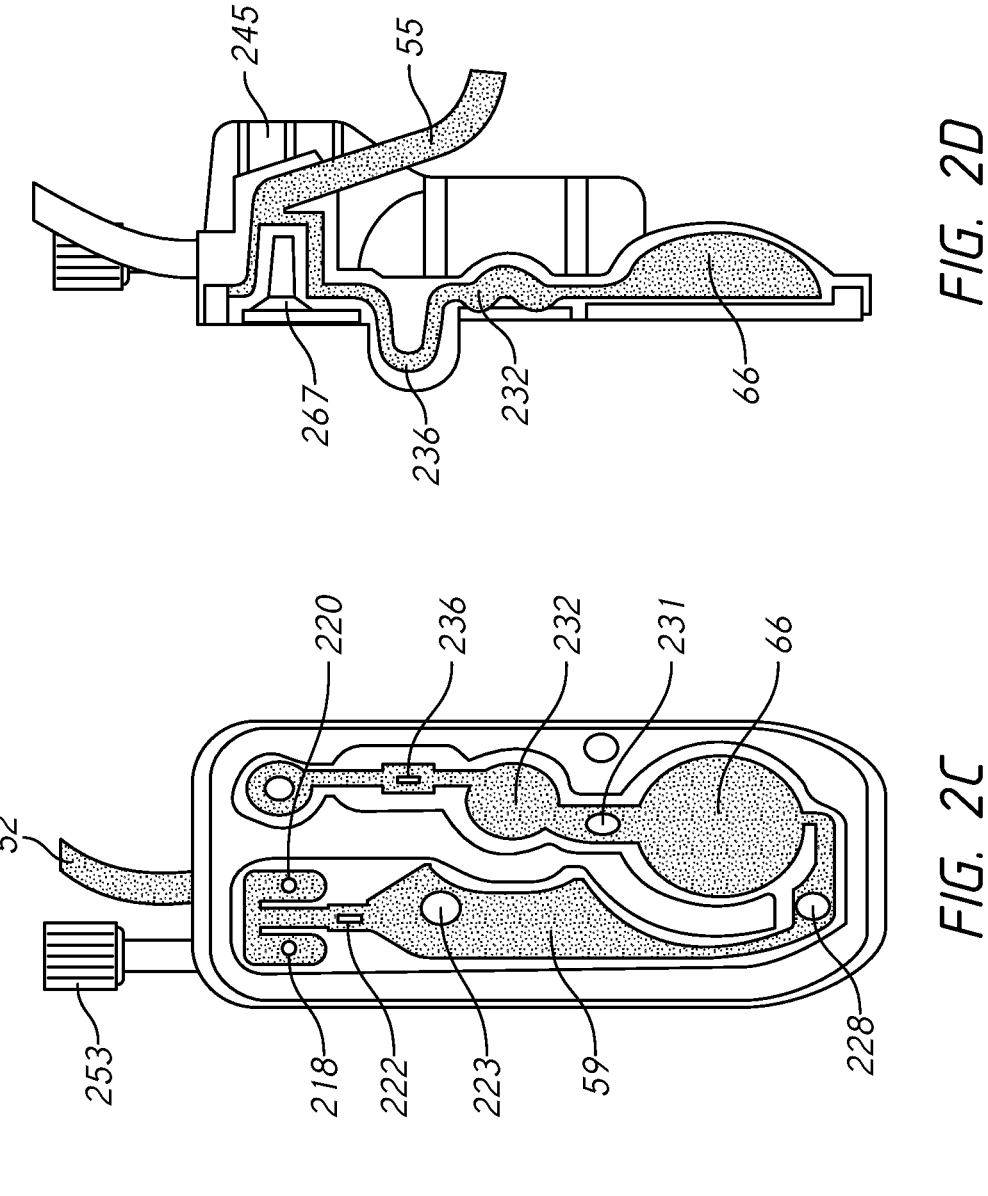
*FIG. 2D*
*FIG. 2C*
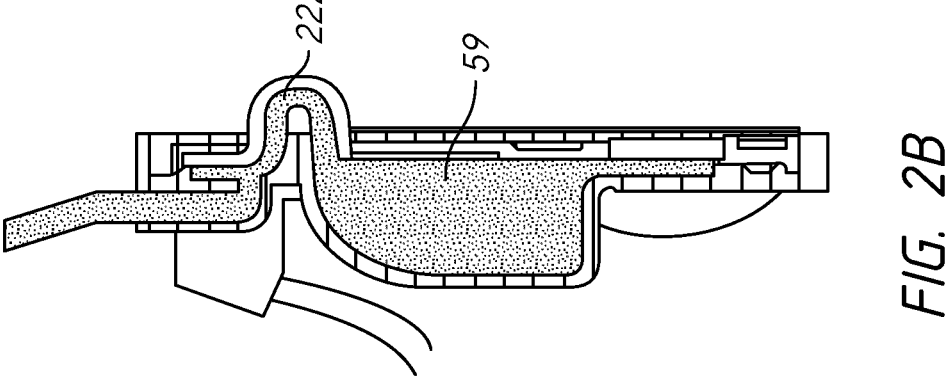
*FIG. 2B*

INTRAVENOUS INFUSION PUMP WITH CASSETTE INSERTION AND PUMP CONTROL USER INTERFACE

RELATED APPLICATIONS

This application claims the benefit under 35 U.S.C. § 119(e) of U.S. Provisional Patent Application No. 63/254,922, filed on Oct. 12, 2021, and entitled, "INTRAVENOUS INFUSION PUMP WITH CASSETTE INSERTION AND PUMP CONTROL USER INTERFACE," the entire contents of are hereby incorporated by reference herein and made a part of this specification for all that it discloses.

BACKGROUND

Field

This disclosure relates to intravenous infusion pumps, including electronically controlled intravenous infusion pumps.

Related Art

Patients all over the world who are in need of medical care commonly receive intravenous infusion therapy, especially during surgery or when hospitalized. This process generally involves inserting a needle into a patient's blood vessel, usually in the hand or arm, and then coupling the needle to a catheter in communication with one or more different types of therapeutic fluids. Once connected, the fluid travels from the fluid source(s), through the catheter, and into the patient. The fluid can provide certain desired benefits to the patient, such as maintaining hydration or nourishment, diminishing infection, reducing pain, lowing the risk of blood clots, maintaining blood pressure, providing chemotherapy, and/or delivering any other suitable drug or other therapeutic liquid to the patient. Electronic infusion pumps in communication with the fluid sources and the patient can help to increase the accuracy and consistency of fluid delivery to patients, but current electronic infusion pumps have disadvantages.

SUMMARY

In some embodiments, an electronic intravenous infusion pump is provided with a disposable, insertable pump cartridge that is connected to one or more intravenous fluid infusion sources, wherein a user interface on a user communicator of the pump (such as a display/input device) interacts with and responds to the user's insertion of the cassette.

In some implementations, a medical infusion pump system can include an electronic processor with an electronic memory; an electrical power cable or battery; an electromechanical pump driver configured to receive a disposable fluid holder and to pump medical fluid through the fluid holder; and an electronic display. The pump driver can generate a signal indicating whether the fluid holder has been received by the pump driver. The electronic processor can be configured to retrieve from the electronic memory and show on the electronic display one or more repeating moving graphics or animations with a representation of the fluid holder being inserted into the pump, until the processor confirms that the fluid holder has been received by the pump in response to the signal generated by the pump driver.

In some implementations, A medical infusion pump system can include an electronic processor with an electronic memory; an electrical power cable or battery; an electromechanical pump driver configured to receive at least one disposable fluid holder and to pump medical fluid through the fluid holder, the at least one fluid holder being connectable to one or more fluid lines from one or more fluid source containers; and an electronic display comprising a sensing region configured to detect a user's touch selection. The electronic processor can be configured to retrieve from the electronic memory and show on the electronic display a graphic that includes a representation of the least one fluid holder and a correlation between the at least one fluid holder and the sensing region.

In some implementations, a medical infusion pump system can include an electronic processor with an electronic memory; an electrical power cable or battery; an electromechanical pump driver configured to receive at least one disposable fluid holder and to pump medical fluid through the fluid holder; and an electronic display comprising a sensing region configured to detect a user's touch selection. The fluid holder can be connectable to one or more fluid lines from one or more fluid source containers. The display can be configured to permit a user to input multiple pumping stages comprising one or more different pumping parameters to be performed sequentially automatically by the pump. The display can be configured to show multiple representations of the pumping stages simultaneously on the display.

BRIEF DESCRIPTION OF THE DRAWINGS

The following drawings and the associated descriptions are provided to illustrate embodiments of the present disclosure and do not limit the scope of the claims.

FIGS. 2B-2D shows an example of a cassette that is the same as or similar to the cassette of FIG. 2A that can be used with the pump of FIG. 1.

DETAILED DESCRIPTION

Figure 1A:
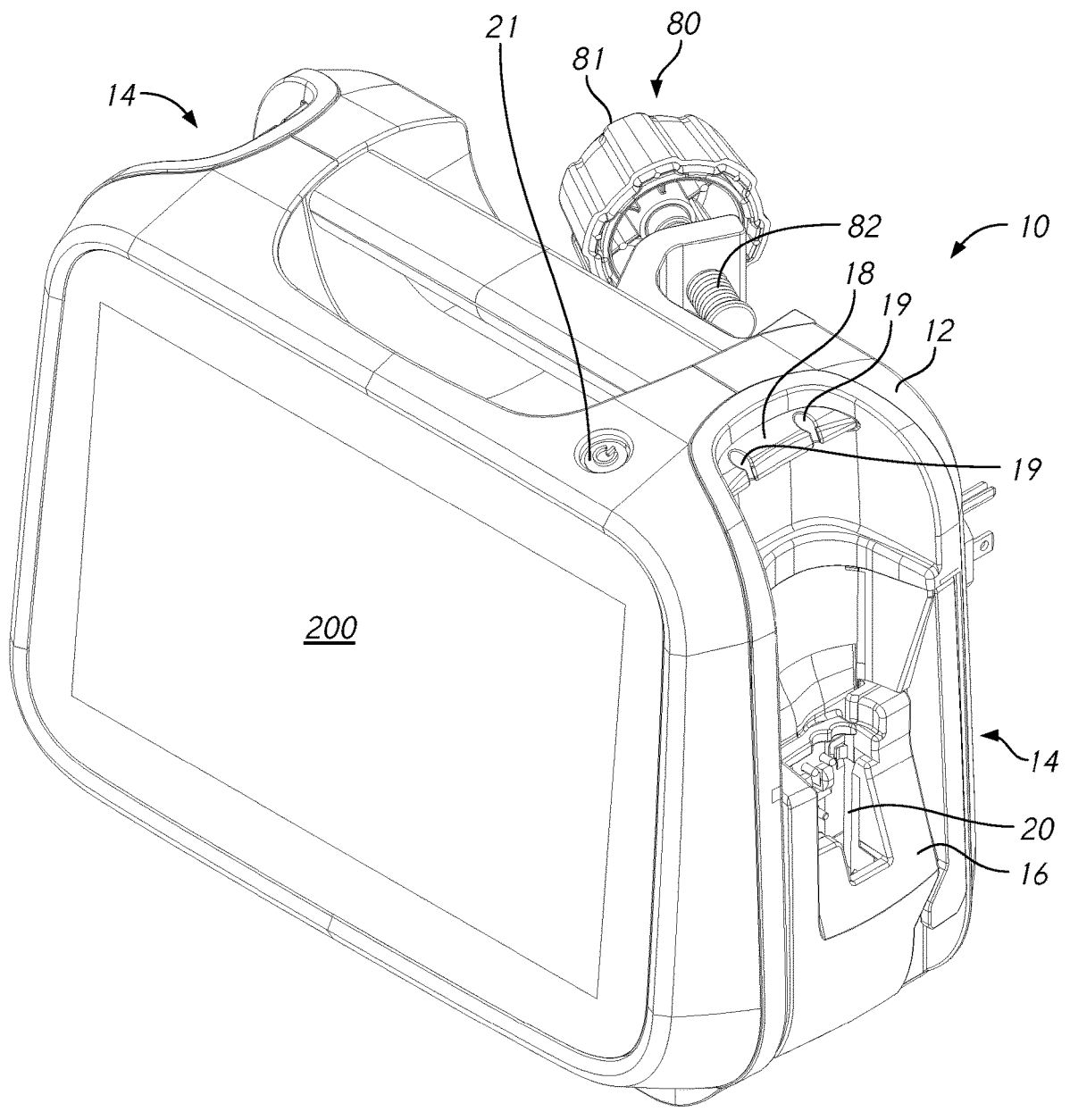
FIGS. 1A-E show front perspective, front elevational, rear elevational, top plan, and side elevational views, respectively, of an example of an infusion pump.
Figure 1B:
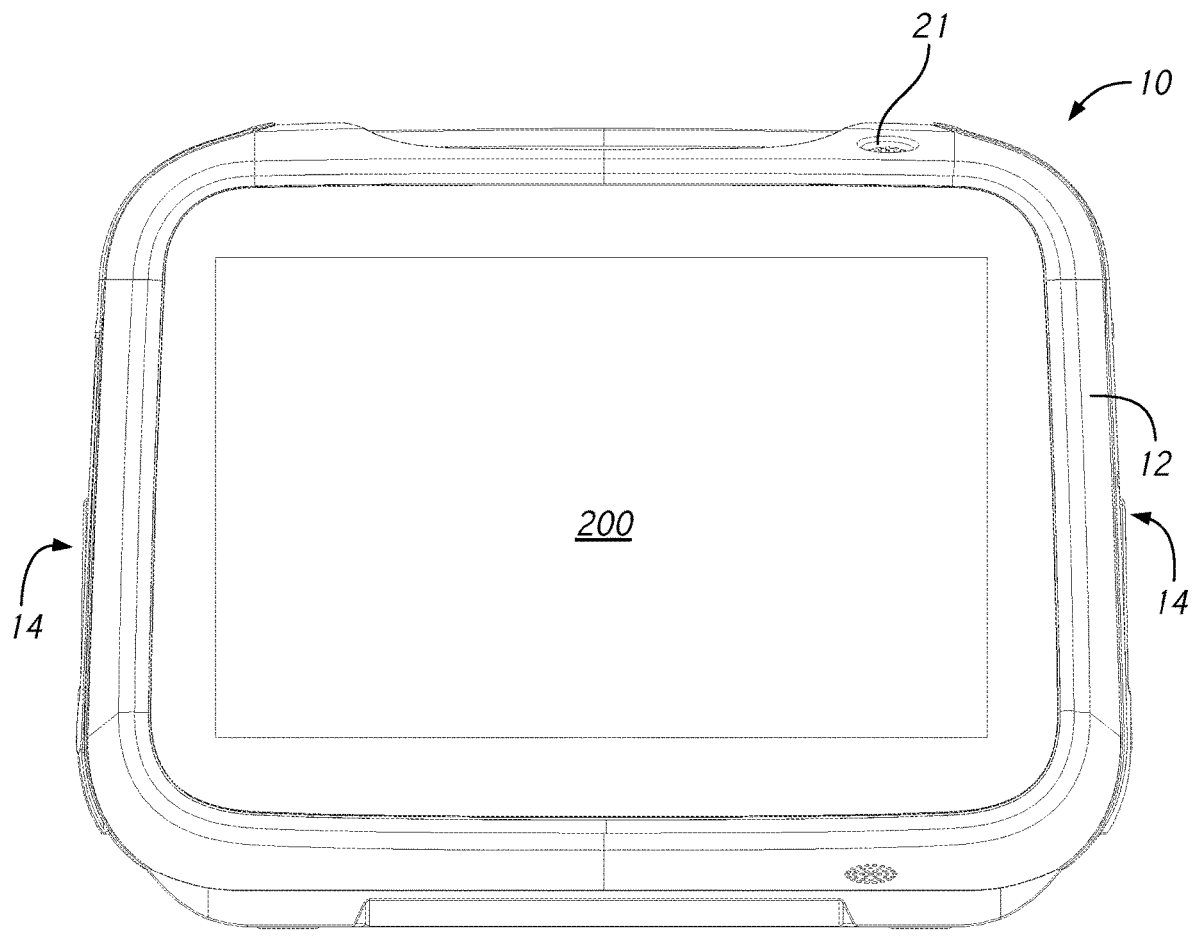
Figure 1C:
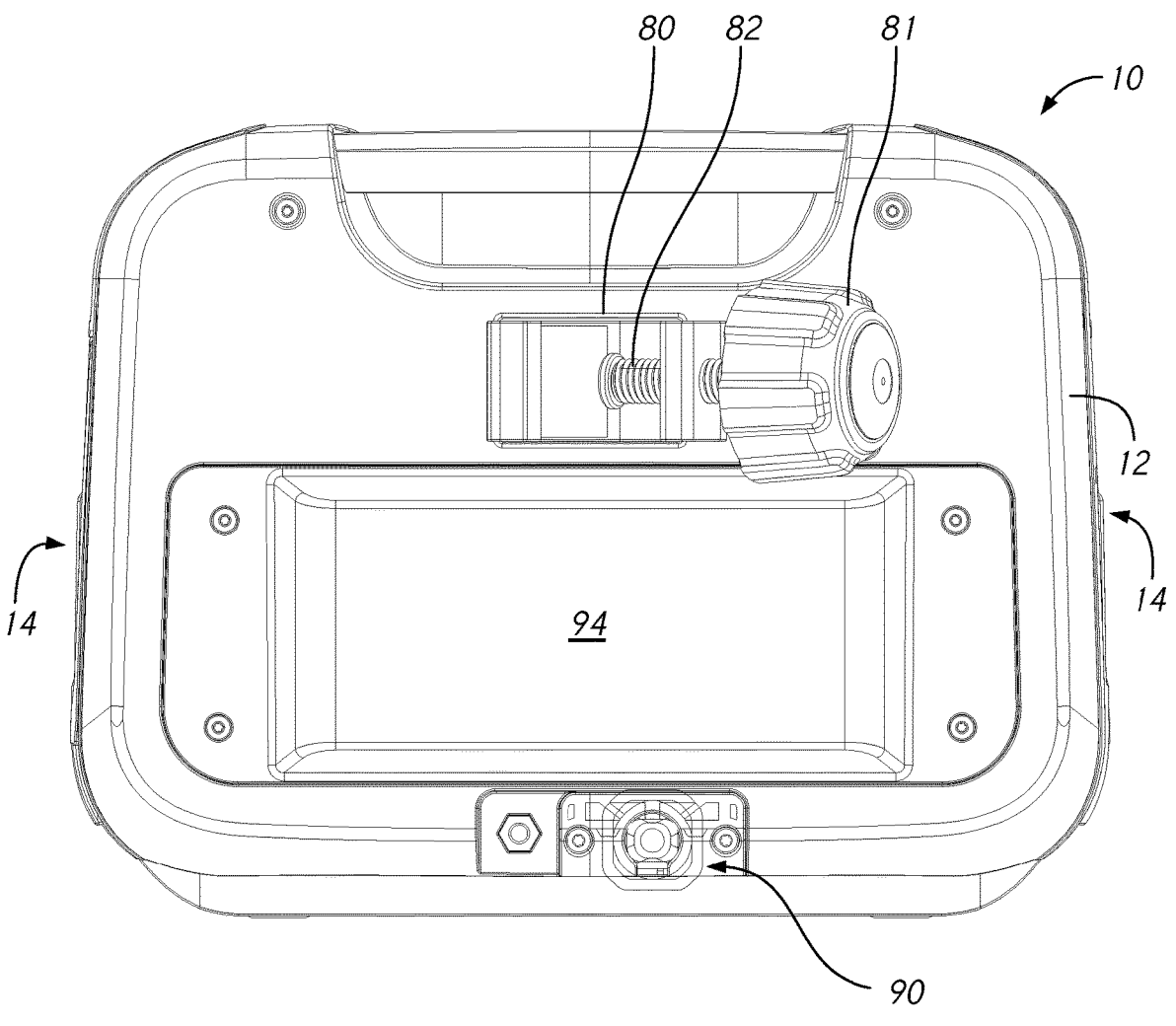
Figure 1D:
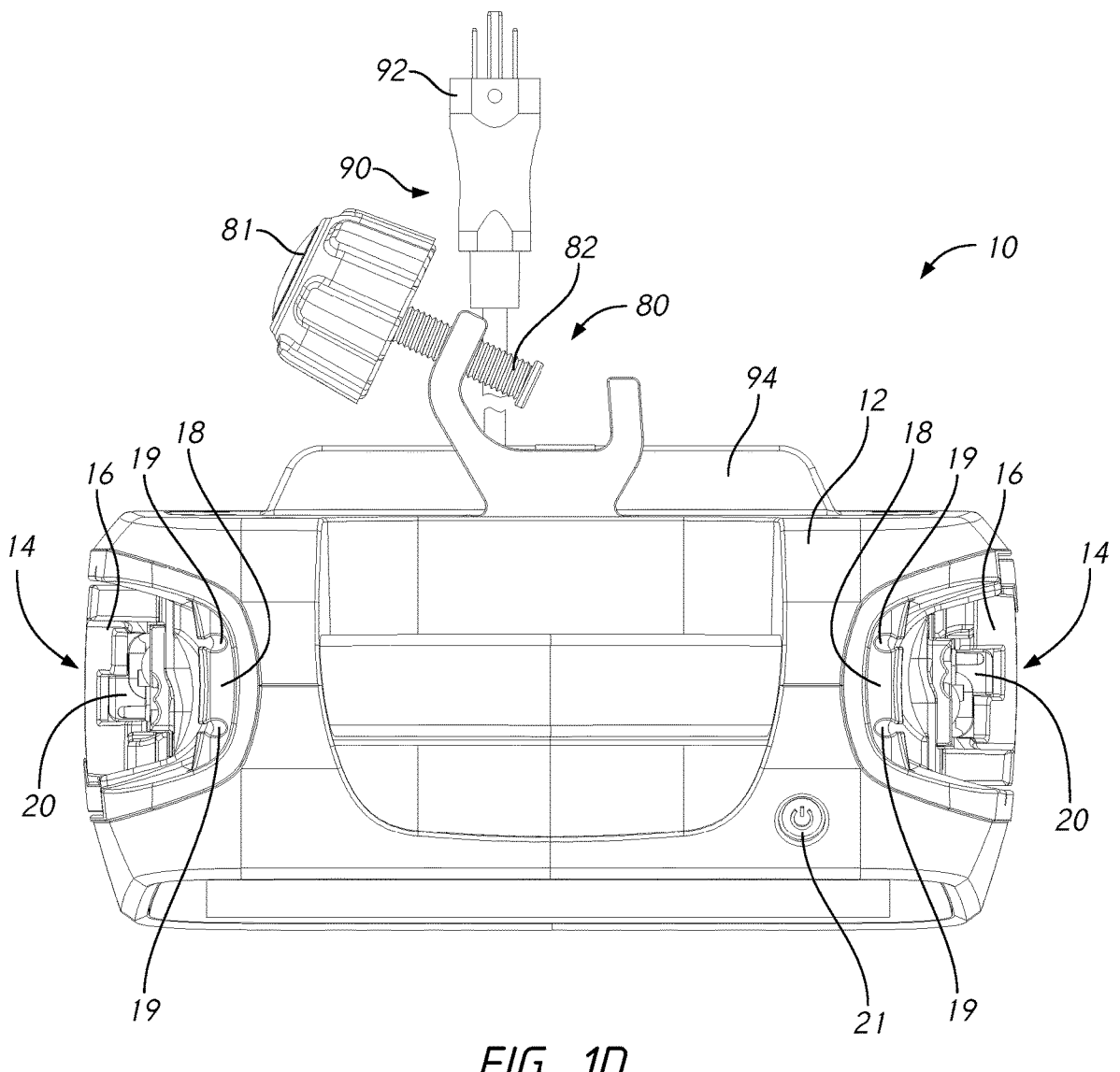
Figure 1E:
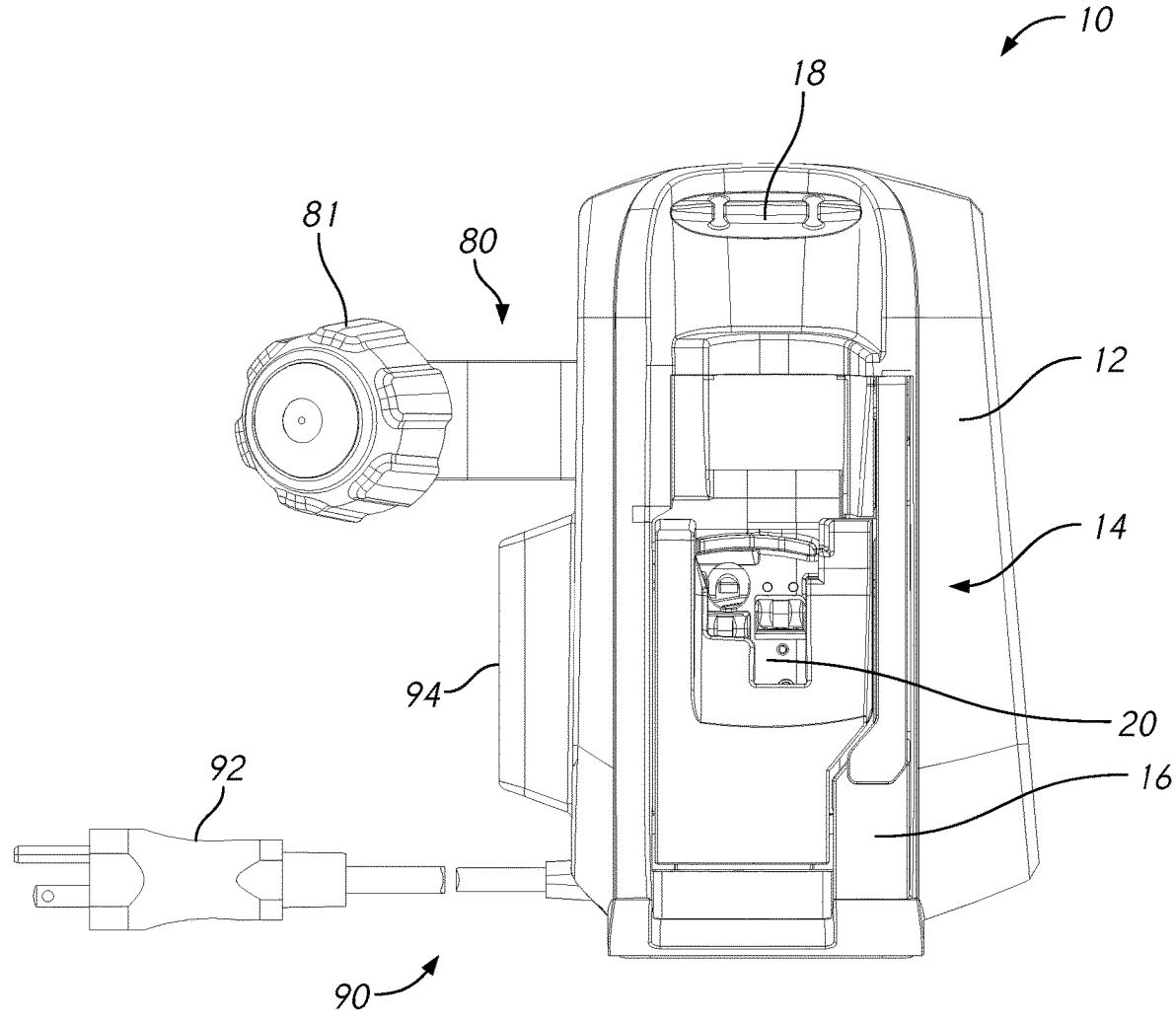

This specification provides textual descriptions and illustrations of many devices, components, assemblies, and subassemblies. Any structure, material, function, method, or step that is described and/or illustrated in one example can be used by itself or with or instead of any structure, material, function, method, or step that is described and/or illustrated in another example or used in this field. The text and drawings merely provide examples and should not be interpreted as limiting or exclusive. No feature disclosed in this application is considered critical or indispensable. The relative sizes and proportions of the components illustrated in the drawings form part of the supporting disclosure of this specification, but should not be considered to limit any claim unless recited in such claim.

Examples of Pump Systems

In some embodiments, a pump system can include a reusable pump driver and a disposable fluid holder, such as a fluid cassette, syringe, section of tubing, etc. A disposable cassette, which is typically adapted to be used only once for a single patient and/or only once for one fluid delivery cycle, is usually a small plastic unit having at least one inlet and an outlet respectively connected through flexible tubing to the fluid supply container and intravenously through a needle to the patient receiving the fluid. In some embodiments, the cassette can include a pumping chamber. The flow of fluid through the chamber can be controlled by a plunger or pumping element activated in a controlled manner by the pump driver. For example, the cassette chamber can have one wall formed by a flexible diaphragm against which the plunger is repeatedly pressed in a reciprocating manner, which causes the fluid to flow. The pump driver can include the plunger or pumping element for controlling the flow of fluid into and out of the pumping chamber in the cassette, and it may also include one or more controls and/or vents to help deliver the fluid to the patient at a pre-set rate, in a pre-determined manner, for a particular pre-selected time, and/or at a pre-selected total dosage.

In some embodiments, the fluid can enter a cassette through an inlet and can be forced through an outlet under pressure. The fluid is delivered to the outlet when the pump plunger forces the membrane into the pumping chamber to displace the fluid. During the intake stroke, the pump plunger draws back, the membrane covering the pumping chamber retracts or pulls back from its prior inwardly displaced position, and the fluid is then drawn through the open inlet and into the pumping chamber. In a pumping stroke, the pump plunger forces the membrane back into the pumping chamber to force the fluid contained therein through the outlet. By repeating this action in an electronically controlled manner, the fluid flows into and out of the cassette in a series of spaced-apart pulses rather than in a continuous flow. When the pulses occur in rapid succession, the flow approximates a continuous flow. The entire disclosure of U.S. Pat. No. 7,258,534 is incorporated by reference herein, for all purposes, for all that it contains, including but not limited to examples of pump drivers and disposable fluid holders. It is contemplated that any structure, material, function, method, or step that is described and/or illustrated in the '534 patent can be used with or instead of any structure, material, function, method, or step that is described and/or illustrated in the text or drawings of this specification.

Examples of Pump System Components

FIGS. 1A-1E show an electronic medical intravenous pump 10 with a housing 12 and at least one electromechanical pump driver 14 attached to the housing 12. As illustrated, a plurality of pump drivers 14 (e.g., at least two) can be integrally provided within the same housing 12 of a single medical pump 10. Either or both of the pump drivers 14 can include a cover 16 that partially or entirely encloses an outer surface of the pump driver 14, an indicator 18 (e.g., an illuminating communicator) attached to the cover 16, one or more tube holders 19, and a loader 20 configured to securely receive and releasably hold a disposable fluid holder (see, e.g., FIGS. 2A-2D), including but not limited to a cassette, syringe, and/or tubing. The one or more tube holders 19 can be configured to removably receive and securely hold one or more fluid-conveying tubes extending into or exiting from fluid holder when the fluid holder is received into the loader 20. The indicator 18 can communicate one or more messages to a user, such as by temporarily illuminating in one or more colors. Examples of one or more message include confirming that a pump driver 14 near the indicator is currently active and pumping or that one or more instructions being received from a user will apply to a pump driver 14 near the indicator 18. The loader 20 can be a mechanism with multiple moving parts that opens, closes, expands, contracts, clasps, grasps, releases, and/or couples with the fluid holder to securely hold the fluid holder on or within the pump 10 during fluid pumping into the patient. The loader 20 can be integrated into and positioned on or within the pump 10 near the cover 16 adjacent to the indicator 18.

A user communicator, such as display/input device 200, can be provided to convey information to and/or receive information from a user (e.g., in an interactive manner). As illustrated, the user communicator is a touch screen that is configured to provide information to a user through an illuminated dynamic display and is configured to sense a user's touch to make selections and/or to allow the user to input instructions or data. For example, the display-input device 200 can permit the user to input and see confirmation of the infusion rate, the volume of fluid to be infused (VTBI), the type of drug being infused, the name of the patient, and/or any other useful information. The display-input device 200 can be configured to display one or more pumping parameters on a continuing basis, such as the name of the drug being infused, the infusion rate, the volume that has been infused and/or the volume remaining to be infused, and/or the elapsed time of infusion and/or the time remaining for the programmed course of infusion, etc. As shown, the touch screen can be very large, for example at least about 4 inches×at least about 6 inches, or at least about 6 inches×at least about 8 inches. In the illustrated example, the touch screen fills substantially the entire front surface of the pump 10 (see FIG. 1A), with only a small protective boundary surrounding the touch screen on the front surface. As shown, the touch screen comprises at least about 80% or at least about 90% of the surface area of the front of the pump 10. In some implementations, the front of the touch screen comprises a clear glass or plastic plate that can be attached to the housing 20 in a manner that resists liquid ingress, such as using a water-proof gasket and/or adhesive that can withstand repeated exposure to cleaning and sanitizing agents commonly used in hospitals without significant degradation.

An actuator 21 can be provided separate from the user communicator. The actuator 21 can be configured to receive an input and/or display information to a user. As shown, the actuator 21 is a power button that permits the user to press on the actuator 21 to power up the pump 10. The actuator 21 can illuminated to communicate to the user that the pump 10 is power on. If the power source is running low, the actuator 21 can change the color of illumination to quickly show to a user that a power source needs to be replenished.

In some embodiments, the user communicator, such as a display/input device 200, can alternatively or additionally comprise one or more screens, speakers, lights, haptic vibrators, electronic numerical and/or alphabetic read-outs, keyboards, physical or virtual buttons, capacitive touch sensors, microphones, and/or cameras, etc.

During use, the pump 10 is typically positioned near the patient who is receiving fluid infusion from the pump 10, usually lying in a bed or sitting in a chair. In some embodiments, the pump 10 may be configured to be an ambulatory pump, which will typically include a smaller housing, user communicator, battery, etc., so as to be conveniently transportable on or near a mobile patient. In many implementations, the pump 10 is attached to an IV pole stand (not shown) adjacent to the patient's bed or chair. As shown, the pump 10 can include a connector 80 that is configured to removably attach the pump 10 to the IV pole stand. As shown, the connector 80 can comprise an adjustable clamp with a large, easily graspable user actuator, such as a rotatable knob 81, that can be configured to selectively advance or retract a threaded shaft 82. At an end of the shaft 82 opposite from the knob 81 is a pole-contacting surface that can be rotatably advanced by the user to exert a force against a selected region of the pole, tightly pushing the pole against a rear surface of the pump 10, thereby securely holding the pump 10 in place on the pole during use. The selected region of the pole where the contacting surface of the shaft 82 is coupled can be chosen so as to position the pump 10 at a desired height for convenient and effective pumping and interaction with the patient and user.

The pump 10 can include a power source 90. In some embodiments, the power source can comprise one or more channels for selectively supplying power to the pump 10. For example, as illustrated, the power source 90 can comprise an electrical cable 92 configured to be attached to an electrical outlet and/or a portable, rechargeable battery 94. One or more components of the pump 10 can operate using either or both sources of electrical power. The electrical cable 92 can be configured to supply electrical power to the pump 10 and/or supply electrical power to the battery 94 to recharge or to maintain electrical power in the battery 94.

Inside of the housing 20 of the pump 10, various electrical systems can be provided to control and regulate the pumping of medical fluid by the pump 10 into the patient and/or to communicate with the user and/or one or more other entities. For example, the pump 10 can include a circuit board that includes a user interface controller (UIC) configured to control and interact with a user interface, such as a graphical user interface, that can be displayed on the user communicator or display/input device 200. The pump 10 can include a printed circuit board that includes a pump motor controller (PMC) that controls one or more pump drivers 14. In some embodiments, the PMC is located on a separate circuit board from the UIC and/or the PMC is independent from and separately operable from the UIC, each of the PMC and UIC including different electronic processors capable of concurrent and independent operation. In some embodiments, there are at least two PMC's provided, a separate and independent one for each pump driver 14, capable of concurrent and independent operation from each other. The pump 10 can include a printed circuit board that includes a communications engine (CE) that controls electronic communications between the pump 10 and other entities (aside from the user), such as electronic, wired or wireless, communication with a separate or remote user, a server, a hospital electronic medical records system, a remote healthcare provider, a router, another pump, a mobile electronic device, a near field communication (NFC) device such as a radio-frequency identification (RFID) device, and/or a central computer controlling and/or monitoring multiple pumps 10, etc. The CE can include or can be in electronic communication with an electronic transmitter, receiver, and/or transceiver capable of transmitting and/or receiving electronic information by wire or wirelessly (e.g., by Wi-Fi, Bluetooth, cellular signal, etc.). In some embodiments, the CE is located on a separate circuit board from either or both of the UIC and/or the PMC(s), and/or the CE is independent from and separately operable from either or both of the UIC and/or the PMC(s), each of the PMC(s), UIC, and CE including different electronic processors capable of concurrent and independent operation. In some embodiments, any, some, or all of the UIC, CE, and PMC(s) are capable of operational isolation from any, some, or all of the others such that it or they can turn off, stop working, encounter an error or enter a failure mode, and/or reset, without operationally affecting and/or without detrimentally affecting the operation of any, some, or all of the others. In such an operationally isolated configuration, any, some, or all of the UIC, CE, and PMC(s) can still be in periodic or continuous data transfer or communication with any, some, or all of the others. The UIC, PMC(s), and/or CE can be configured within the housing 20 of the pump 10 to be in electronic communication with each other, transmitting data and/or instructions between or among each of them as needed.

Figure 2A:
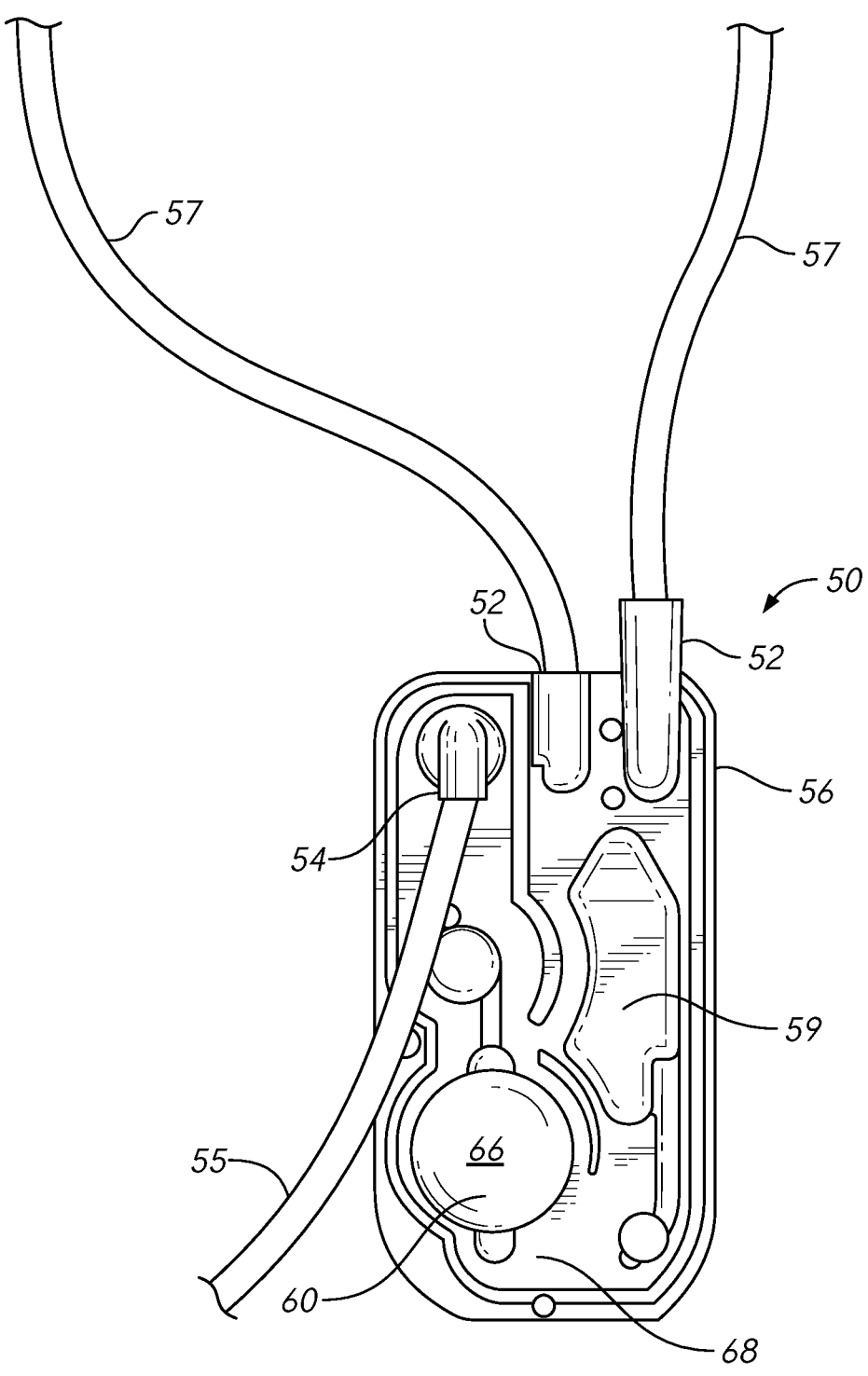
FIG. 2A shows an example of a cassette that can be used with the pump of FIG. 1.

FIG. 2A shows an example of a disposable fluid holder, such as a disposable cassette 50, that includes a plastic housing and a flexible, elastomeric silicon membrane. Any structure, material, function, method, or step that is described and/or illustrated in U.S. Pat. No. 4,842,584, which is incorporated herein by reference in its entirety, including but not limited to the pumping cassette, can be used by itself or with or instead of any structure, material, function, method, or step that is described and/or illustrated in this specification. The plastic housing of the cassette 50 can include one or more (e.g., two as shown) fluid inlets 52 and a fluid outlet 54 formed in a main body 56. The cassette 50 can be temporarily positioned for example in the loader 20 of a pump driver 14. The one or more fluid inlets 52 are coupled with one or more inlet tubes 57 in fluid communication with one or more sources of medical fluid, such as one or more IV bags, vials, and/or syringes, etc., containing medical fluid. If multiple inlets 52 and inlet tubes 57 are provided, as shown, then multiple sources of medical fluid can be simultaneously supplied to a patient through the cassette 50. The fluid outlet 54 is coupled to an outlet tube 55 in fluid communication with the patient, normally by way of a needle leading into a patient's blood vessel.

A flexible, elastomeric membrane forms a diaphragm 60 within a pumping chamber 66 on an inner face 68 of the main body 56. In operation, fluid enters through one or more of the inlets 52 and is forced through the outlet 54 under pressure. One or more fluid channels within the main body 56 of the cassette 50 convey the fluid between the inlets 52 and the outlet 54 by way of the pumping chamber 66. Before use, the cassette is typically primed with fluid, usually saline solution. A volume of fluid is delivered to the outlet 54 when a plunger 136 of the pump 10 (see, e.g., FIG. 3) displaces the diaphragm to expel the fluid from the pumping chamber 66. During an intake stroke, the plunger 136 retracts from the diaphragm 60, and the fluid is then drawn in through the inlet 52 and into the pumping chamber 66. In a pumping stroke, the pump 10 displaces the diaphragm 60 of the pumping chamber 66 to force the fluid contained therein through the outlet 54. In some embodiments, the directional movement of flow can be facilitated by one or more directional valve(s) (e.g., at one or more of inlet 52 or outlet 54). The fluid can flow from the cassette 50 in a series of spaced-apart pulses rather than in a continuous flow. In some embodiments, the pump 10 can deliver fluid to a recipient (e.g., a patient) at a pre-set rate, in a pre-determined manner, and for a particular (e.g., pre-selected) time or total dosage. The cassette 50 can include an air trap 59 in communication with an air vent (not shown).

FIGS. 2B, 2C, and 2D show three views of a cassette that is the same as or similar to the cassette of FIG. 2A. In FIGS. 2B and 2C, fluid can flow into an inlet 52, from a primary container, for example. Fluid can also flow into a secondary port 253, which can have a Y-connector with a resealable opening or a locking cap. Fluid coming in from the inlet 52 can pass through an A valve 220. Fluid coming in through a secondary port 253 can pass through a B valve 218. Fluid coming in through these two valves can then pass by a proximal air-in-line sensor 222. Fluid can then pass by, in a widening passage, a proximal pressure sensor 223.

Cassette Air Trap

The widened passage can form an air trap chamber 59, which can allow for fluid mixing. The air trap chamber is also shown in the side view of FIG. 2B. The air trap chamber 59 can be integral to the cassette. The air trap can be exposed to view above the upper edge of the cassette door when the door is closed. Air passes the proximal air-in-line sensor 222 before entering the air trap, which in some embodiments can have a volume of at least about 2.0 mL (e.g., 2.15 mL). The proximal pressure sensor (see, e.g., pressure sensor 223 of FIG. 3C) can monitor pressure in the air trap chamber 59. In some embodiments, the user can remove air or fluid from the proximal tubing and cassette air trap after the cassette door is closed. To remove air in the trap or the proximal tubing the user may be required to attach a container to a Line B port (e.g., secondary port 253 of FIG. 2C). A key, button, or other control (e.g., on an infuser display screen) can be selected to backprime when a delivery is not in progress. When the user selects backprime, for example, this can initiate rapid pumping of fluid from Line A to a user-attached container on Line B. In some embodiments, no fluid is delivered to the cassette distal line during a backprime. After the backprime control is released, a cassette leak test can be automatically performed.

In some embodiments, after passing through an air trap chamber 59, fluid can subsequently flow through an inlet valve 228 and from there into a pumping chamber 66. The pumping chamber 66 is also shown in the side view of FIG. 2D. From the pumping chamber 66, fluid can flow through an outlet valve 231 and then into a widened passage accessed by a distal pressure sensor 232. This passage subsequently narrows down to pass a distal air-in-line sensor 236. The two air-in-line sensors, proximal 222, and distal 236, can both be positioned near a bend in a passage or tubing, as shown in the side views of FIGS. 2B and 2D. Fluid can flow through or pass a precision gravity flow regulator 267, seen in FIG. 2D. A finger grip 245 is also seen protruding to the right in FIG. 2D. An outlet tube 55 is also shown coming from the precision gravity flow regulator 267 and leading to a patient. The features shown in the cross sectional schematics of FIGS. 2B-2D can correspond generally to the external cassette contours shown in FIG. 2A.

Fluid Delivery

A pumping system or infuser can deliver fluids from one or two drug sources through a sterile fluid pathway of administration set tubing, accessories and a cassette. In some embodiments, there is no contact between the fluid and an infusion mechanism subsystem (see FIG. 3A and the electromechanical portion 356 of FIG. 3C).

A system user can enter a multi-step therapy program to perform an infusion in a sequence of different delivery rates and volumes. The user can also enter a piggyback therapy program that sequentially delivers fluid from Line B and Line A. Line B starts delivering first and after Line B completes delivery, then Line A delivery is automatically started.

Alternatively, fluid from lines A and B can be interspersed or delivered simultaneously but at different rates such that a consistent ratio is maintained between the substances. For example, a concurrent therapy program can combine fluid from both Line A and Line B in the cassette pumping chamber during each chamber fill cycle, then deliver a combination of the two fluids with each plunger stroke.

Figure 5:
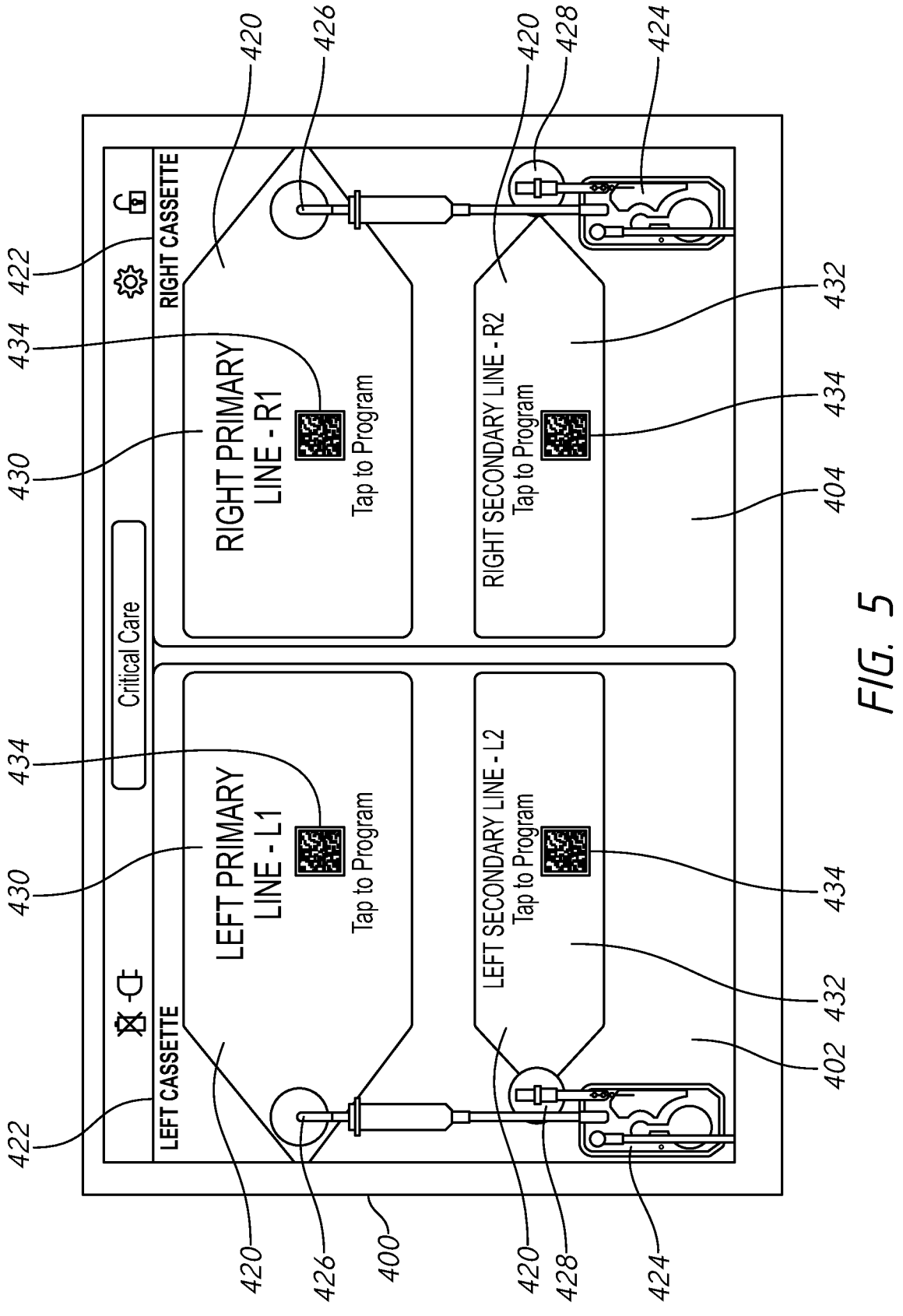
FIG. 5 shows an example of another graphical user interface of a user communicator, permitting a user to select options for programming medical fluid infusion.

An additional or alternative infusion pump cassette that can be used with any embodiment in this specification is illustrated in FIG. 5 of U.S. Pat. No. 7,402,154. An elastomeric membrane 60 forms an inlet diaphragm 62, an outlet diaphragm generally indicated at 64, and a pumping chamber 66 located between the inlet and outlet diaphragms 62 and 64 on an inner face 68 of the main body 56. In operation, fluid enters through the inlet 52 and is forced through outlet 54 under pressure. The fluid is delivered to the outlet 54 when the plunger 136 of the pump 10 displaces the pumping chamber 66 to expel the fluid. During the intake stroke the plunger 136 releases the pumping chamber 66, and the fluid is then drawn through the inlet 52 and into the pumping chamber 66. In a pumping stroke, the pump 10 displaces the pumping chamber 66 to force the fluid contained therein through the outlet 54. The directional movement of flow can be facilitated by one or more directional valve(s) (e.g., at one or more of inlet 52 or outlet 54). At low rates the flow can be delivered in discrete volumes as the pump 10 displaces the pump chamber in successive steps. Thus, the fluid can flow from the cassette 50 in a series of spaced-apart pulses rather than in a smoothly continuous flow. Typically, this pump can deliver fluid to a recipient (e.g., a patient) at a pre-set rate, in a pre-determined manner, and for a particular (e.g., pre-selected) time or total dosage. A flow stop can be formed as a switch in a main body and protrude from the inner surface 68. This protrusion can form an irregular portion of the inner surface 68 which can be used to align the cassette 50 as well as monitor the orientation of the cassette 50. The flow stop can provide a manual switch for closing and opening the cassette 50 to fluid flow. A rim 72 is located around the outer surface of the main body 56 and adjacent the inner surface 68. The rim 72 can be used to secure the cassette in a fixed position relative to the pump 10 of U.S. Pat. No. 7,402,154.

Figure 3A:
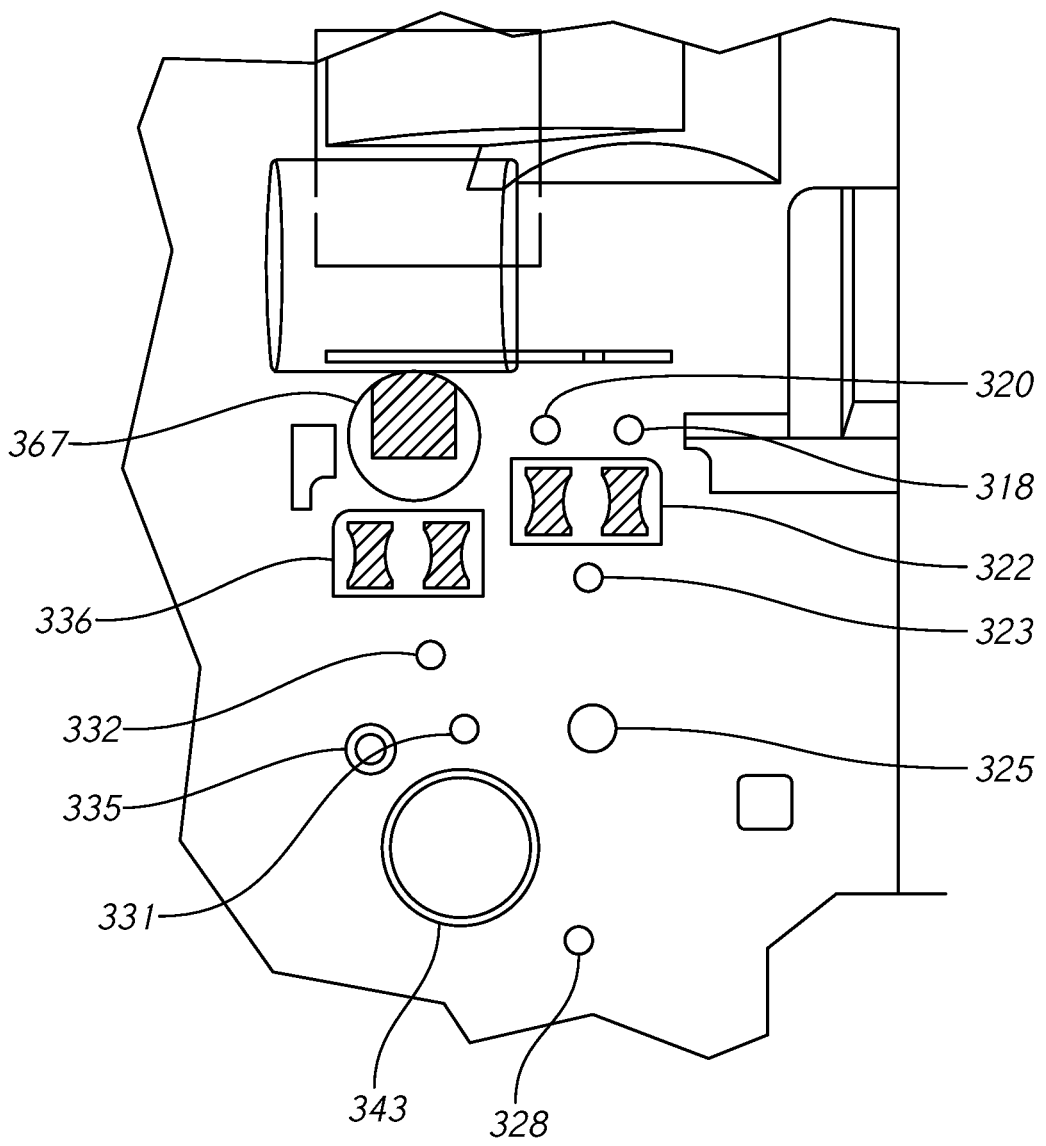
FIG. 3A illustrates components of a pump driver that can interact with the cassette(s) of FIGS. 2A-2D.

FIG. 3A illustrates an example of hardware or components of the pump driver 14 that can be configured to interact with a fluid holder such as the cassette of FIGS. 2A-2D. In FIG. 3A, an A valve interface 320 can correspond to or interact with an A valve 220. Similarly, a B valve interface 318 can correspond to or interact with a B valve 218 as shown in FIG. 2C. A proximal air-in-line sensor 322 can be located outside of a cartridge and can interact with a loop or bend in at least partially transparent fluid pathway, for example. In the illustrated example, the sensor 322 is depicted with two vertical portions that can pinch or otherwise be positioned adjacent to a tube running vertically between them. A proximal pressure sensor interface 323 can interact with a pressure sensor 223. A force-sensor, such as resistor 325, can be used to determine whether a cartridge is in physical contact with the hardware, or a portion of a pump having the hardware, shown in FIG. 3A. In some embodiments, an inlet valve 228 is actively driven and can receive actuation from an inlet valve interface 328. Similarly, an outlet valve interface 331 can interact with an outlet valve 231. A plunger 343 can extend toward and interact with a pumping chamber 66 (see FIGS. 2C and 2D). A cassette locator 335 can be used to provide alignment and registration of physical interacting components when a cassette such as shown in FIGS. 2A-2D is inserted into or aligned with the hardware components shown in FIG. 3A. A distal pressure sensor interface 332 is located below a distal air-in-line sensor 336. Above this is located a regulator actuator 367, which can be configured to interact with the precision gravity flow regulator 267.

Figure 3B:
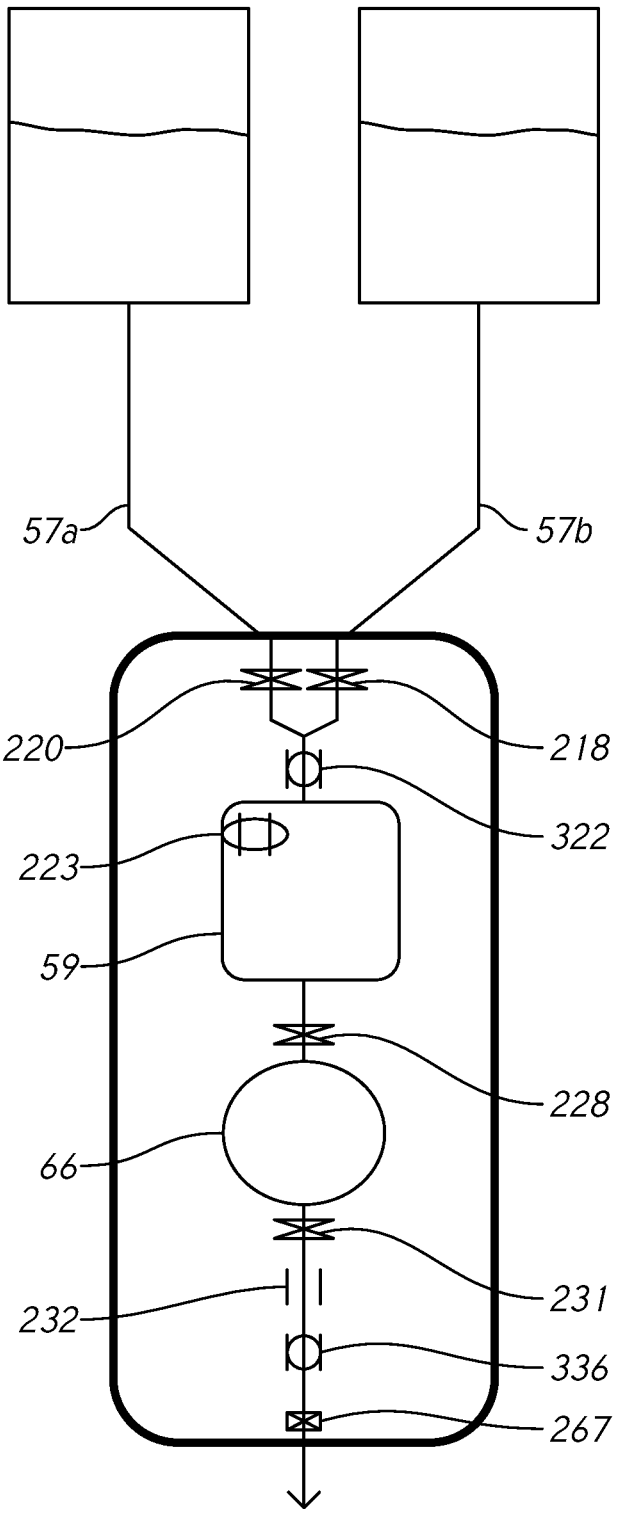
FIG. 3B illustrates a fluid path through a cassette such as one or more of those shown in FIGS. 2A-2D, such as may be controlled by the hardware of FIG. 3A.

FIG. 3B illustrates a fluid path through a cassette such as the fluid path shown in the cassette(s) of FIGS. 2A-2D, as actuated by the hardware of FIG. 3A. The physical components of FIGS. 2A-2D and FIG. 3A can control and evaluate fluid in the path illustrated in FIG. 3B. In FIG. 3B, fluid coming in from either a primary line 57A or a secondary line 57B can pass through the A valve 220 or the B valve 218, respectively. Incoming fluid can then mix in a joined passage, and pass a by a proximal air-in-line sensor 322. Fluid can then enter an air trap chamber 59 having a proximal pressure sensor 223. This chamber can allow fluid from two sources to mix. From here, fluid can flow through an inlet valve 228 and from there into a pumping chamber 66. From the pumping chamber 66, fluid can flow through an outlet valve 231, past a distal pressure sensor 232, and past a distal air-in-line sensor 336. Fluid can flow through or pass a precision gravity flow regulator 267 before proceeding from a cassette toward a patient through tubing.

In a system using active, positively-controlled valves with motors, during fluid delivery, the plunger (e.g., 343 in FIGS. 3A and 3C) can repeatedly cycle between the home position and the extended position. To draw fluid into the pumping chamber (e.g., 66) the inlet valve (e.g., 228) is opened. The outlet valve can then promptly close. In some embodiments, opening of the inlet valve can automatically cause the outlet valve (e.g., 231) to close. When the plunger reaches the home position, the plunger motion pauses while the inlet valve (e.g., 228) is closed, pressure is equalized, and the outlet valve (e.g., 231) is opened. Then the plunger extends and the positive pressure forces fluid out of the pumping chamber and into the distal line (e.g., 55) of the set, which can be connected to a patient.

The plunger stepper motor (e.g., motor 342 of FIG. 3C or the motor of FIG. 4C) can be activated by current pulses through the motor windings. In some embodiments, a plunger motor can use different patterns (e.g., 6 different patterns) of pulses can be used, depending on the delivery rate. As the rate increases, a pause between successive steps of the motor decreases. In some embodiments, valve motors can use a single pattern of current pulses through the motor windings. The patterns of current pulses for the motors are advantageously controlled by a PMC microcontroller (e.g., in the controller 380).

Figure 3C:
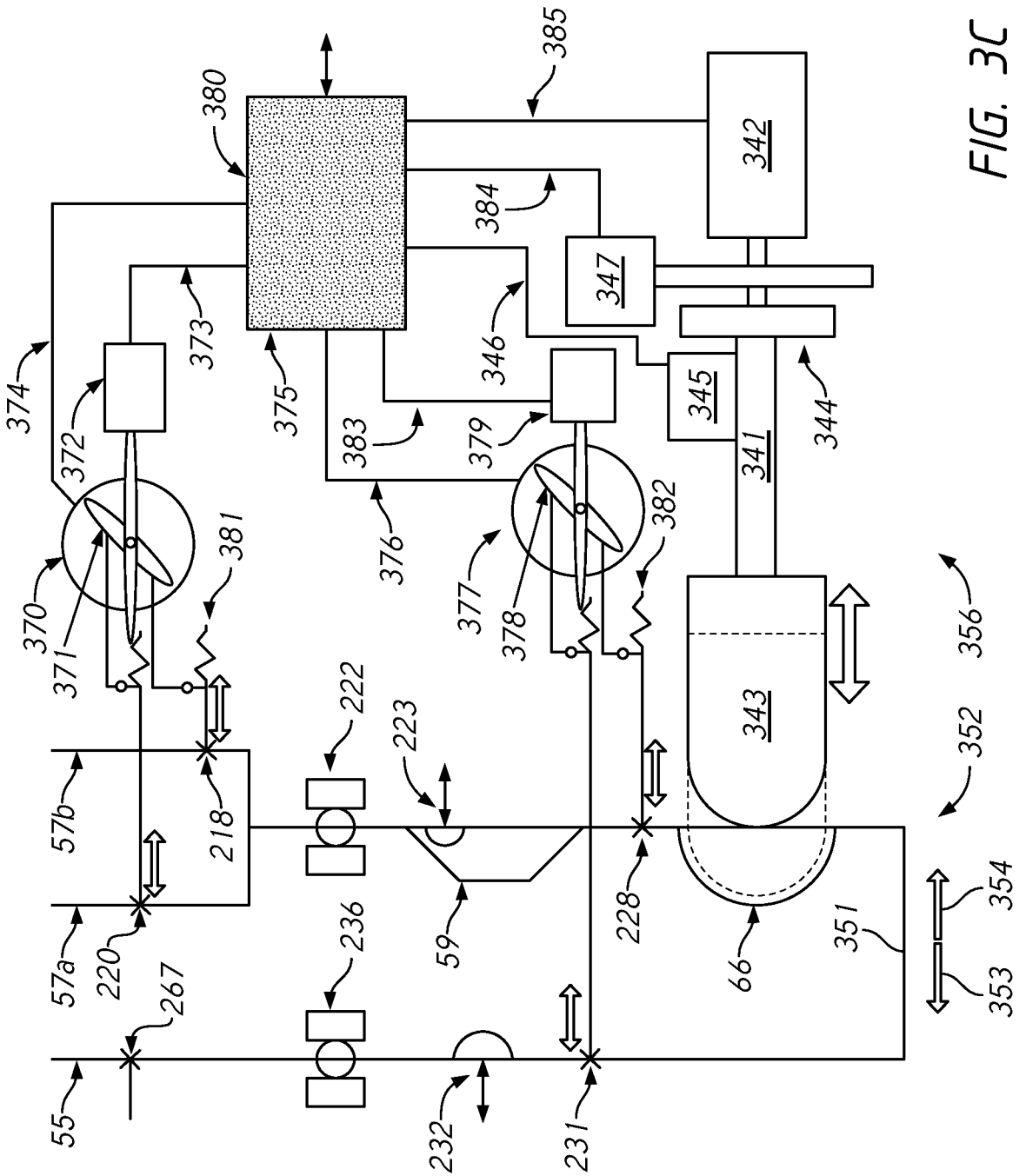
FIG. 3C illustrates schematically how hardware (e.g., FIG. 3A) interacts with a cassette (e.g., FIGS. 2A-2D) to affect flow along a fluid path.

FIG. 3C further illustrates schematically how hardware (e.g., FIG. 3A) can interact with a cassette (e.g., FIGS. 2A-2D) along a fluid path. FIG. 3C shows a patient or distal line 55 at the top left corner. At the left is shown an example of a consumable or cassette portion 352. At the right is shown an example of an electromechanical portion 356. In the cassette 352, a distal side 353 is toward the left, and a proximal side 354 is toward the right. A fluid path 351 is illustrated, passing generally from inlets 57A and 57B to outlet 55. Line A 57a leads to a Line A valve or pin 220, which can move to the right and left as shown by the arrow. Similarly, Line B 57B can lead to a Line B valve or pin 218.

A spring such as the spring 381 can be deployed with respect to both the valve 218 and the valve 220, and a cam 371 can connect a stepper motor 370 with the valve to 220 and the valve 218. The stepper motor 370 can interact with a line AB position sensor 372, with feedback 373 provided to a controller or controllers 380. A controller 380 can in turn provide input and/or power 374 to the stepper motor 370. In this arrangement, the valves 220 and 218 are actively and positively controlled by a motor and a controller.

For the outlet valve and pin 231 and the inlet valve and pin 228, a stepper motor 377 having a cam 378 and associated springs 382 can interact with the valves 228 and 231. In some embodiments, the cam 371 can cause the associated valves 220, 218 not to be opened simultaneously. In some embodiments, the inlet valves 220 and 218 are not open simultaneously to that fluid does not mix in either of inlet lines 57a or 57b.

Similarly for the cam 378 and the valves 231 and 228, if the cam forms a rigid elongate structure as shown, it can pull on one valve while pushing on the other and when it swings the other direction push and pull in an alternating manner. The valves 228 and 231 can open at alternating times such that fluid intake occurs during a draw portion of a plunger stroke, and fluid is expelled during a push portion of a plunger stroke. Having the valve open simultaneously or other synchronization problems can be avoided to discourage backflow.

An input output valve position sensor 379 can be connected to a physical component of the stepper motor 377. The sensor 379 can provide feedback to the controller or controllers 380, which can in turn send input and/or power 376 to the stepper motor 377.

The controller or controllers 380 can also interact with a third stepper motor 342, which can cause movement of a lead screw 341 connected to a plunger or piston 343, which in turn physically interacts with the pumping chamber 66. A linear position sensor 345 can provide feedback 346 of this process to a controller 380. Similarly, a rotary position sensor 347 can provide feedback 384 to a controller 380. Thus, linear and rotary position feedback can be provided either as a backup, as an alternative, or otherwise. A coupler 344 can be provided between the stepper motor of 342 and the lead screw 341. Input and/or power 385 can be provided from the controller 380 to the stepper motor 342. The plunger or piston 343 can follow a reciprocating pattern as shown by the arrow. Thus, the electromechanical portion 356 of a pump can have multiple reciprocating portions and multiple motors. The reciprocation of the valves 220, 218, 231 and 228 can be timed and coordinated with the reciprocation of the piston 343 (e.g., by controller/s 380) to encourage fluid to move through the fluid path 351. Although additional feedback lines are not shown in FIG. 3C, sensor feedback can be provided from the distal air inline sensor 236 and the proximal area line sensor 222, as well as the distal pressure sensor 232 and the proximal pressure sensor 223.

Valve Operation

In some modes of operation, the valves 218 and 220 can each be open for some percentage of the duration of an intake stroke of the plunger 343, while the inlet valve 228 is open for approximately the entire duration of the same intake stroke. Concurrent flow can independently control two rates, drawing a proportional amount of fluid from each of lines A and B into the pumping chamber. During an expelling stroke, the outlet valve 231 can remain open approximately the entire time. Intake and expelling strokes can have similar durations. However, an advantageous approach uses a quick intake stroke during which the pump chamber fills, and then a series of smaller output strokes. For example, intake may occur within seconds, while the output strokes continue over a much longer time until the pump chamber needs to be filled again. Proper cadence and sequencing of the motors can be confirmed directly by the feedback from the motors 373, 383, and 385. Proper pressure response of the fluid can be confirmed or measured by the sensors 223 and 232. Potential air bubbles can be evaluated by sensors 222 and 236. System interpretation of sensors 223 and 232, and of 222 and 236, can lead respectively to occlusion alarm and air alarm states that result in unexpected flow discontinuities.

Valve motors such as the motors 370 and 377 of FIG. 3C can be controlled by a pump mechanism controller ("PMC") microcontroller using a chopper motor drive. The valve motors 370 and 377 can be the same, with one motor used for a pair of valves.

An Inlet/Outlet (I/O) valve motor (e.g., 377 in FIG. 3C) opens and closes the cassette pumping chamber inlet and outlet valves (e.g., 228, 231) in an administration set cassette. The cassette can have a membrane that is exposed by openings in the back of the cassette body above where there are valve chambers in the cassette. The Inlet valve pin (e.g., 228) is opened to allow fluid to enter the pumping chamber (e.g., 66) through the air trap (e.g., 59) from the proximal line, which is selected by the Line A/B Select valves (e.g., 218, 220). When the pumping chamber is filled the Inlet valve (e.g., 228) is closed, the pumping chamber pressure is set and the Outlet valve (e.g., 231) is opened to allow fluid to be pumped into the distal line of the set.

A state machine (e.g., in or associated with the controller 380) can run a program for controlling the I/O valve motor (e.g., 370, 377). In an optical approach, cam flags can protrude from a portion of the drive train. Rotational cam flag signals can be acquired optically during or after each motor step and are monitored using a state machine. As with the other motors, if there is an error in the Inlet/Outlet valve motor position (phase loss), then the motor can be re-initialized to the current position.

The Line A/B Select (LS) valve motor (e.g., 370 in FIG. 3C) opens and closes the Line A and Line B select valves (e.g., 220, 218) in the administration set cassette, using openings in the back of the cassette body for actuator access. The Line A valve (e.g., 220) controls the primary inlet port to the cassette which can be attached permanently to the set proximal tubing. The Line B valve (e.g., 218) controls the secondary inlet port, which may have a screw cap, a Pre-pierced or a Clave attached to it, depending on the type of set.

Example System Operation

In some embodiments, a pump system can have a cassette door with a handle that supports an administration set cassette such as that illustrated in FIGS. 2A-2D. When the door is open in a loading position the user can slide the cassette into a slot with a cassette guide spring. When the door is closed the cassette is aligned and the front of the cassette makes contact with a door datum surface, actuator and sensor subassemblies (plunger 343 and pins or valves 218, 220, 228, 231) make contact with a cassette elastomeric membrane, and a cassette guide spring can push a fluid shield against the front face of a mechanism chassis. The door can be released from the handle when it is in the loading position, allowing the door to be perpendicular to the mechanism fluid shield. This allows the user to clean the rear of the door and the fluid shield, or to remove any object which has fallen behind the door.

A cassette locator (see, e.g., 335 in FIG. 3A) can be a pin that helps align the cassette with the mechanism as the door is closed and keeps the cassette in the correct position during delivery.

The cassette can have a flow regulator valve (e.g., the precision gravity flow regulator 267, seen in FIG. 2D) distal to the pumping chamber (e.g., the chamber 66 of FIGS. 2A-3D). The flow regulator valve can be closed by the user after an administration set is primed. The proximal line can be clamped as an additional prevention of free flow. As the door is closed, an actuator connected to the door handle can automatically open the flow regulator valve after the pumping chamber outlet valve pin closes the outlet valve. The flow regulator valve can be used by the operator to control fluid flow rate when the administration set is used independently for a gravity drip infusion.

A reciprocating pumping piston/plunger (e.g., the plunger 343 of FIG. 3C) can be actuated by a motor (e.g., the motor 342). As schematically shown in FIG. 3C, a pump plunger motor and drive train can be perpendicular to a pumping chamber membrane opening on the rear of a cassette. The drive train can have location sensors that are monitored by motor control software on a PMC microcontroller (see controller 380 of FIG. 3C). The software can implement state machines which control the motor operation.

An inlet valve to the pumping chamber (e.g., the valve 228) can be actuated by a motor (e.g., the motor 377), and a drive train can extend an actuator through an opening in the rear of the cassette to reach the valve. The same motor can be used for the outlet valve, which can improve synchronization. A default position is with the inlet valve (e.g., the valve 228) closed by a spring (e.g., 382) which can apply steady pressure to a valve pin. The drive train (see generally 377, 378 and related structures) has a location sensor (e.g., 379) that is monitored by (383) motor control software on the PMC microcontroller (e.g., 380). The software implements state machines which can control the motor operation. The same description here generally applies to an outlet valve (e.g., 231), actuated by the same motor (e.g., 377).

Line A select valve (e.g., 220) for primary proximal fluid line A (e.g., 57a) and Line B select valve (e.g., 218) for fluid line B (e.g., 57b) can be actuated by a motor (e.g., 370). As described above for the valves 228 and 231, the valves 220 and 218 can be accessed by a drive train (which may include the cam 371 and springs such as 381) through openings in a cassette, driven by a motor (e.g., 370), as tracked by a location sensor (e.g., 372) and monitored (373) by software in a controller (380).

One or more proximal and distal air-in-line sensors (222, 236) can be used to detect air passage into (proximal) or out of (distal) the cassette. Both sensors can be ultrasound piezoelectric crystal transmitter/receiver pairs. Liquid in the cassette between the transmitter and receiver conducts the ultrasonic signal, while air does not. This can result in a signal change indicating a bubble in the line.

One or more proximal and distal MEMS pressure sensors (223, 232 of FIG. 3C) can be used to detect the pressure of the tubing into (proximal) or out of (distal) the cassette. Microelectromechanical systems (MEMS) pressure sensors are an integrated circuit, which have piezo electric resistors diffused into a micro-machined diaphragm to measure strain from a steel ball that extends through the top of the IC package. The steel ball is driven by a pressure pin which is in contact with the cassette membrane.

A cassette presence sensor detects that the cassette is in the door when it is closed. The sensor can be a dome switch mounted in an infusion mechanism subsystem fluid shield.

The dome switch can make contact with the cassette when the cassette is correctly aligned with the fluid shield. The switch output signal can be acquired and processed by PMC microcontroller software (e.g., in controller 380).

Motor control interfaces can provide amplification of control signals output by the PMC microcontroller (e.g., the controller 380). PMC microcontroller software can compute motor winding current values which are converted to analog voltages by a digital-to-analog converter (DAC). The control voltages input to the motor control interface can cause amplifiers to drive the selected motor winding with current modulated by a chopper pulse width modulator controller. Preferably, one motor winding is active at a time.

Sensor interfaces in an infusion mechanism subsystem can convert air-in-line, pressure and motor drive position sensor signals into analog voltage signals. The analog voltages are processed by an analog-to-digital converter (ADC) in the PMC microcontroller which outputs digital values. PMC microcontroller software state machines acquire and process data from the sensors.

Non-volatile memory in an infusion mechanism subsystem can be connected to the PMC microcontroller with a serial communications link (SPI bus). The non-volatile memory can be used to store calibration values for the motor drive trains and sensors during manufacturing. Additional system parameters and an alarm log are also stored by the PMC microcontroller in this memory.

Any control and/or feedback systems of this specification can be configured to generate highly specific, real-time data on how an infusion pump is operating and how fluid in a cassette is responding. This data already exists for precision operation of an infusion device, and it can be conveniently organized and stored (e.g., in a memory of the pump system itself). This data can provide highly accurate predictions of how and when medication will reach a target destination, or achieve a particular level in a target destination. Thus, the sensors, controllers, cam flags, feedback software, etc. described herein is highly valuable in predicting further outcomes, patient medication status, and/or otherwise displaying information to a user.

Figure 3D:
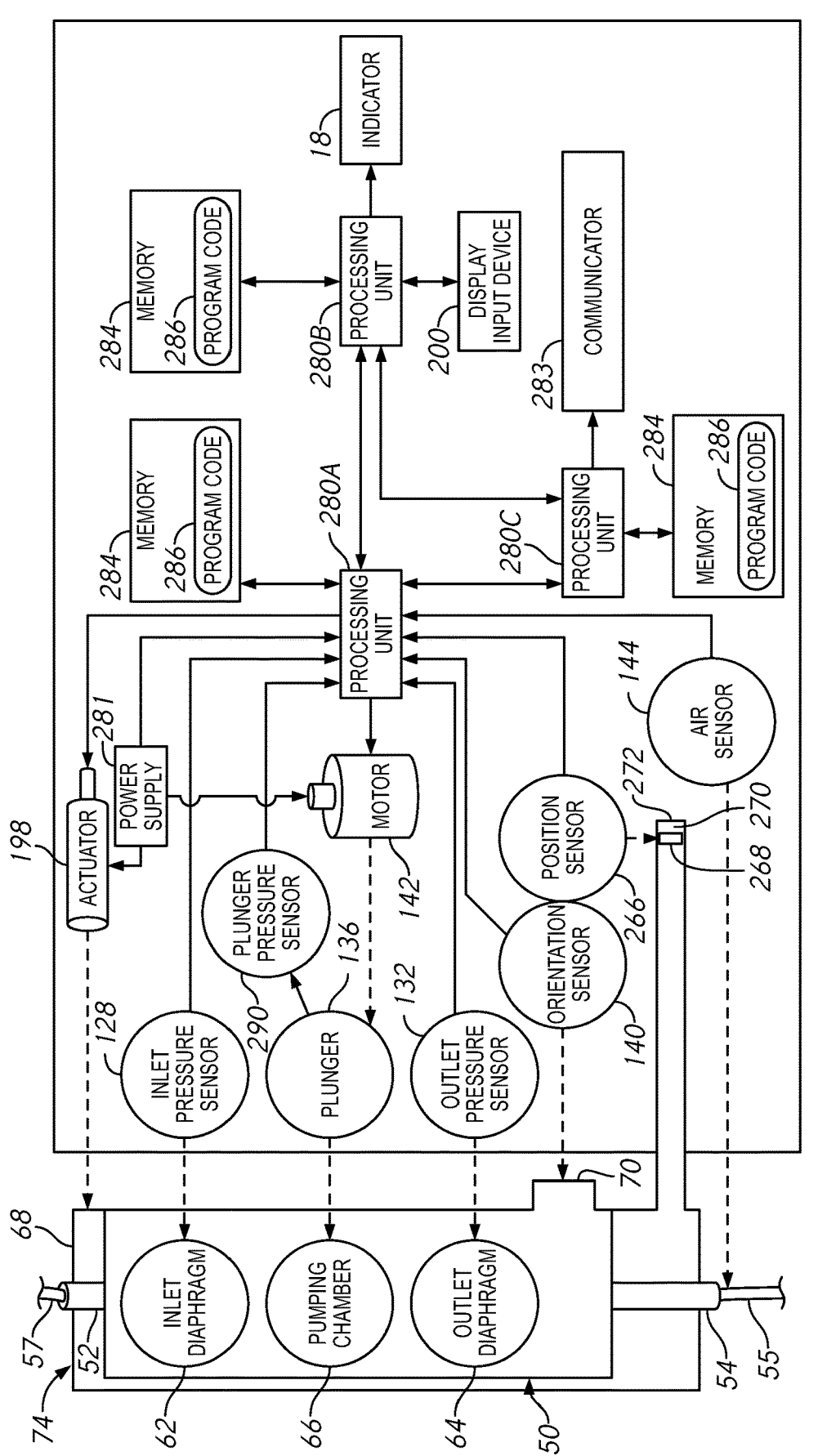
FIG. 3D shows an example of a schematic diagram of some functional components of a medical pump system that can be used with or instead of those illustrated or described elsewhere in this application.

FIG. 3D is a schematic diagram of some functional components for a medical pump (e.g., the pump 10 of FIGS. 1A-1E) that in some embodiments can be used in connection with the disposable cassette 50 (see FIGS. 2A-D) for delivering a fluid to a patient. Some of the components and/or functions illustrated and/or described in connection with FIG. 3D are alternatives or additions to those illustrated in the cassette of FIGS. 2A-3C. One or more processors or processing units 280 can be included in pump 10 that can perform various operations. The processing unit(s) 280 and all other electrical components within the pump 10 can be powered by a power supply 281, such as one or more components of power source 90 of pump 10. In some embodiments, the processing unit 280*a* can be configured as a pump motor controller (PMC) to control the electric motor 142 being energized by the power supply 281. When energized, the electric motor 142 can cause the plunger 136 to reciprocate back and forth to periodically actuate, press inward, and/or down-stroke, causing plunger 136 to temporarily press on pumping chamber 66, driving fluid through cassette 50. The motor 142, plunger 136, sensors 128, 290, 132, 140, 266, 144 can be included in or as an integrated part of the pump driver 14 of the pump 10. In some embodiments, as shown, the inlet pressure sensor 128 engages the inlet diaphragm 62 of cassette 50, and the outlet pressure sensor 132 engages the outlet diaphragm 64 of cassette 50. When retracting, moving outward, or on an up-stroke, the plunger 136 can release pressure from pumping chamber 66 and thereby draw fluid from inlet 52 into pumping chamber 66. Differential pressure within the cassette can drive the inlet opening during the pump chamber fill cycle. In some implementations of cassette 50, a flow stop 70 is formed as a pivotal switch in the main body 56 and protrudes a given height from the inner surface 68. This protrusion forms an irregular portion of the inner surface 68 which can be used in some embodiments to align the cassette 50 as well as monitor the orientation of the cassette 50. In some embodiments, one form of a flow stop 70 can provide a manual switch or valve for closing and opening the cassette 50 to fluid flow.

In some embodiments, the processing unit 280*a* can control a loader 20 of the pump 10 with an electronic actuator 198 and a front carriage being energized by the power supply 281. When energized, the actuator 198 can drive the front carriage 74 between closed or open positions. The front carriage 74 in the open position can be configured to receive the cassette 50 and in the closed position can be configured to temporarily securely retain the cassette 50 until the front carriage is moved to the closed position. A position sensor 266 for the cassette 50 can be provided in the pump 10. The position sensor 266 can monitor the position of a slot 268 formed in a position plate 270. The position sensor 266 can monitor a position of an edge 272 of a position plate 270 within the pump 10. By monitoring the position of the position plate 270, the position sensor 266 can detect the overall position of the front carriage of the loader 20 and/or confirm that the cassette 50 is inserted into the loader 20 of the pump driver 14. The position sensor 266 can be a linear pixel array sensor that continuously tracks the position of the slot 268. Of course, any other devices can be used for the position sensor 266, such as an opto-tachometer sensor.

A memory 284 can communicate with the processing unit 280*a* and can store program code 286 and data necessary or helpful for the processing unit 280 to receive, determine, calculate, and/or output the operating conditions of pump 10. The processing unit 280*a* retrieves the program code 286 from memory 284 and applies it to the data received from various sensors and devices of pump 10. The memory 284 and/or program code 286 can be included within or integrally attached to (e.g., on the same circuit board) as the processing unit 280*a*, which in some embodiments can be the configuration for any processor or processing unit 280 in this specification.

In some embodiments, the program code 286 can control the pump 10 and/or track a history of pump 10 operation details (which may be recorded and/or otherwise affected or modified, e.g., in part by input from sensors such as air sensor 144, position sensor 266, orientation sensor 140, outlet pressure sensor 132, plunger pressure sensor 290, inlet pressure sensor 128, etc.) and store and/or retrieve those details in the memory 284. The program code 286 can use any one or more of these sensors to help identify or diagnose pumping problems, such as air in a pumping line, a pumping obstruction, an empty fluid source, and/or calculate expected infusate arrival time in a patient. The display/input device 200 can receive information from a user regarding a patient, one or more drugs to be infused, and details about a course of infusion into a patient. The display/input device 200 can provide a clinician with any useful information regarding the pumping therapy, such as pumping parameters (e.g., VTBI, remaining volume, infusion rate, time for infusion, elapsed time of infusion, expected infusate arrival time, and/or time for completion of infusion, etc.) Some or all of the information displayed by the display/input device 200 can be based on the operation details and calculations performed by the program code 286.

In some embodiments, the operation details can include information determined by the processing unit 280*a*. The processing unit 280*a* can process the data from pump 10 to determine some or all of the following operating conditions: whether or when the cassette 50 has been inserted, whether or when the cassette 50 is correctly oriented, whether or when the cassette 50 is not fully seated to the fixed seat 162, whether or when the front carriage assembly 74 is in an open or closed position, whether or when a jam in the front carriage assembly 74 is detected, whether or when there is proper flow of fluid through the cassette 50 to the patient, and whether or when one or more air bubbles are included in the fluid entering, within, and/or leaving cassette 50. The processing unit 280*a* can be configured to determine one or more operating conditions to adjust the operation of the pump 10 to address or improve a detected condition. Once the operating condition has been determined, the processing unit 280*a* can output the operating condition to display 200, activate an indicator window, and/or use the determined operating condition to adjust operation of the pump 10.

For example, the processing unit 280*a* can receive data from a plunger pressure sensor 290 operatively associated with the plunger 136. The plunger pressure sensor 290 can sense the force on plunger 136 and generate a pressure signal based on this force. The plunger pressure sensor 290 can communicate with the processing unit 280*a*, sending the pressure signal to the processing unit 280*a* for use in helping to determine operating conditions of pump 10.

The processing unit 280*a* can receive an array of one or more items of pressure data sensed from the cassette inner surface 68 determined by the plunger pressure sensor 290 and inlet and outlet pressure sensors 128 and 132. The processing unit 280*a* can combine the pressure data from the plunger pressure sensor 290 with data from inlet and outlet pressure sensors 128 and 132 to provide a determination as to the correct or incorrect positioning of cassette 50. In normal operation, this array of pressure data falls within an expected range and the processing unit 280*a* can determine that proper cassette loading has occurred. When the cassette 50 is incorrectly oriented (e.g., backwards or upside down) or when the cassette 50 is not fully seated to the fixed seat 162, one or more parameters or data of the array of pressure data falls outside the expected range and the processing unit 280*a* determines that improper cassette loading has occurred.

As shown, in some embodiments, the processing unit 280*a* can receive data from one or more air sensors 144 in communication with outlet tube 55 attached to the cassette outlet 54. An air sensor 144 can be an ultrasonic sensor configured to measure or detect air or an amount of air in or adjacent to the outlet 54 or outlet tube 55. In normal operation, this air content data falls within an expected range, and the processing unit 280*a* can determine that proper fluid flow is in progress. When the air content data falls outside the expected range, the processing unit 280*a* can determine that improper air content is being delivered to the patient.

Processing unit 280*a* can continuously or periodically communicate with an independent and separate processor or processing unit 280*b* to communicate information to the user and/or to receive data from the user that may affect pumping conditions or parameters. For example, processing unit 280*a* can communicate by wire or wirelessly with processing unit 280*b* which can be configured as a user interface processor or controller (UIC) to control the output and input of display/input device 200, including by displaying an operating condition and/or activate indicator 18 to communicate with a user. In some embodiments, processing unit 280*b* can receive user input regarding pumping conditions or parameters, provide drug library and drug compatibility information, alert a user to a problem or a pumping condition, provide an alarm, provide a message to a user (e.g., instructing a user to check the line or attach more fluid), and/or receive and communication information that modifies or halts operation of the pump 10.

An independent and separate processor or processing unit 280*c* can be configured as a communications engine (CE) for the pump, a pump communications driver, a pump communications module, and/or a pump communications processor. Processing unit 280*c* can continuously or periodically communicate with processing units 280*a* and 280*b* to transmit and/or receive information to and from electronic sources or destinations separate from, outside of, and/or remote from, the pump 10. As shown, processing unit 280*c* can be in electronic communication with or include a memory 284 and program code 286, and processing unit 280*c* can be in communication with and control data flow to and from a communicator 283 which can be configured to communicate, wired or wirelessly, with another electronic entity that it separate from the pump 10, such as a separate or remote user, a server, a hospital electronic medical records system, a remote healthcare provider, a router, another pump, a mobile electronic device, a near field communication (NFC) device such as a radio-frequency identification (RFID) device, and/or a central computer controlling and/or monitoring multiple pumps 10, etc. The communicator 283 can be or can comprise one or more of a wire, a bus, a receiver, a transmitter, a transceiver, a modem, a codec, an antenna, a buffer, a multiplexer, a network interface, a router, and/or a hub, etc. The communicator 283 can communicate with another electronic entity in any suitable manner, such as by wire, short-range wireless protocol (Wi-Fi, Bluetooth, ZigBee, etc.), fiber optic cable, cellular data, satellite transmission, and/or any other appropriate electronic medium.

As shown schematically in FIG. 3, a pump 10 can be provided with many components to accomplish controlled pumping of medical fluid from one or more medical fluid sources to a patient. For example, one or more processors or processing units 280 can receive various data useful for the processing unit(s) 280 to calculate and output the operating conditions of pump 10. The processing unit(s) 280 can retrieve the program code 286 from memory 284 and apply it to the data received from various sensors and devices of pump 10, and generate output(s). The output(s) are used to communicate to the user by the processing unit 280*b*, to activate and regulate the pump driver by the processing unit 280*a*, and to communicate with other electronic devices using processing unit 280*c*.

Additional Features

In some embodiments, the pump 10 can be provided with an internal computer program code 286 included within memory 284 in electronic communication with, or within, on, and/or otherwise part of, the processing unit 280B of the UIC to control the output and input of display/input device 200. As shown in FIGS. 4A-9, the internal computer program code 286 can include steps, instructions, algorithms, and/or data configured to provide a text and/or graphical display 400 to provide information to and receive input from a user.

Figure 4A:
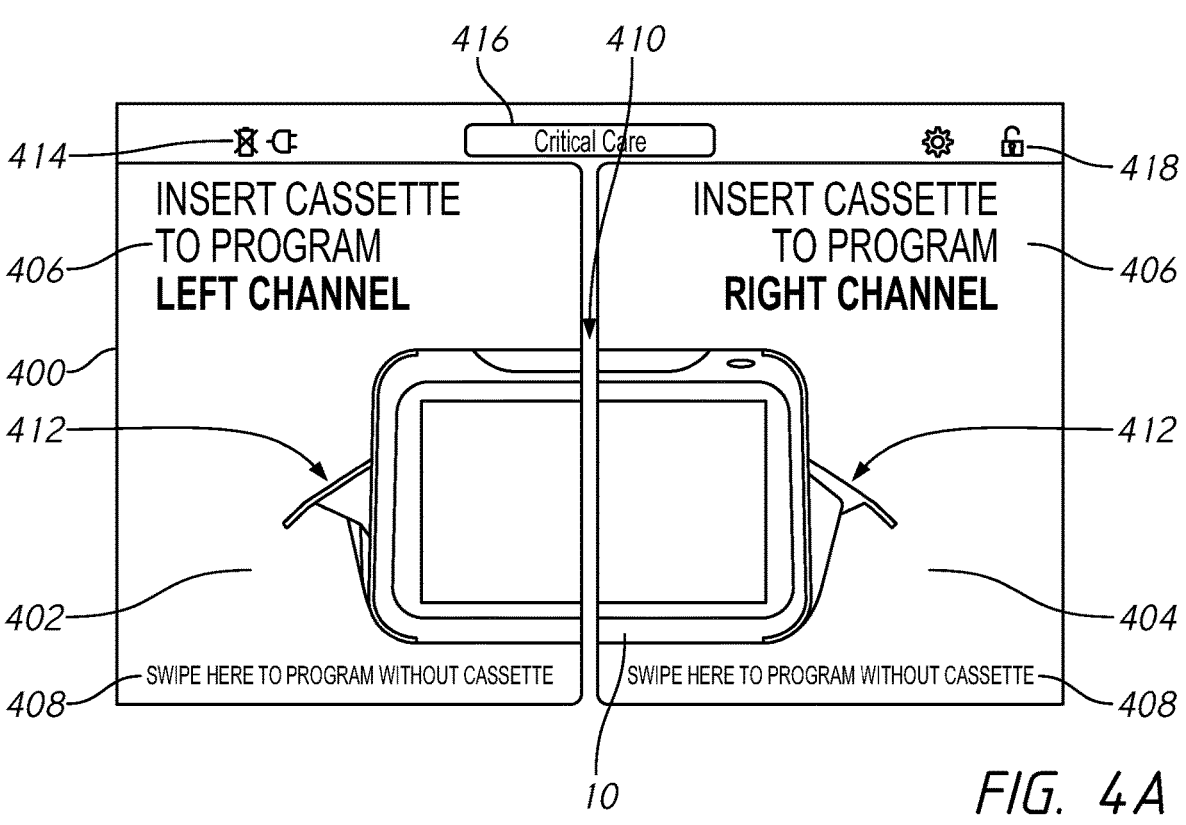
FIGS. 4A-4F show an example of a graphical user interface of a user communicator, such as display/input device, urging a user to insert a cassette into the pump driver.
Figure 4B:
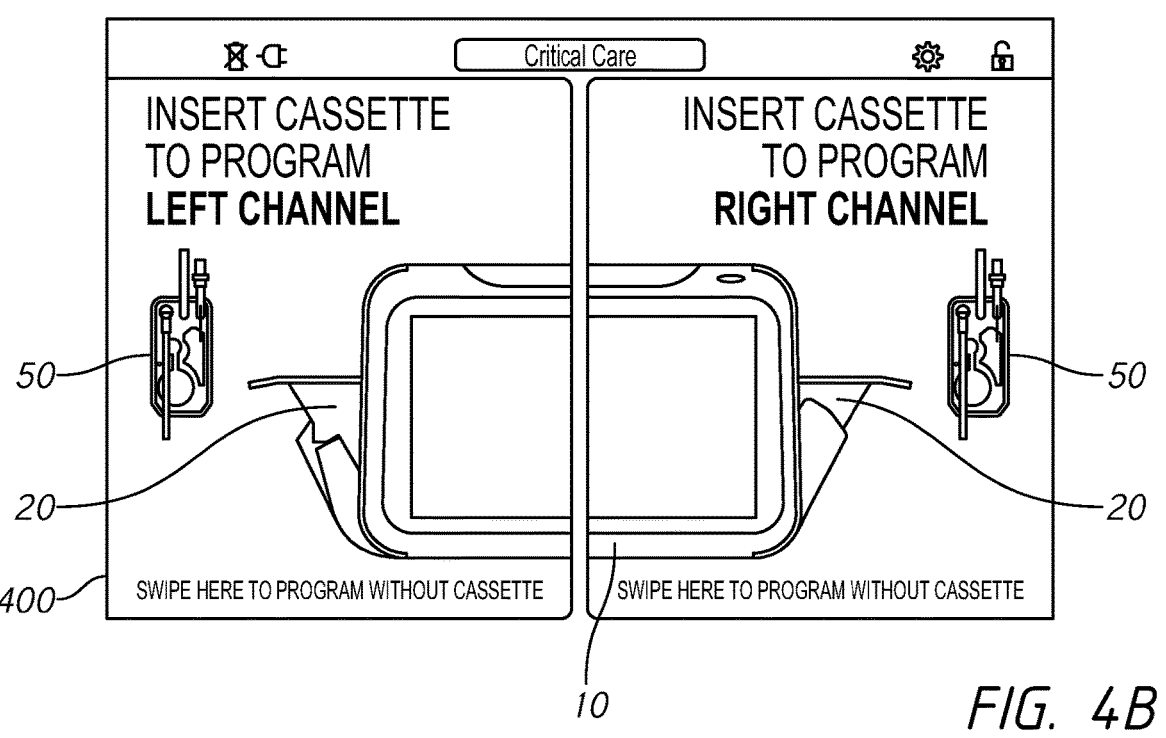
Figure 4C:
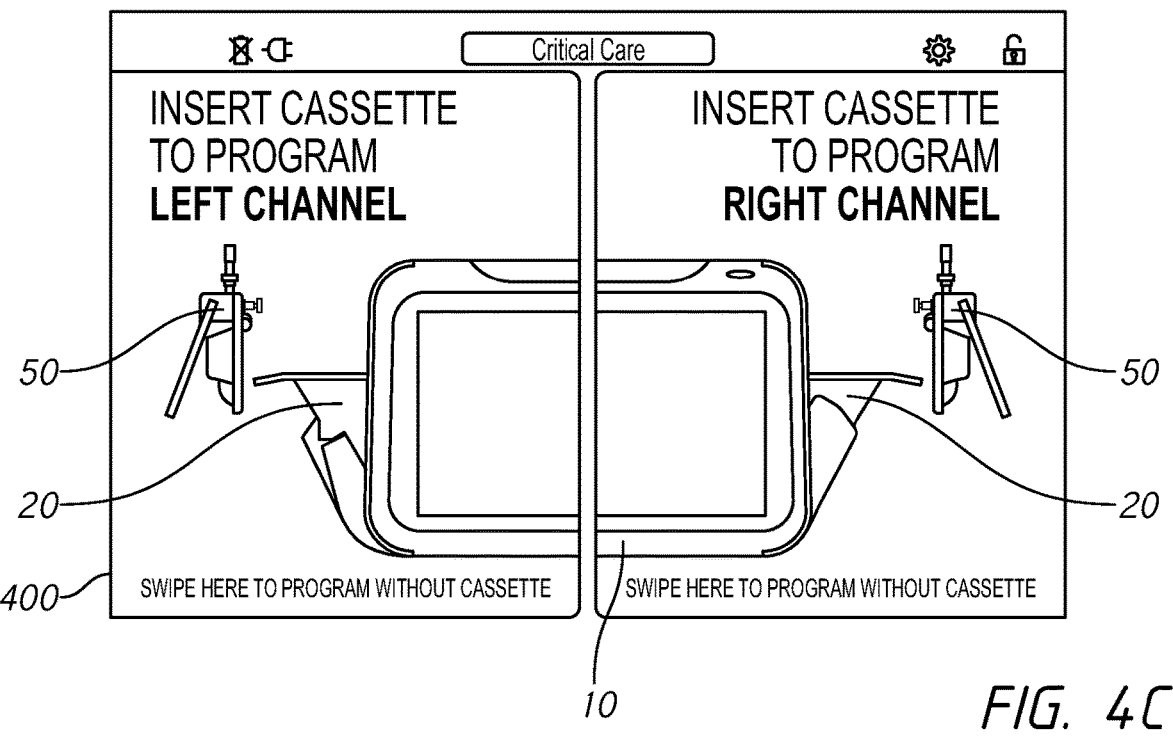
Figure 4D:
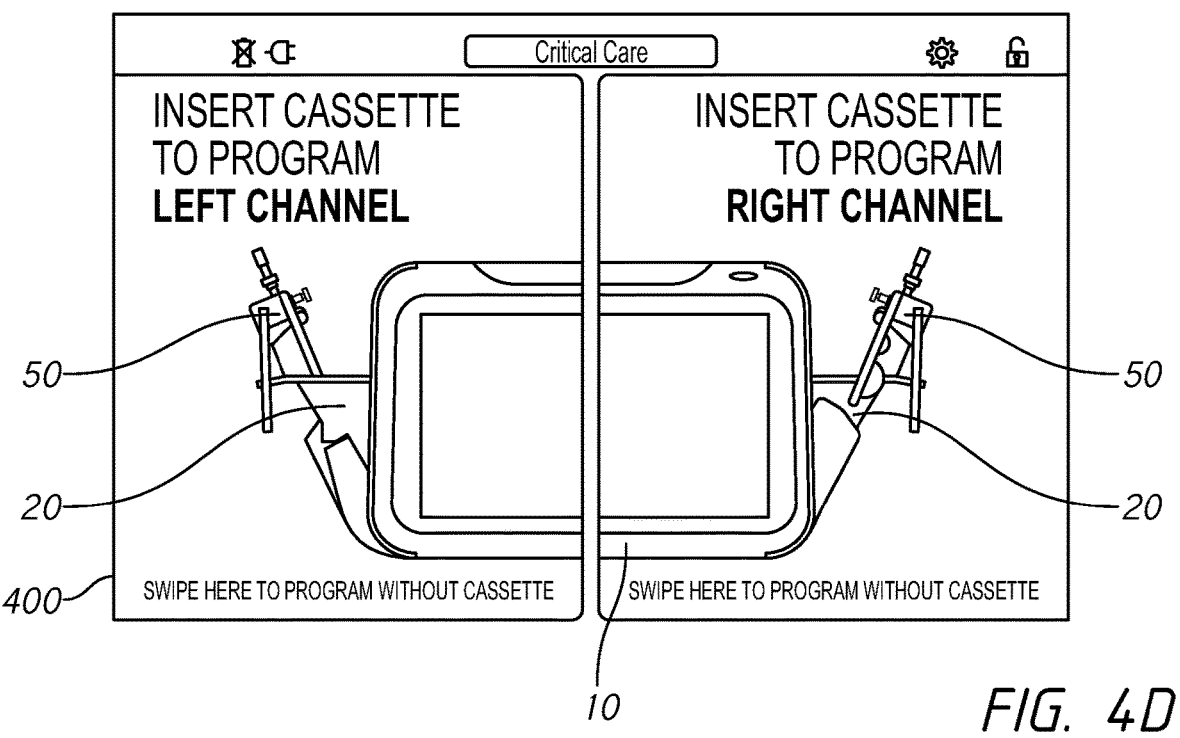
Figure 4E:
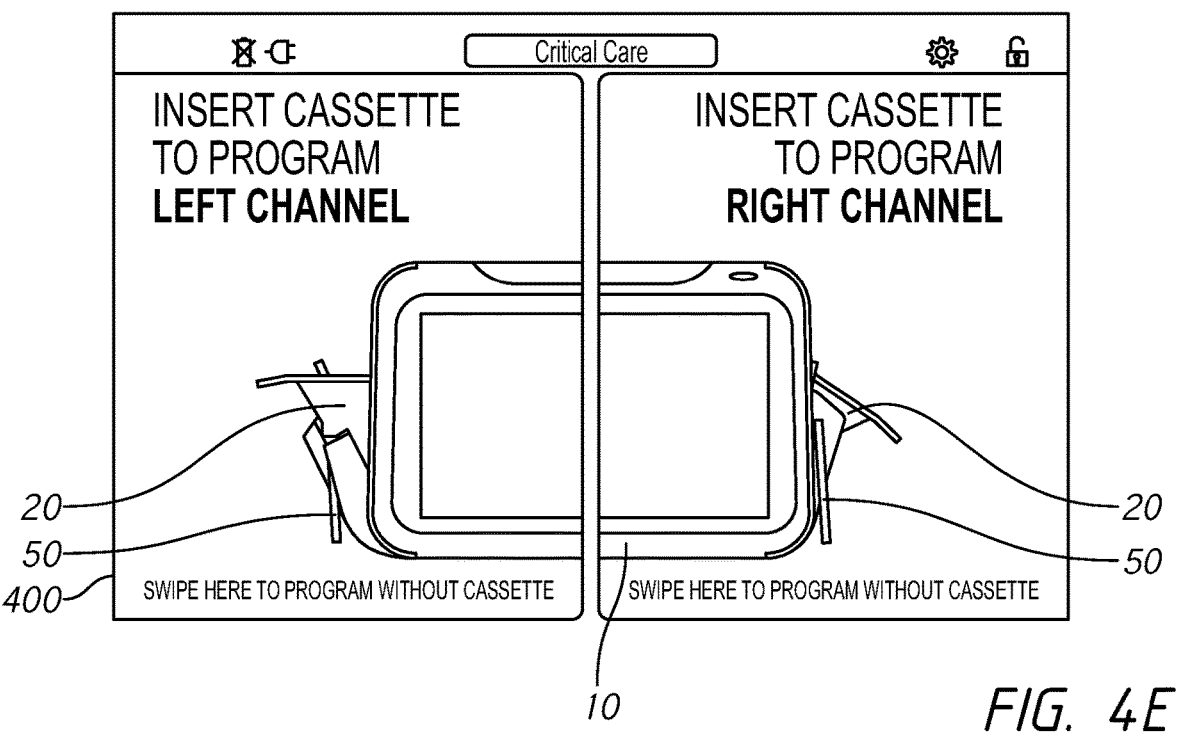
Figure 4F:
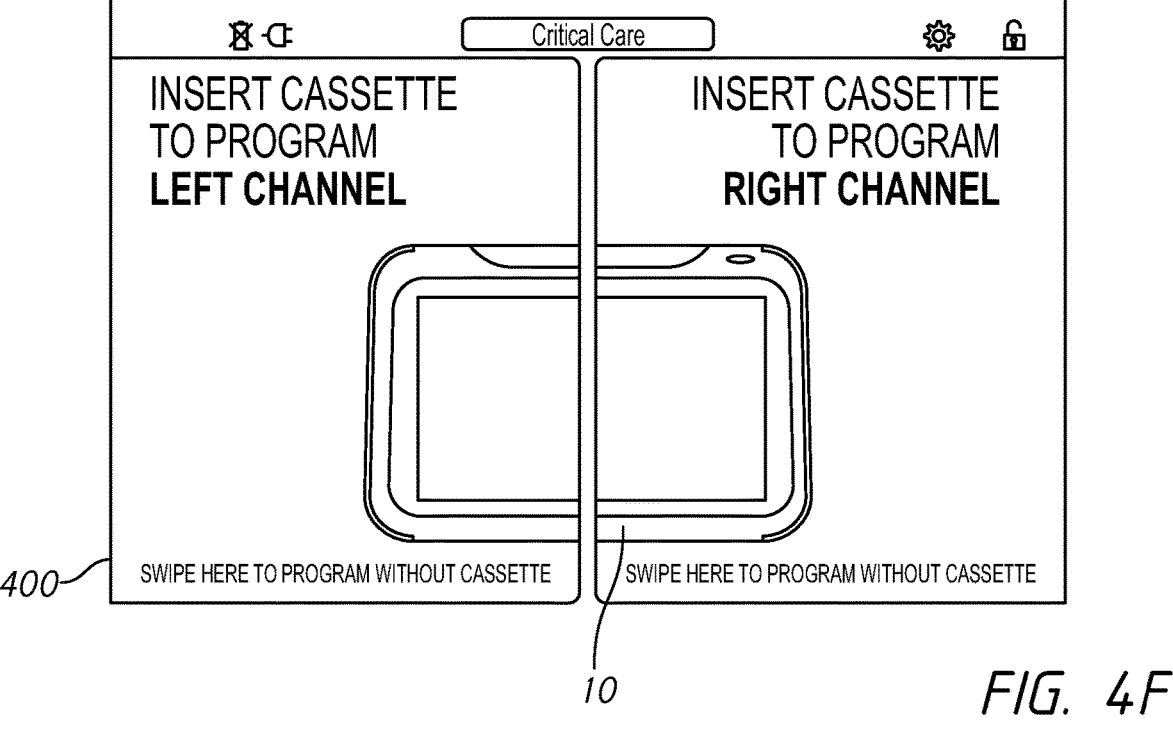

As shown in FIG. 4A, the display 400 on the display/input device 200 can comprise multiple display and/or input regions, such as a first region 402 and a second region 404. The first and second regions 402, 404 can be spatially separated from each other in a meaningful way that communicates useful information to a user. For example, the first region 402 can be located on the left side of the display 400 so that it is closest to the pump driver 14 on the left side of the pump 10, and the second region 404 can be located on the right side of the display 400 so that it is closest to the pump driver 14 on the right side of the pump 10. The first region 402 can be configured to receive and/or display relevant information about the left pump driver 14, and the second region 404 can be configured to receive and/or display relevant information about the right pump driver 14. Positioning each region 402, 404 of the display device 200 closest to the pump driver 14 as to which it receives and/or displays information enables the user to readily recognize which data entry or information display corresponds to which physical cassette(s) 50 and/or fluid source(s) (e.g., one or more IV bags or vials). As shown, text can be provided to communicate or emphasize to the user the pump driver 14 that each region 404, 404 controls, such as "Left Channel" and "Right Channel."

The left and/or right indicators 18 can be controlled by the processing unit 280B of the UIC to selectively illuminate, such as to illuminate to indicate that instructions are being provided or information is being received regarding the pump driver 14 adjacent to such illuminated indicator 18 and/or that such pump driver 14 is actively pumping medical fluid from a fluid source toward a patient. The left and right indicators 18 can be controlled by the processing unit 280B to communicate additional or different information, such as by selectively illuminating in multiple colors and/or by flashing to indicate an operational state (e.g., green and/or steady light) or a warning or disabled state (e.g., red and/or flashing light).

As illustrated, in some embodiments, when a cassette 50 has not been properly installed into one or more of the pump drivers 14, one or more position sensors in the pump driver 14 without the cassette 50 can detect the absence of the cassette 50 and communicate this information to the processing unit 280B, which can then cause display 400 to communicate an instruction 406 to the user through the first and/or second regions 402, 404 that notifies the user that no cassette 50 is currently inserted, that requests that the user insert a cassette 50 into the pump, and/or that disables the entering of information and/or that disables programming a course of infusion for such pump driver 14 unless or until the cassette 50 is properly inserted. For example, in some embodiments, the first and/or second regions 402, 404 can display text with such an instruction 406 or notice (e.g., as shown, "Insert Cassette to Program" Left and/or Right "Channel").

In some embodiments, as shown, the processing unit 280B can be configured to access from the electronic memory 284 in communication with the processing unit 280B one or a plurality of images comprising a display with moving graphics and/or an animation 410 to help notify or instruct the user that a cassette 50 needs to be inserted into the loader 20 of the pump driver 14 and/or to show how to insert the cassette 50 into the loader 20 of the pump driver 14. For example, as illustrated in FIG. 4A, a graphic and/or an animation 410 can comprise a schematic illustration of the pump 10 and/or cassette 50. In some embodiments, when a cassette 50 is not inserted into a respective pump driver 14, the graphic and/or animation 410 can illustrate the pump driver 14 in a state without the cassette 50. For example, as shown, the graphic and/or animation 410 can illustrate a portion of the loader 20 of the pump 10 in an open and/or extended position 412.

As shown in a comparison between FIGS. 4A-4F, a continuously looped, repeating sequence of changing graphics and/or an animation 410 can provide an engaging and effective way of notifying and/or instructing a user to insert the cassette 50 into the loader 20 of the pump driver 14 in the proper location before use. For example, the changing graphics and/or the animation 410 can comprise a schematic representation of the cassette 50 initially spaced away from the pump 10 (e.g., FIG. 4B), later brought near to the respective loader 20 of the pump driver 14 (e.g., FIG. 4C), and then inserted into the loader 20 of the pump driver 14 (e.g., FIGS. 4D and 4E). The pump 10 can then be shown with the loader 20 in a closed or retracted position (e.g., FIG. 4F). The animated motion of the cassette 50 and the loader 20 of the pump driver 14 can be shown to schematically repeatedly change from an open and/or extended position to a closed and/or contracted position, as shown, thereby urging the user to insert the cassette 50 into the loader 20 of the pump 10. The one or more position sensors in the pump driver 14 can detect when the user properly inserts the cassette 50 into the pump 10 and communicate a signal to the processing unit 280B of the UIC, causing the UIC to automatically change the display 400 to cease showing the graphic and/or animation 410 and automatically proceed to a screen on the display 400 where a user can input and/or view pumping information and/or parameters. In displays 400 that include multiple regions 402, 404, as shown, the processing unit 280B can cause the UIC to change the display only in the region 402, 404 corresponding to the pump driver 14 in which the cassette 50 has been inserted, leaving the other region 402, 404 to continue displaying all or part (as shown) of the graphic and/or animation 410 urging the user to insert the cassette 50 into the other pump driver 14 corresponding to the other region 402, 404. After or when the user inserts the cassette 50 into either loader 20 of either pump driver 14, the processing unit 280B can automatically transition the display 400 corresponding to that pump driver 14 to a screen permitting the user to make one or more selections relating to inputting and/or confirming information regarding a patient, a medical fluid to be infused, and/or parameters relating to a course of infusion, as illustrated in FIG. 5.

As shown in FIG. 4A, either or both of the regions 402, 404 of the display 400 can provide an instruction 408 or notice about the absence of the cassette 50, and/or can provide an input location and/or another way for the user to override the instruction 408 or notice about the absence of the cassette 50 and then permit the user to proceed to enter and/or program information into the region 402, 404 corresponding to a respective pump driver 14. For example, as shown, the region 402, 404 can display an overriding message indicating "Swipe Here to Program Without Cassette" or any similar message, and that area of the region 402, 404 can be configured to receive a swiping or other user input to permit entering information or programming without a cassette 50. In most situations, the infusion of fluid cannot begin without a cassette 50 inserted into the pump 10, but once programmed the pump 10 stands ready for infusion to begin immediately upon insertion of the cassette 50 if the user has overridden the instruction 406 or notice and previously entered pumping information before insertion of the cassette 50 into the pump 10.

This initial stage of use or initial screen and/or other screens for the display 400 can include one or more other items or features to convey useful information to a user and/or to receive input from a user. For example, as shown, the display 400 can communicate to the user information about the electrical power source of the pump 10, using a power indicator 414. For example, the power indicator 414 can inform the user whether the pump 10 is in electrical communication with an external power source. In the example shown, the display 400 is communicating to the user that the battery 94 of the pump 10 does not have sufficient electrical power to operate the pump 10 (or is not attached) and an external power source is connected to the pump 10. The display 400 can alternatively be configured to display a message and/or graphic indicating that the pump 10 is not attached to an external power source and is operating using the electrical power from the onboard battery 94, or that the pump 10 is attached and capable of receiving electrical power from both the battery 94 and an external power source. The power indicator can in some embodiments show numerically and/or graphically how much electrical power remains in the battery 94.

The display 400 can provide information communicating to the user a mission message 416 showing a temporarily and selectively changeable assigned purpose, location, department, owner, and/or task for the pump 10. For example, as illustrated, the mission message 416 indicates "Critical Care," demonstrating that the pump 10 is temporarily assigned for use in a critical care department of a hospital. The mission message 416 can be inputted by a local user of the pump 10 and/or can be inputted remotely by a user and/or a computer system in communication with the pump 10 through the communicator 283 in communication with the processing unit 280C of the CE. In some embodiments, the pump 10 can include a position or location sensor, such as a GPS sensor, an NFC/RFID device, and/or a wired or wireless (e.g., WiFi-enabled) sensor, that is configured automatically to determine the location of the pump 10 and/or automatically to display and/or change, without input from a local user, the mission message 416 to reflect the purpose, location, department, owner, and/or task for the pump 10, as correlated or inferred from its location. For example, the mission message 416 can be configured to automatically display as "Critical Care" when the pump 10 is powered up or activated in the location of the critical care department of the hospital and/or to change from displaying one location (e.g., "Critical Care") to displaying another location (e.g., "Pediatric") when the pump 10 is moved from one location of the hospital (e.g., the critical care location) to another location of the hospital (e.g., the pediatric location). The display 400 can include a security indicator 418 showing whether the pump 10 is in a locked state (e.g., prevented from providing and/or receiving one or more types or all information and/or instructions from a user), or an unlocked state (e.g., permitted to provide and/or receive one or more types or all instructions and/or instructions from a user).

As illustrated in FIG. 5, the display 400 can prompt a user to input information in the first and second regions 402, 404 for separate pump drivers 14. The type of information shown and received in the respective first and second regions 402, 404 can be different for each one. For example, if a cassette 50 has not been inserted into one of the first and second pump drivers 14, the respective corresponding first or second region 402, 404 can remain as shown in FIGS. 4A-4F, while at the same time if a cassette 50 has been inserted into the other of the first and second pump drivers 14, the respective corresponding other first or second region 402, 404 can automatically transition to the screen shown in that region in FIG. 5. As shown, the screens displayed in the first and second regions 402, 404 can be split, operating in different stages from each other, depending on their different circumstances.

In some embodiments, as shown, each of the pump drivers 14 and cassettes 50 can be configured to receive and/or be coupled with multiple sources of medical fluid. For example, the left pump driver 14 can be configured to receive and/or be coupled with a primary and a secondary line or tube of incoming medical fluid from at least two medical fluid sources, and the right pump driver 14 can be configured to receive and/or be coupled with a primary and a secondary line or tube of incoming medical fluid from at least two medical fluid sources. Each of the pump drivers 14 can intermittently, alternatively, generally continuously, and/or generally simultaneously deliver multiple fluid sources to a patient. The capability of receiving and conveying to a patient a plurality of fluid sources through a single pump driver and cassette is described and illustrated in U.S. Pat. No. 4,842,584, previously incorporated by reference in its entirety in this application, and any structure, material, function, method, or step that is described and/or illustrated in that patent for doing so can be used with or instead of any structure, material, function, method, or step that is described and/or illustrated in this specification.

As shown in FIG. 5, the processing unit 280B can retrieve from its memory 284 and display on the display/input device 200 a graphical user interface that is configured to permit a user of the pump 10 to select to input and/or view pumping information from at least a first pump driver 14 and cassette 50 represented in the first region 402, and a second pump driver 14 and cassette 50 represented in the second region 402. In each of the first and second regions 402, 404, an association graphic 420 can help associate in a user's mind the correlation between the user's selection and the respective pump driver 14 and cassette 50 to which it applies. For example, the association graphic 420 can comprise an arrow as shown, and/or any other spatial and/or directional indicator (e.g., a line, a circle, a triangle, etc.), to denote and/or to point the user in the direction of the pump driver 14 and cassette 50 as to which the selection applies. Each of the first and second regions 402, 404 can include association text 422 describing the location and/or other identifier of the corresponding pump driver 14 and/or cassette. For example, in some embodiments as shown, the association text 422 can specify "Left Cassette" and/or "Right Cassette."

Each of the first and second regions 402, 404 can include a product graphic 424 that schematically illustrates one or more physical products or portions thereof in each respective pumping line, such as a cassette 50 and/or tubing as shown, to help show and/or remind the user how information to be inputted or viewed relates to the physical pump driver 14 and cassette 50 connections made by the user on the pump 10. The product graphic 424 can include one or more depictions of shapes and/or properties of the cassette 50, fluid source, one or more fluid line components, and/or a pump driver 14, etc. For example, as shown, the product graphic 424 in some embodiments can include one or more depictions of the cassette 50, tubing, a drip chamber, a needle-free connector, and/or a patient output line, etc. The product graphic 424 can include one or more connection points 426, 428 to help associate and/or correlate the region of a user's selection with the corresponding physical configuration of the tubing and/or connections or fluid communication between the cassette 50 and one or more medical fluid sources. Any portion or region of the display 400 can be configured as a sensing region that is capable of detecting a user's touch selection in such region and/or generating an electronic signal transmitted to the processing unit 280B to indicate a user selection relating to that region. For example, as illustrated, a primary connection point 426 can illustrate that the information to be inputted or viewed when a user selects and/or touches a first sub-region 430 (e.g., "Left Primary Line—L1" or "Right Primary Line—R1") will affect and/or display pumping parameters on the illustrated one of a plurality of lines of the physical cassette 50 that touches (as shown), is within, is near, and/or is adjacent to, this sub-region 430 on the display 400 at the primary connection point 426. A secondary connection point 428 can illustrate that the information to be inputted or viewed when a user selects and/or touches a second sub-region 432 (e.g., "Left Secondary Line—L2" or "Right Secondary Line— R2") will affect and/or display pumping parameters on the illustrated one of a plurality of lines of the physical cassette 50 that touches (as shown), is within, is near, and/or is adjacent to, this sub-region 432 on the display 400 at the secondary connection point 428. When a user touches any of the sub-regions 430, 432, the display/input device 200 is configured to convey an electrical signal to the processing unit 280B which is configured to change the screen by retrieving instructions and/or data from its memory 284 to permit input and/or viewing of selected pumping data and/or parameters.

In some embodiments, as illustrated, one or more machine-readable codes 434 can be provided on the display 400 by the processing unit 280B to help coordinate information exchange between or among different computer systems. For example, as illustrated, a combination of dark and light regions (e.g., a QR code or a bar code) can encode information that can be read by an optical reader of another computer system that is aimed at and captures information from one or more of the machine-readable codes 434 on the display 400. The encoded information from the one or more machine-readable codes 434 can itself convey information to the other computer system about the configuration of the pump 10 and/or any or all related components (e.g., the cassette 50, tubing, etc.), and/or the encoded information can create a link of identifying information between or among one or more computer systems that can permit separate and independent communication of information through a different communication channel enabled by the link between or among such computer systems, using processing unit 280C and communicator 283.

As shown in FIGS. 6A-9, when a user selects and/or is directed into inputting and/or programming a particular pump driver 14, the processing unit 280B can retrieve from its memory 284 and/or its program code 286 information and/or data to enable the display/input device 200 to receive from the user and/or display to the user information relating to a course of pump infusion for that pump driver 14.

Figure 6A:
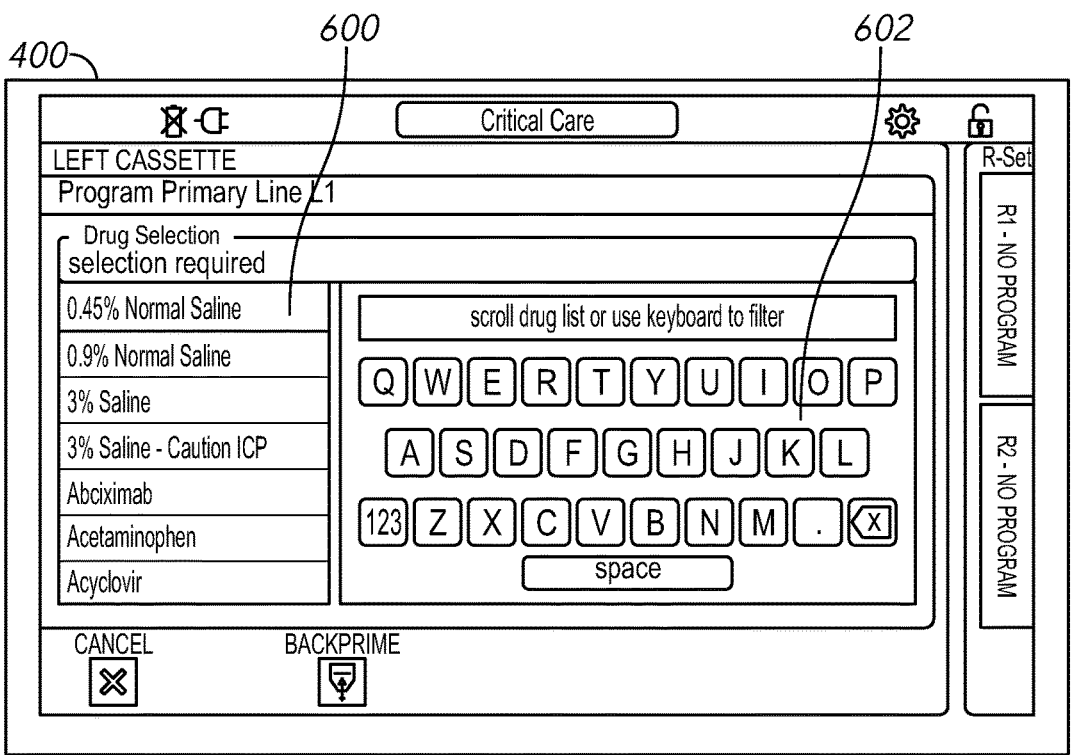
FIGS. 6A-8B show example of other graphical user interfaces of a user communicator, permitting a user to enter and/or to select parameters for medical fluid infusion.

For example, as illustrated, when a user touches sub-region 430 of the display 400 shown in FIG. 5, the display 400 can transition to a user input phase as in the example depicted in FIG. 6A. If a user instead touches another region or sub-region, the display 400 can be configured to transition to a user input phase specific to the information, prompts, and/or graphics depicted in that region or sub-region, such as for a different pump driver 14.

As shown in FIG. 6A, in some embodiments, the display 400 can be configured to provide a user interface that requests the user to input or otherwise identify the drug to be infused into the patient through the pump driver 14 associated with the user's choice. For example, the display 400 can provide a scrollable or otherwise selectable list of a plurality of possible drug choices in one region of the display 400 and/or the display 400 can permit the user to input a drug choice using a keyboard, such as a virtual touch-screen keyboard 602 as shown. Any other suitable input mode, such as any used in any embodiment anywhere in this specification, can be used to receive information or one or more selections from a user, such as a series of buttons, a physical keyboard, a mobile electronic device in electronic communication with the pump 10, a microphone in electronic communication with a voice-recognition system within or in electronic communication with the pump 10, and/or a camera capable of viewing one or more gestures from the user, etc. As shown, the selectable list of possible drug choices can include one or more additional data items regarding a drug, such as the concentration of the drug and/or one or more constituents of the drug, and/or information or warnings regarding the drug.

Figure 6B:
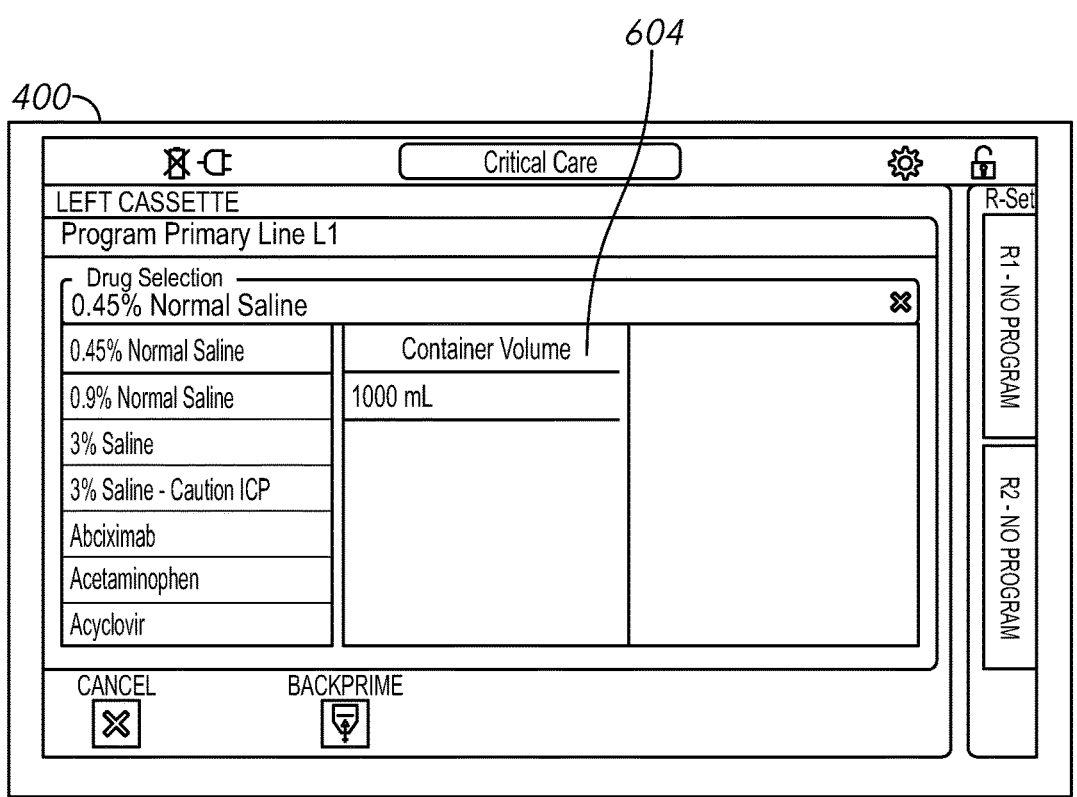

The display 400 can include a user prompt or input 604 and/or can be configured to receive an input or selection from the user of one or more other items of information regarding a particular course of medical fluid infusion (instead of or in addition to the drug selection as shown in FIG. 6A). For example, as illustrated in FIG. 6B, the display 400 can be configured to prompt and/or receive an input from the user regarding one or more features of a drug to be infused, such as the total volume of the drug contained within the medical fluid source that is attached to the cartridge 50 coupled to the pump driver 14 associated with this display stage, as shown. In some embodiments, the user can be prompted to input or select the concentration of the drug, the manufacturer of the drug, one or more variants of the drug, and/or the date of manufacture of the drug, etc. As shown, some commonly used or suggested possibilities can be provided as defaults, such as in a drop-down selection region or in any other way, or the user can be permitted to enter one or more values, including values that may be different from those suggested.

Figure 7A:
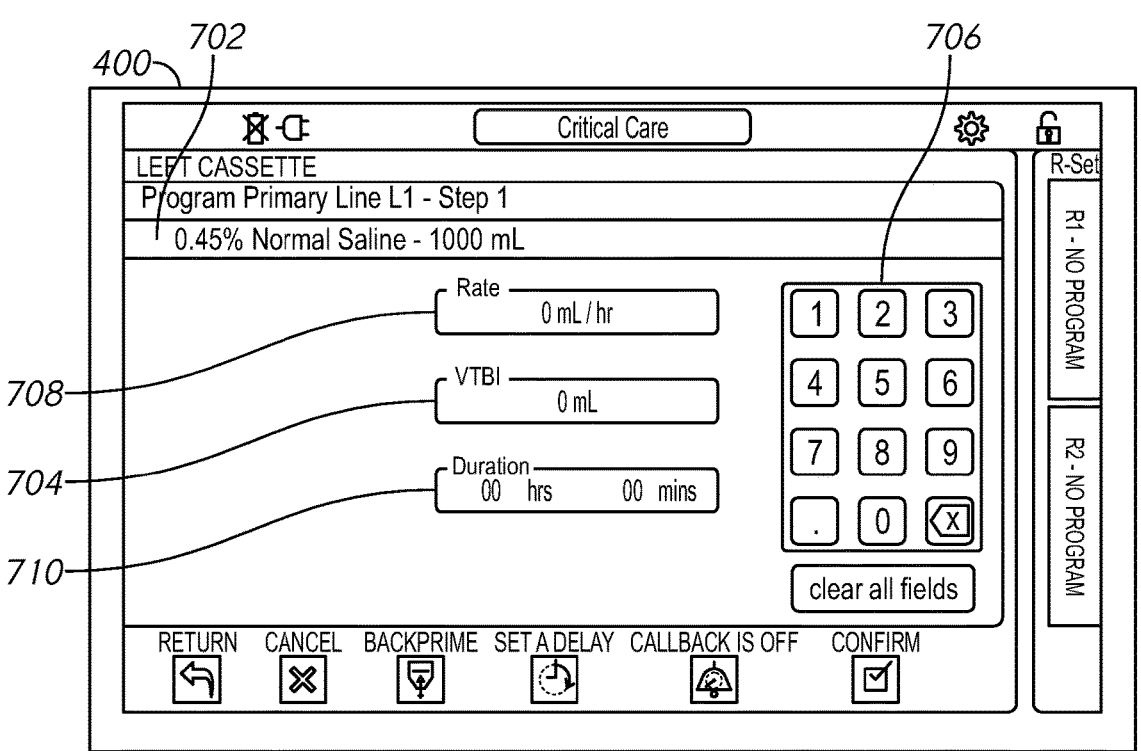

The display 400 can be configured to permit the user to specify or pre-program multiple steps in a course of infusion with one or more pumping parameters or variables that can automatically change when a pre-determined time elapses or when some other aspect of the pumping course has been accomplished, such as the pumping of a pre-determined volume of fluid, without requiring the user to return to the pump 10 to change the pumping parameters. For example, a user can indicate that a first step can proceed at a higher infusion rate and then transition to a second step at a lower infusion rate. Each step can be configured to last for a user-specified amount of time. As shown in FIG. 7A, the display 400 can be configured to permit the user to enter a single, unchanging pumping course or to permit a user to enter multiple, sequential, and/or consecutive steps in a pumping course, with each different step changing at least one pumping parameter.

As illustrated in FIG. 7A, in some embodiments, the display 400 can be configured to prompt a user to input a plurality of items of information relating to how the medical fluid will be infused into the patient, and/or the display 400 can be configured to receive at least one item of information relating to how the medical fluid will be infused into the patient and/or either of the processors 280A or 280B can be configured to provide one or more defaults of pumping information or parameters, and/or can be configured to calculate and/or to derive one or more other items of pumping information or parameters from or relating to one or more inputs or selections made by the user.

For example, in some embodiments (not shown), the volume-to-be-infused (VTBI) into the patient can be auto-populated or initially set as a changeable default that is equal to the total volume of fluid that is contained within the fluid source container (e.g., as either previously inputted by the user, or as communicated electronically separately to the pump 10, and/or as calculated or derived by the pump 10), or that is equal to some pre-determined proportion or fraction of the total volume of fluid that is contained within the fluid source container (e.g., 90% of the total volume of fluid that is contained within the fluid source container).

Figure 7B:
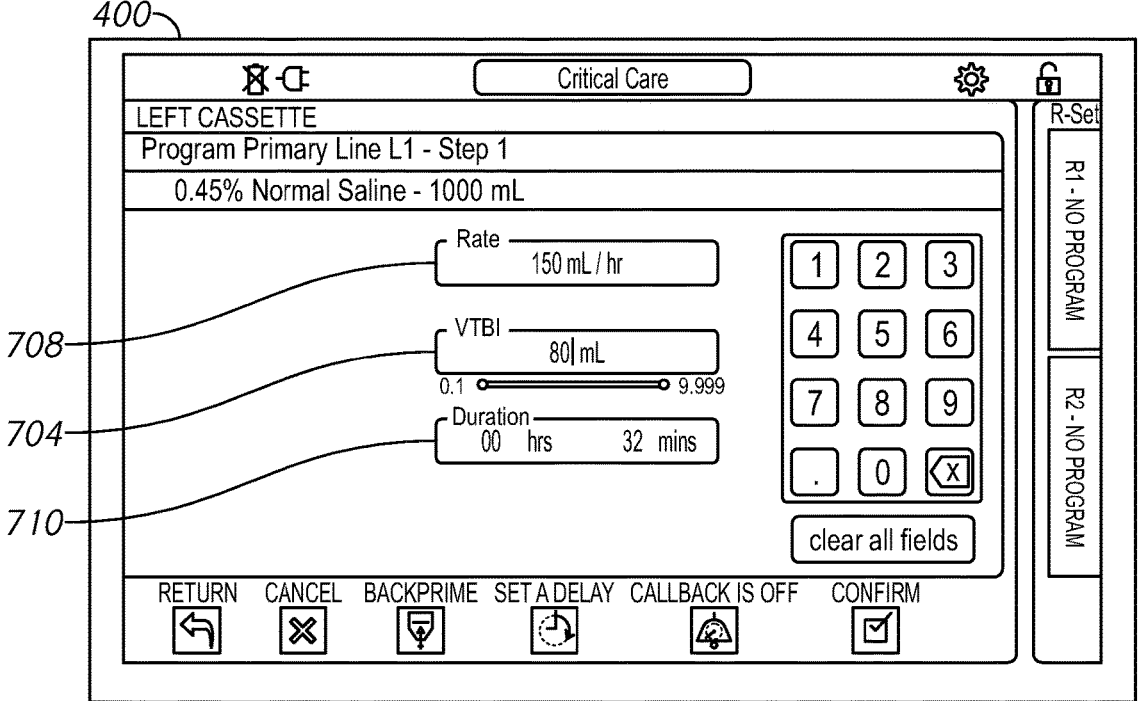

As another example, in some embodiments such as is shown in FIG. 7B, certain parameters can be calculated and/or derived by the processor 280B from inputs of one or more other parameters, such as calculating and/or deriving the pumping duration time from the pumping rate and the VTBI. In the example shown in FIG. 7A, the display 400 can be configured to provide a user input (e.g., a touch-screen keyboard 706 on the display 400, as shown) to allow the user to input a first value, such as the rate at which the fluid from the fluid source container will be pumped by the pump driver 14 into the user (e.g., in volume, such as milliliters, within a specified amount of time, such as hours), which can be shown on the display 400 in a rate display 708. The display 400 can be configured to allow the user to input a second value, such as the VTBI (e.g., in volume, such as milliliters), which can be shown on the display 400 in a volume display 704. As illustrated, when one or more pumping values (e.g., first and second values) are provided or set (e.g., rate and volume), the processor 280B can derive and/or calculate another pumping value (e.g., a third pumping value), such as the time for such volume to be pumped at the specified rate, which can then be displayed in the infusion duration display 710. In the example shown in FIG. 7B, in the processor 280B, the volume-to-be-infused of 80 mL (see volume display 704) is divided by the pumping rate of 150 mL/hr (see rate display 708) and then converted from hours to minutes, yielding a pumping duration of 32 minutes (see infusion duration display 710). Any other possible calculation and/or derivation can be used. As illustrated, the display 400 can include a selected drug indicator 702 to confirm to the user the name drug that was selected by the user previously. As illustrated, the display can show one or more hard or soft limits for certain pumping parameters. For example, as shown in FIG. 7B, a limit indicator (e.g., a bar and/or upper and lower values, as shown) is provided that shows a potential range for the VTBI. In some embodiments, no values outside of this range will be accepted (hard limit); and in some embodiments, values outside of this range will be accepted but a notice will be given to the user that the parameter is outside of the expected range (soft limit). A limit indicator can be provided for any pumping value, whether inputted by the user or received from a memory or from a remote source or calculated by the processor 280B. In some embodiments, such as where the infused fluid has a time constraint or requirement, the limit indicator can be provided on the infusion rate; and in some embodiments, such as where the infused fluid is intermittent or otherwise not time-constrained, the limit indicator can be provided on the VTBI, the duration, and/or the rate.

Figure 8A:
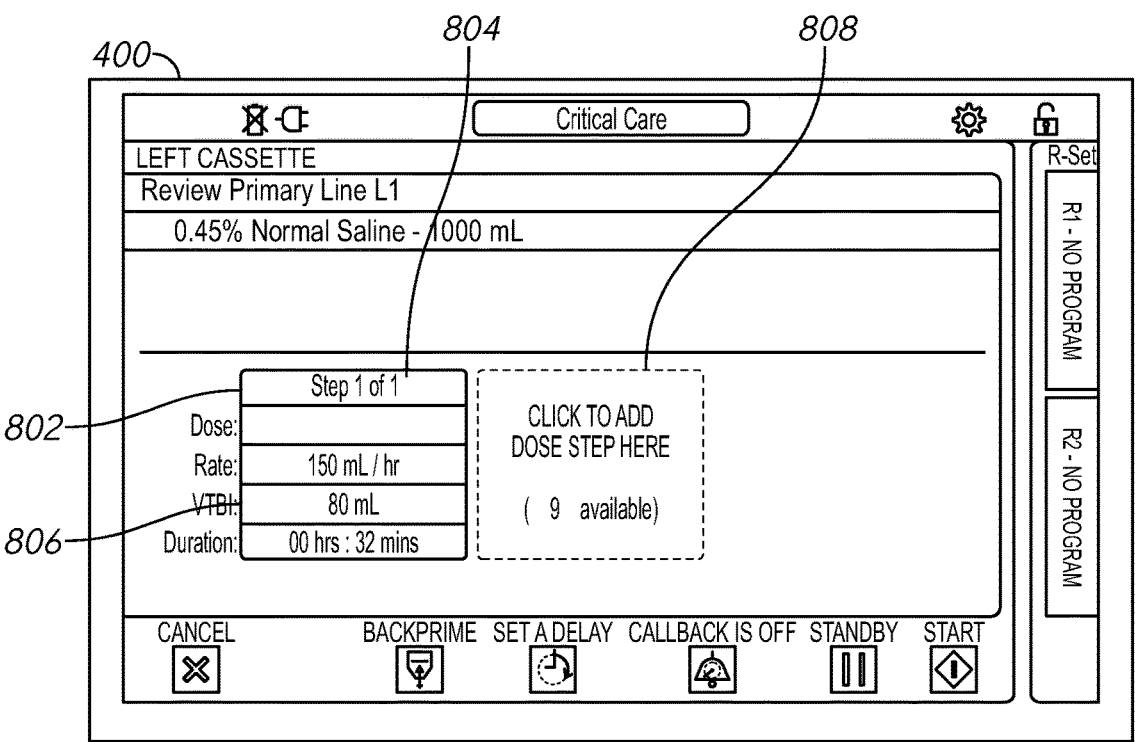

FIG. 8A illustrates that the programming or pumping parameters entered, confirmed, and/or set by the users in a particular stage or step, such as in the manner illustrated in FIGS. 7A-7B, and/or otherwise calculated and/or derived by and/or communicated to the pump 10 (for example, through wired or wireless electronic communication, e.g., using communicator 283 and/or processing unit 280C), can be shown on the display 400 in a summarized, distinct, discrete, encapsulated, separated, and/or grouped way. For instance, the display 400 can provide an infusion parameter grouping 802 that describes and/or represents at least one step or stage in an infusion course for a patient. The parameter grouping 802 can include a grouping label 804 that can identify the designated pumping parameters in any suitable way and/or describe how the parameter grouping 802 fits in with or is ordered in relation to other parameter groupings (see FIG. 8B), such as stating "Step 1 of 1." The parameter grouping 802 can display one or more pumping values or parameters 806. In the example shown, the parameter grouping 802 can include a boundary and can comprise a designated shape that is common to and/or generally the same as one or more additional parameter groupings, such as a generally square shape (as shown), a generally rectangular shape, a generally circular shape, etc. The display 400 can be configured to include an adding sub-region 808 that is configured to permit the user to specify one or more additional parameter groupings 802 that will be added and/or inserted after (or before) the one or more parameter groupings 802 already shown on the display 400. When a user actuates (such as through the touch screen) the adding sub-region 808, the display 400 can be configured to move to and/or return to a mode for receiving pumping parameters or values, such as shown in FIGS. 7A-7B, for that additional parameter grouping 802. One or more additional parameter grouping 802 can then be shown sequentially on the display 400 in a manner that represents the order of execution of the parameter groupings 802 during pumping.

Figure 8B:
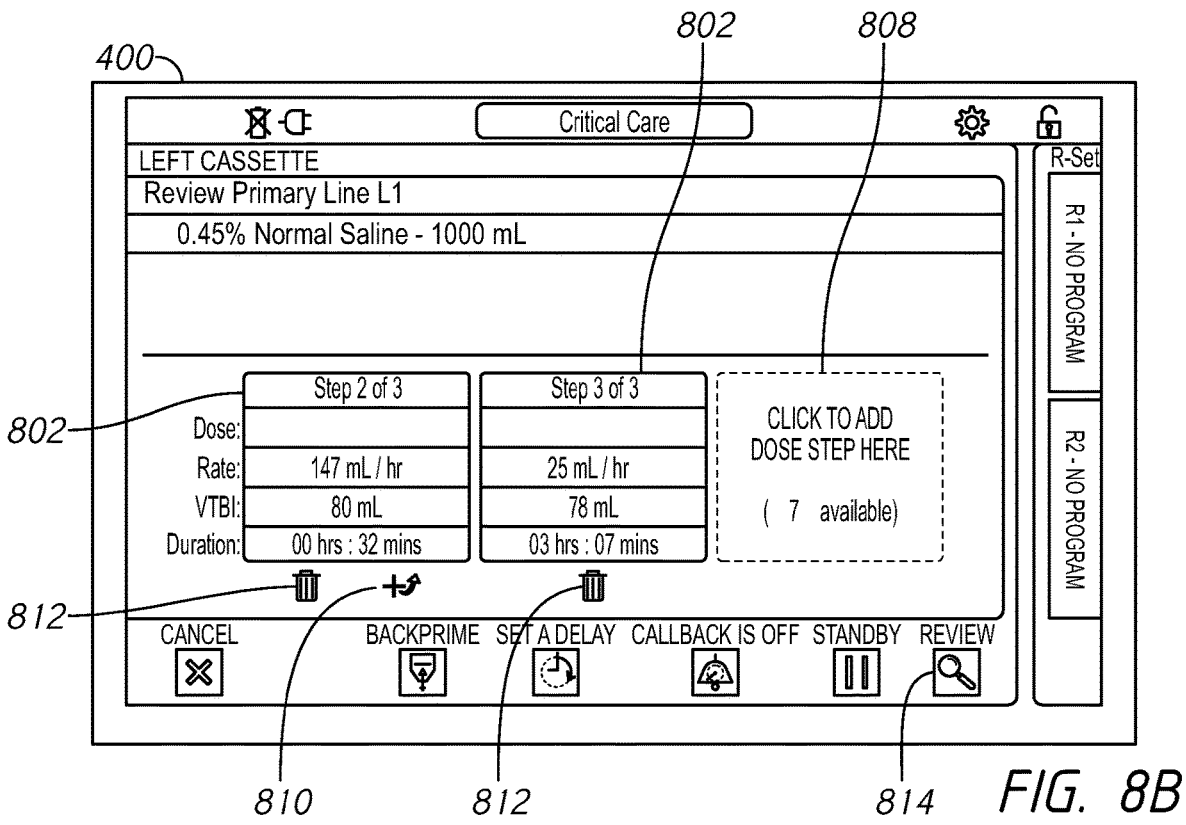

As shown in FIG. 8B, when a plurality of parameter groupings 802 are provided, each parameter grouping 802 can be shaped and can be sufficiently small in size such that multiple parameter groupings 802 can be viewed on the display 400 at the same time and/or can be sufficiently large to enable viewing of the details within each parameter grouping 802 by an average user without difficulty. In some embodiments, as shown in FIG. 8B, at least three parameter groupings 802 can be shown on the display 400 at the same time. More parameter groupings 802 can be programmed in and/or designated by a user, such as at least 8 or at least 10 parameter groupings 802. When not all parameter groupings 802 are shown on the display 400 at the same time, the display 400 can be configured to allow the user to select individual parameter groupings 802 or subsets of parameter groupings 802 for viewing, such as by scrolling horizontally and/or vertically through the parameter groupings 802 (e.g., by swiping back and forth and/or up and down on the touch screen on which the display 400 is shown).

Parameter groupings 802 can be edited as needed or desired before commencing a course of infusion and/or during a course of infusion (for parameter groupings 802 not yet executed). For example, as shown in FIG. 8B, a new parameter grouping 802 can be added for execution between two existing parameter groupings 802, such as by touching an addition icon 810 which can cause the display 400 to return to a mode for receiving pumping parameters or values, such as shown in FIGS. 7A-7B, for that additional parameter grouping 802, and which can cause that additional parameter grouping 802 to be positioned afterward on the display 400 between the two parameter groupings 802 where the addition icon 810 was located when touched. Any parameter grouping 802 can be deleted by a user by touching on a deletion icon 812 adjacent to and/or associated with a particular parameter grouping 802. When each of the desired parameter groupings 802 have been entered and/or set, a user can actuate the review icon 814 which can permit the user to recheck the accuracy and/or correctness of the pumping values and/or parameters in each parameter grouping 802, at which point the review icon 814 can change to a start icon (not shown). When the user actuates the start icon, the infusion of medical fluid can begin sequentially through and/or in accordance with each of the multiple pumping stages as specified in each consecutive parameter grouping 802. In some embodiments, as shown, the user is not permitted to start infusion until the user has first actuated the review icon 814 and/or the user has first caused each of the pumping stages in each parameter grouping 802 to appear on the screen to enable review by the user. The same or similar steps and/or graphical user interfaces can be utilized to input pumping values for any or all of the pump drivers 14, any or all of the input tubes 57 of the cassette 50 from different medical fluid sources, and/or any or all of the sub-regions 430, 432 (see, e.g., FIG. 5).

Figure 9:
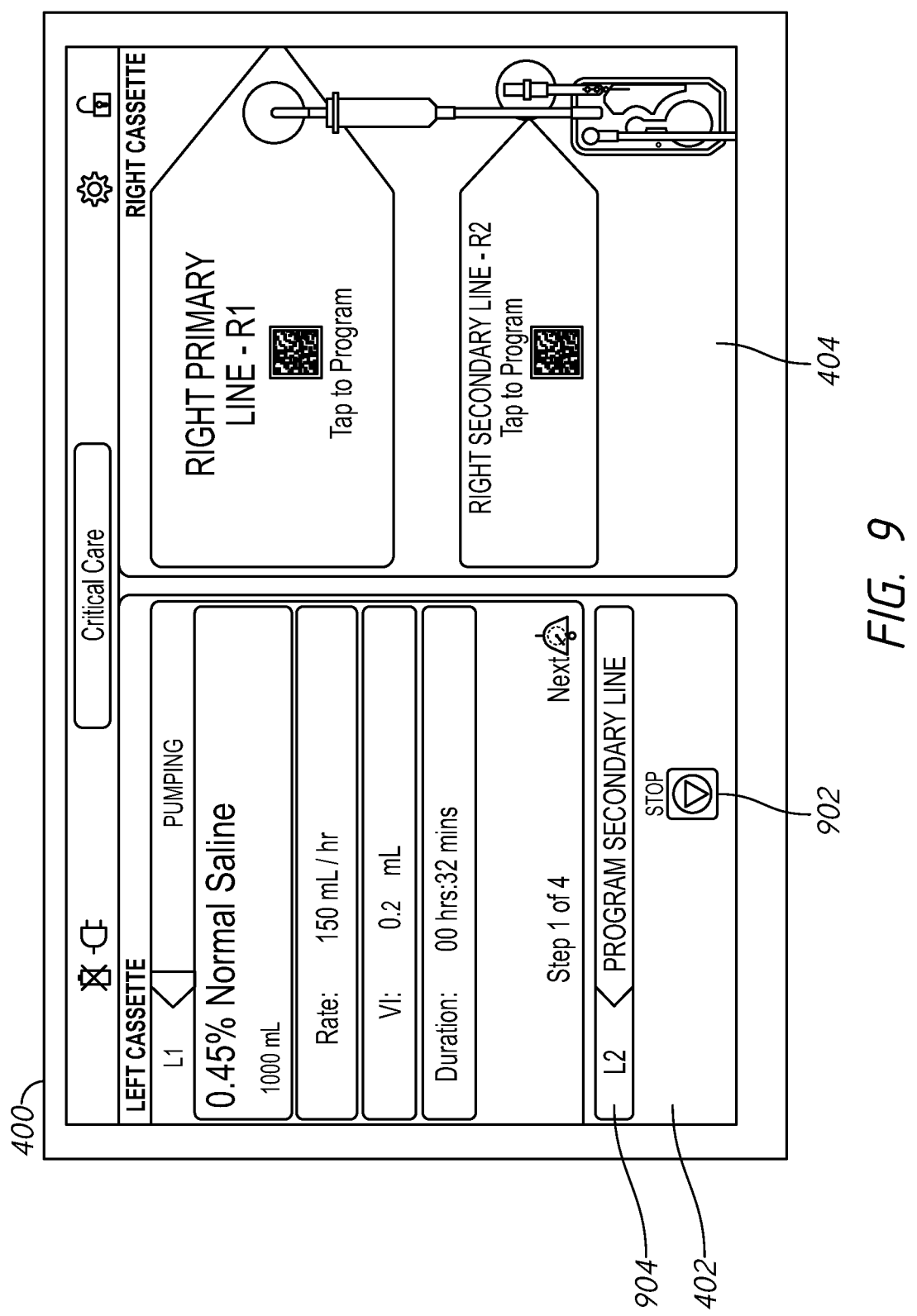
FIG. 9 shows an example of a graphic user interface of a user communicator during a pumping phase.

As illustrated in FIG. 9, when a previously programmed course of medical fluid infusion is commenced on a pump driver 14, the display 400 can show that such pump driver 14 is active and pumping, with a designation and/or description of the real-time pumping parameters, separate from and/or independent of the state of one or more other pump drivers 14. For example, as shown, the first region 402 can show that a first pump driver 14 (e.g., on the left) is active and pumping, while the second region 404 can show that a second pump driver 14 (e.g., on the right) is not active and is not pumping and that the second region 404 can be actuated (e.g., by touching) to enable programming of the second pump driver 14, such as is shown in FIG. 5. The pumping can be immediately stopped by actuating the stop icon 902. An additional (e.g., secondary) line for pump driver 14 corresponding to an additional (e.g., secondary) input tube 57 and/or another pump driver 14 (e.g., on the right) can be programmed by touching respectively in a sub-region 904 designated for such additional line and/or in a region or sub-region designated for such other pump driver 14, using any appropriate display mode, data input, communication, calculation, and/or derivation method or step, including but not limited to any or all of those illustrated and described in connection with FIGS. 5-8B.

In some embodiments, it is desirable to lock the display 400 from some or all user input to resist inadvertent contact by a user, a patient, medical equipment, and/or any other contact that could unintentionally be treated as an input of some kind by the pump 10. For example, the processor 280B can auto-lock the display 400, rendering it unresponsive to most or all touch contact after a predetermined period of time following a user touch of the screen, such as at least about 20 seconds and/or less than or equal to about 40 seconds. The processor 280B can auto-lock the display 400 in any other suitable situation when the risk of inadvertent screen contact is high, such as: when one or more motion and/or location sensors in the pump 10 (e.g., a GPS sensor, an accelerometer, a WiFi locator, an acoustic sensor, an infrared sensor, etc.) detect that the pump 10 is being moved; when the electrical cable 92 is removed from an electrical outlet and the pump 10 transitions to receiving only electrical power from its onboard battery 94 (which may suggest that the pump 10 is about to be moved); and/or when a series of touches, movements, and/or other contact on the screen indicate by their nature (e.g. repetition, extended length of contact, and/or undecipherable meaning) that unintentional input is likely, such as when a person is cleaning the screen, a person is leaning against or holding the screen for support, or a child is playing with the screen, etc.

After the display 400 moves into an auto-lock mode, the processor 280B can become unresponsive to all but a certain type of pre-determined touch input. For example, in an auto-lock mode, the display 400 may present the screen as normal until it is touched in some manner and then it may display an activation icon such as with a "swipe to unlock" message or other icon or message prompting a user to perform a particular type of pre-determined or intentional touch or motion on or across a certain portion of the screen in order to reactivate the display 400 to receive standard inputs from a user. In some embodiments, the activation icon can appear at essentially the same time as the display enters auto-lock mode. In some embodiments, the display 400 can be configured to enter a lock mode when intentionally prompted by a user to do so (such as by actuating a lock icon on the display 400 or a lock button on the housing of the pump 10), rather than triggering the lock mode automatically. The return from an intentional lock mode to a normal operating mode can be the same as or similar to that described for returning from an auto-lock mode to a normal operating mode.

TERMINOLOGY AND CONCLUSION

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in this description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single disclosed embodiment.

Embodiments of the disclosed systems and methods may be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may be comprised of connected logic units, such as gates and flip-flops, and/or may be comprised of programmable units, such as programmable gate arrays, application specific integrated circuits, and/or processors. The modules described herein are preferably implemented as software modules, but may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

A number of applications, publications, and external documents may be incorporated by reference herein. Any conflict or contradiction between a statement in the body text of this specification and a statement in any of the incorporated documents is to be resolved in favor of the statement in the body text.

Terms of equality and inequality (e.g., less than, greater than) are used herein as commonly used in the field, e.g., accounting for uncertainties present in measurement and control systems. Thus, such terms can be read as approximately equal, approximate less than, and/or approximately greater than. In other aspects of the invention, an acceptable threshold of deviation or hysteresis can be established by the pump manufacturer, the editor of the drug library, or the user of a pump.

While the embodiments of the invention disclosed herein are presently considered to be preferred, various changes and modifications can be made without departing from the scope of the invention. Although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above. The scope of the invention is indicated in the appended claims, and all changes that come within the meaning and range of equivalents are intended to be embraced therein.

The following is claimed:

1. A medical infusion pump system comprising:
an electronic processor with an electronic memory;
an electrical power cable or battery;
an electromechanical pump driver configured to receive a disposable fluid holder and to pump medical fluid through the disposable fluid holder, wherein the electromechanical pump driver generates a signal indicating whether the disposable fluid holder has been received by the electromechanical pump driver; and
an electronic display;
wherein:
the electronic processor is configured to retrieve from the electronic memory and show on the electronic display one or more repeating graphics or animations comprising an illustration of at least a portion of the medical infusion pump system and the disposable fluid holder;
the illustration is configured to denote movement with a representation of the disposable fluid holder being inserted into the medical infusion pump system; and
the electronic processor is configured to automatically stop the illustration on the electronic display and automatically transition to the electronic display to an interface for inputting pumping parameters when the electronic processor confirms that the disposable fluid holder has been received by the medical infusion pump system in response to the signal generated by the electromechanical pump driver.

2. The combination of the medical infusion pump system of claim 1 and the disposable fluid holder.

3. The medical infusion pump system of claim 1, further comprising a plurality of electromechanical pump drivers, wherein each of the plurality of electromechanical pump drivers are configured to receive a separate disposable fluid holder.

4. The medical infusion pump system of claim 3, wherein the medical infusion pump system comprises a plurality of display regions, each of the plurality of display regions corresponding to one of the plurality of electromechanical pump drivers.

5. The medical infusion pump system of claim 4, wherein a separate graphic or animation is configured to be displayed on each of the plurality of display regions until the disposable fluid holder is inserted into a corresponding electromechanical pump driver for each display region.

6. The medical infusion pump system of claim 4, wherein the electronic processor is configured to automatically stop the illustration on one of the plurality of display regions in response to the disposable fluid holder being received by one of the plurality of electromechanical pump drivers while the remaining plurality of display regions continue to denote movement of the disposable fluid holder being inserted into the medical infusion pump system.

7. The medical infusion pump system of claim 1, wherein the disposable fluid holder is a cassette.

8. A medical infusion pump system comprising:
an electronic processor with an electronic memory;
an electrical power cable or battery;
a plurality of electromechanical pump drivers configured to receive a plurality of disposable fluid holders, the plurality of electromechanical pump drivers being configured to pump medical fluid through the plurality of disposable fluid holders, the plurality of disposable fluid holders being connectable to one or more fluid lines from one or more fluid source containers; and an electronic display comprising a first display region and a second display region, the first display region and the second display region each comprising a sensing region configured to detect a user's touch selection, the first display region corresponding to a first electromechanical pump driver of the plurality of electromechanical pump drivers, the second display region corresponding to a second electromechanical pump driver of the plurality of electromechanical pump drivers;

wherein:

the electronic processor is configured to retrieve from the electronic memory and show on the electronic display a graphic that includes a first indicator and a second indicator;

the first indicator is configured to denote a first location of the first electromechanical pump driver positioned on the medical infusion pump system in the first display region; and the second indicator is configured to denote a second location of the second electromechanical pump driver positioned on the medical infusion pump system in the second display region.

9. The combination of the medical infusion pump system of claim 8 and the plurality of disposable fluid holders, the one or more fluid lines, and the one or more fluid source containers.

10. The medical infusion pump system of claim 8, further comprising a second electronic processor configured to control the plurality of electromechanical pump drivers.

11. The medical infusion pump system of claim 8, wherein the electronic display is configured to illustrate a connection point corresponding to a fluid line of the one or more fluid lines of the plurality of disposable fluid holders.

12. The medical infusion pump system of claim 11, wherein the electronic display comprises a machine-readable code.

13. The medical infusion pump system of claim 8, wherein the electronic display is configured to display pumping information.

14. The medical infusion pump system of claim 8, wherein the electronic display is configured to show product graphics corresponding to the first electromechanical pump driver and the second electromechanical pump driver.

15. A medical infusion pump system comprising:

an electronic processor with an electronic memory;

an electrical power cable or battery;

an electromechanical pump driver configured to receive at least one disposable fluid holder and to pump medical fluid through the at least one disposable fluid holder, the at least one disposable fluid holder being connectable to one or more fluid lines from one or more fluid source containers; and an electronic display comprising a sensing region configured to detect a user's touch selection;

wherein the electronic display is configured to permit a user to input multiple pumping stages comprising one or more different pumping parameters to be performed sequentially by the medical infusion pump system, and wherein the electronic display is configured to show multiple representations of the multiple pumping stages simultaneously and sequentially on the electronic display to represent an order of execution of the multiple pumping stages.

16. The medical infusion pump system of claim 15, wherein the electronic display is configured to permit the user to scroll through a list of multiple pumping stages to permit selective viewing of more pumping stages than are displayed simultaneously on the electronic display.

17. The medical infusion pump system of claim 15, wherein the electronic display is configured to permit the user to insert a new pumping stage sequentially between two previously programmed pumping stages.

18. The medical infusion pump system of claim 15, wherein the electronic display is configured to automatically change a fluid infusion rate between a first pumping stage and a second pumping stage.

19. The medical infusion pump system of claim 15, wherein the multiple pumping stages comprise a plurality of shapes of substantially a same size with a plurality of pumping parameters contained within each shape.

20. The medical infusion pump system of claim 19, wherein the plurality of shapes of substantially the same size are generally square in shape.

* * * * *